(12) United States Patent
Frenken et al.

(10) Patent No.: US 6,670,453 B2
(45) Date of Patent: *Dec. 30, 2003

(54) MULTIVALENT ANTIGEN-BINDING PROTEINS

(75) Inventors: Leon Gerardus Frenken, Vlaardingen (NL); Steven Howell, Bedford (GB); Adrianus Marinus Ledeboer, Vlaardingen (NL); Cornelis P van der Logt, Bedford (GB)

(73) Assignee: Unilever Patent Holdings B.V., Vlaardingen (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/530,139

(22) PCT Filed: Oct. 27, 1998

(86) PCT No.: PCT/EP98/06991

§ 371 (c)(1),
(2), (4) Date: Apr. 27, 2000

(87) PCT Pub. No.: WO99/23221

PCT Pub. Date: May 14, 1999

(65) Prior Publication Data

US 2003/0092892 A1 May 15, 2003

(30) Foreign Application Priority Data

Oct. 27, 1997 (EP) .............................. 97308538

(51) Int. Cl.[7] .............................. C07K 16/00
(52) U.S. Cl. ............... 530/387.3; 530/387.1; 530/391.3; 435/188
(58) Field of Search ............ 530/387.1, 387.3, 530/391.3; 435/188

(56) References Cited

U.S. PATENT DOCUMENTS 5,837,242 A * 11/1998 Holliger et al.

FOREIGN PATENT DOCUMENTS

| EP | 0 368 684 A | | 5/1990 |
|----|-------------|---|--------|
| WO | 93/11161 A | | 6/1993 |
| WO | 94/13806 A | | 6/1994 |
| WO | WO 94/13806 | * | 6/1994 |
| WO | 94/25591 A | | 11/1994 |
| WO | WO 96/34103 | | 10/1996 |
| WO | 97/38102 A | | 10/1997 |

OTHER PUBLICATIONS

M. Arbabi–Ghahroudi et al.: "Selection and identification of single domain antibody fragments from camel heavy–chain antibodies." FEBS Letters, vol. 414, Sep. 15, 1997, pp. 521–526 XP002069903 Amsterdam, The Netherlands p. 525, right–hand co;umn, line 35–line 42 abstract.

H. Hoogenboom: "Mix and match: Building manifold binding sites." Nature Biotechnology, vol. 15, No. 2, Feb. 1997 pp. 125–126, XP002110046 New York, NY, USA, p. 126, right–hand column, line 30–line 39, figure 1.

D. Neri et al: "High–affinity antigen binding by chelating recombinant antibodies (CRAbs)" Journal of Molecular Biology, vol. 246, 1995, pp. 367–373, XP002092191 Oxford, GB abstract figure 2.

C. Ill et al: "Design and construction of a hybrid immunoglobulin domain with properties of both heavy and light chain variable regions. " Protein Engineering, vol. 10, No. 8, Aug. 1997, pp. 949–957, XP002110047 Oxford, GB abstract p. 956, right–hand column, line 2–line 30.

* cited by examiner

Primary Examiner—Larry R. Helms
(74) Attorney, Agent, or Firm—Paul N. Kokulis; Bonnie Weiss McLeod

(57) ABSTRACT

A multivalent antigen binding protein comprises a single polypeptide chain comprising, in series, two or more single domain binding units which are preferably heavy chain variable domains derived from an immunoglobulin naturally devoid of light chains. Methods for their production and uses thereof, in particular for diagnosis, immunoassay and purification methods are disclosed.

7 Claims, 33 Drawing Sheets

Figure 1. Schematic representation of Camelidae IgG types

FIG. 2

JR 4640 ANTI-RR6 R9

```
            PstI
    CAGGTGCAGCTGCAGGAGTCAGGGGGAGGCTTGGTGCAGCCTGGGGACTCTCTGAAACTCTCCTGTGCAGCCTCTGGAAACACCTTCAGT
1   --------+---------+---------+---------+---------+---------+---------+---------+---------+    90
    GTCCACGTCGACGTCCTCAGTCCCCCTCCGAACCACGTCGGACCCCCTGAGAGACACGTCGGAGACCTTTGTGGAAGTCA
    Q  V  Q  L  Q  E  S  G  G  G  L  V  Q  P  G  G  S  L  K  L  S  C  A  A  S  G  N  T  F  S
                                                                        [-> CDR I

KpnI
    GGGGGCTTCATGGGGTACCGCCAGGCTCCAGGGAAGCAGCCGAGTTGGTCGCAACCATTAATAGTAGAGGTATCACAAACTATGCA
1   --------+---------+---------+---------+---------+---------+---------+---------+---------+    180
    CCGCCGAAGTACCCCATGGCGGTCCGAGGTCCCTTCGTCGGCTCAACCAGCGTTGGTAATTATCATCTCCATAGTGTTGATACGT
    G  G  F  M  G  W  Y  R  Q  A  P  G  K  Q  R  E  L  V  A  T  I  N  S  R  G  I  T  N  Y  A
    <-]                                                                 [-> CDR II
                                                                            EagI

GACTTCGTGAAGGGCCGATTCACCATCTCCAGAGACAATGCCAAGAAGACAGTGTATTTGGAAATGAACAGCCTGGAACCTGAAGACACG
1   --------+---------+---------+---------+---------+---------+---------+---------+---------+    270
    CTGAAGCACTTCCCGGCTAAGTGGTAGAGGTCTCTGTTACGGTTCTTCTGTCACATAAACCTTTACTTGTCGGACCTTGGACTTCTGTGC
    D  F  V  K  G  R  F  T  I  S  R  D  N  A  K  K  T  V  Y  L  E  M  N  S  L  E  P  E  D  T
                                                              BstEII

GCCGTTTATTACTGTGTTACACTCACTACTTCAGATCCTCACTGGGGTCAGGGGACCCAGGTCACCGTCTCCTCA
1   --------+---------+---------+---------+---------+---------+---------+------    342
    CGGCAAATAATGACAACATGTGAGTGATGAAGTCTAGGATGATGAAGTCTAGGAGTGACCCCAGTCCCCTGGGTCCAGTGGCAGAGGAGT
    A  V  Y  Y  C  V  T  H  Y  F  R  S  Y  W  G  Q  G  T  Q  V  T  V  S  S
                    [-> CDR III <-]
```

FIG. 3

R 4601 ANTI-hCG H14

```
         PstI
    CAGGTGCAGCTGCAGGAGTCAGGGGGAGGATTGGTGCAGGCCGGGGGGTCTCTGAGACTCTCCTGTGCAGCCTCTGGACGCACCGGCAGT
1   ---------+---------+---------+---------+---------+---------+---------+---------+---------+   90
    GTCCACGTCGACGTCCTCAGTCCCCCTCCTAACCACGTCCGGCCCCCCAGAGACGTCCGGAGACTCTGAGAGGACACGTCGGAGCCGTCA
     Q  V  Q  L  Q  E  S  G  G  G  L  V  Q  A  G  G  S  L  R  L  S  C  A  A  S  G  R  T  G  S

ACGTATGACATGGGCTGGTTCCGCCAGGCTCCAGGGAAGGAGCGTGAGTCGTGTAGCAGCTATTAACTGGATAGTGCGCACATACTAT
1   ---------+---------+---------+---------+---------+---------+---------+---------+---------+  180
    TGCATACTGTACCCGACCAAGGCGGTCCGAGGTCCCTTCCTCGCACTCAGAGCACATCGTCGATAATTGACCTATCACGCGTGTATGATA
     T  Y  D  M  G  W  F  R  Q  A  P  G  K  E  R  E  S  V  A  A  I  N  W  D  S  A  R  T  Y  Y
    1-> CDR I <-1                                          1-> CDR II                   EagI

GCAAGCTCCGTGAGGGGCCGATTCACCATCTCCAGAGACAACGCCAAGAAGACGGTGTATCTGCAAATGAACAGCCTGAAACCTGAGGAC
1   ---------+---------+---------+---------+---------+---------+---------+---------+---------+  270
    CGTTCGAGGCACTCCCCGGCTAAGTGGTAGAGGTCTCTGTTGCGGTTCTTCTGCCACATAGACGTTTACTTGTCGGACTTTGGACTCCTG
     A  S  S  V  R  G  R  F  T  I  S  R  D  N  A  K  K  T  V  Y  L  Q  M  N  S  L  K  P  E  D
                                 <-1                                              BstEII

ACGGCCGTTTATACCTGTGGCGCGGAGGGGGGAACCTGGGACAGTTGGGGCCAGGGGACCCAGGTCACCGTCTCCTCA
1   ---------+---------+---------+---------+---------+---------+---------+-------    351
    TGCCGGCAAATATGGACACCGCGCCTCCCCCCCTTGGACCCTGTCAACCCCGGTCCCCTGGGTCCAGTGGCAGAGGAGT
     T  A  V  Y  T  C  G  A  G  E  G  G  T  W  D  S  W  G  Q  G  T  Q  V  T  V  S  S
                     1->           CDR III              <-1
```

FIG. 4

R 4602 ANTI-hCG HI-15

```
         PstI
     CAGGTGCAGCTGCAGGAGTCTGGGGGAGAATTGGTGCAGCCTCTCTGAAACTCTCCTGCGCAGCCTCTGGACTTACCTTCACT
1    ----+----|----+----|----+----|----+----|----+----|----+----|----+----|----+----|     90
     GTCCACGTCGACGTCCTCAGAGACCCCCTCTTAACCACGTCGGAGAGACTTTGAGAGGACGCGTCGGAGACCTGAATGGAAGTGA
      Q  V  Q  L  Q  E  S  G  G  E  L  V  Q  P  G  G  S  L  K  L  S  C  A  A  S  G  L  T  F  T

AATTATATAGCATGGGCTGGTTCCGCCAGGCTCCAGGGAAGGGTCTGGAGTGGGTCGCCTATTAGCTGGAGTGGTGATAACACATACTAT
1    ----+----|----+----|----+----|----+----|----+----|----+----|----+----|----+----|     180
     TTAATATATCGTACCCGACCAAGGCGGTCCGAGGTCCCTTCCCAGACCTCACCCAGCGGATAATCGACCTCACCACTATTGTGTATGATA
      N  Y  S  M  G  W  F  R  Q  A  P  G  V  D  R  E  A  V  A  A  I  S  W  S  G  D  N  T  Y  Y
     1-> CDR I <-1                                                  1-> CDR II

GTAAGCTCCGTGAAGGGACGATTCACCATCTCCAGAGACAACGCCAAGAACACGGTGTATCTGCAAATGAACAGCCTGAAACCTCAAGAC
1    ----+----|----+----|----+----|----+----|----+----|----+----|----+----|----+----|     270
     CATTCGAGGCACTTCCCTGCTAAGTGGTAGAGGTCTCTGTTGCGGTTCTTGTGCCACATAGACGTTTACTTGTCGGACTTTGGAGTTCTG
      V  S  S  V  K  G  R  F  T  I  S  R  D  N  A  K  N  T  V  Y  L  Q  M  N  S  L  K  P  Q  D
                               <-1                                         BstEII

EagI
     ACGGCCGTTTATTACTGTGCAGTAAAACCCGACGATGGTTGGTGGGACTACTGGGGCCAGGGGACCCAGGTCACCGTCTCCTCA
1    ----+----|----+----|----+----|----+----|----+----|----+----|----+----|----+----       354
     TGCCGGCAAATAATGACACGTCATTTTGGGCTGCTACCAACCACCCTGATGACCCCGGTCCCCTGGGTCCAGTGGCAGAGGAGT
      T  A  V  Y  Y  C  A  V  K  P  D  D  G  W  D  Y  W  G  Q  G  T  Q  V  T  V  S  S
                          1-> CDR III                <-1
```

FIG. 5

JR 4603 ANTI-STREPTOCOCCUS S36

```
     PstI
    CAGGTGCAGCTGCAGGAGTCAGGGGAGGCTTGGTGTGCAGCCTGGGGGGGTCTCTGAGACTCTCCTGTGCAGCCTCTGGATTCCCTTCAAT       90
  1 ---------+---------+---------+---------+---------+---------+---------+---------+---------+
    GTCCACGTCGACGTCCTCAGTCCCCTCCGAACCACACGTCGGACCCCCCAGAGACTCTGAGAGGACACGTCGGAGACCTAAGGGAAGTTA
     Q  V  Q  L  Q  E  S  G  G  G  L  V  Q  P  G  G  S  L  R  L  S  C  A  A  S  G  F  A  F  N
                                              XhoI
    CTCTACTGGATGTATTGGTTCCGTCAGGCTCCAGGCAAGGGACTCGAGTGGGTCTCGAGTCCTGGTAATGGTATCACTTTCAAT       180
  1 ---------+---------+---------+---------+---------+---------+---------+---------+---------+
    GAGATGACCTACATAACCAAGGCAGTCCGAGGTCCGTTCCCTGAGCTCACCCAGAGCTCAGGACCATTACCATAGTGAAAGTTA
     L  Y  W  M  Y  W  F  R  Q  A  P  G  K  G  L  E  W  V  S  S  A  S  P  G  N  G  I  T  F  N
    1->  CDR I  <-1                                                     1->        CDR II

ACATTCTACGCGGACTCCGTGAAGGACGGTTCGCCATCTCCAGAGACAACGCCAAAAACACACTGTATCTGGAGATGAACAGTCTACAA       270
  1 ---------+---------+---------+---------+---------+---------+---------+---------+---------+
    TGTAAGATGCGCCTGAGGCACTTCCTGCCAAGCGGTAGAGGTCTCTGTTGCGGTTTTGTGACATAGACCTCTACTTGTCAGATGTT
     T  F  Y  A  D  S  V  K  G  R  F  A  I  S  R  D  N  A  K  N  T  L  Y  L  E  M  N  S  L  Q
                                                                  <-1
        EagI
    CCTGAGGAGACGCCGGTGTATTATTGTGCTGCCGACCCCTCGTATCAACTCGCGGACTTTTTGACTTCGCTGCCGAATGACTACTCGGGC       360
  1 ---------+---------+---------+---------+---------+---------+---------+---------+---------+
    GGACTCCTCTGCGGCCACATAATAACACGACGGCTGGGGAGCATAGTTGAGCGCCTGAAAAACTGAAGCGACGGCTTACTGATGAGCCCG
     P  E  D  T  A  V  Y  Y  C  A  A  D  P  S  Y  Q  L  A  D  F  L  T  S  L  P  N  D  Y  S  G
                            CDR III
                        1->                                                           <-1
     BstEII
    CAGGGAACCCAGGTCACCGTCTCCTCA       387
  1 ---------+---------+-------
    GTCCCTTGGGTCCAGTGGCAGAGGAGT
     Q  G  T  Q  V  T  V  S  S
```

FIG. 6

R 4642 ANTI-STREPTOCOCCUS S120

```
       PstI
CAGGTGCAGCTGCAGGAGTCAGGGGGAGGACTGGTGCAGGCTGGGGAGAGTCTGAGACTCTCCTGTGTAGCCTCGGGCCTCTCCTTCAGT
----+---------+---------+---------+---------+---------+---------+---------+---------+    90
GACCACGTCGACGTCCTCAGTCCCCCTCCTGACCACGTCCGACCCCCTCTCAGACTCTGAGAGGACACATCGGAGCCCGGAGAGGAAGTCA
 Q  V  Q  L  Q  E  S  G  G  G  L  V  Q  A  G  E  S  L  R  L  S  C  V  A  S  G  L  S  F  S

GAATTCGTCATGACATGGTTCCGCCAGGCTCCAGGGAAGGAGCGTGAGTTTGTAGCAGGATTAACTGGATGGATGATCGTACATATTAT
----+---------+---------+---------+---------+---------+---------+---------+---------+   180
CTTAAGCAGTACTGTACCAAGGCGGTCCGAGGTCCCTTCCTCGCACTCAAACATCGTCCTAATTGACCTACCTACTAGCATGTATAATA
 E  F  V  M  T  W  F  R  Q  A  P  G  K  E  R  E  F  V  A  A  I  N  W  M  D  D  R  T  Y  Y
 1->  CDR I <-1                                             EagI        CDR II
                                                                                  1->

GGAAGTTCCGTGAAGGGCCGATTCTTCATCTCCAAAGACAACGCCAAGAACACAGTGTATCTTCAAATGAACCGTGAAACCTGAGGAC
----+---------+---------+---------+---------+---------+---------+---------+---------+   270
CCTTCAAGGCACTTCCCGGCTAAGAAGTAGAGGTTTCTGTTGCGGTTCTTGTGTCACATAGAAGTTTACTTGCCGACTTTGGACTCCTG
 G  S  S  V  K  G  R  F  F  I  S  K  D  N  A  K  N  T  V  Y  L  Q  M  N  G  L  K  P  E  D

BstEII
ACGGCCGTTTATTACTGTGCAGCCAGTAGGGATTACTATGGCCACAATGCCAATCAGTATGCCTACTGGGGCCAGGGGACCCAGGTCACCGTCTCCTCA
----+---------+---------+---------+---------+---------+---------+---------+---------+----   369
TGCCGGCAAATAATGACACGTCGGTCATCCTAATGATACCGGTGTTAGTCATACGGATGACCCCGGTCCCCTGGGTCCAGTGGCAGAGGAGT
 T  A  V  Y  Y  C  A  A  S  R  D  Y  Y  G  H  N  A  N  Q  Y  R  Y  W  G  Q  G  T  Q  V  T  V  S  S
              CDR III                                  <-1
```

R 4619 (BIHEAD H14-R9)

```
                                                                                    KpnI
        GGGGGAGGCTTGGTGCAGGCTGGGGAGTCTCTCTGAAACTCTCCTGTGCAGCCTCTGGATTCAGTGGCGCTTCATGGGCTGGTAC
     1  ------+---------+---------+---------+---------+---------+---------+---------+--------  450
        CCCCCTCCGAACCACGTCCGACCCCTCAGAGAGACACGTCGGAGACCTTTGTGGAAGTCACCGCGAAGTACCGACCATG
         G  G  L  V  Q  A  G  E  S  L  K  L  S  C  A  A  S  G  F  S  G  F  M  G  W  Y
                                                1->                  CDR I           <-1

CGCCAGGCTCCAGGGAAGCAGCGCGAGTTGGTCGCAACCATTAATAGTAGAGGTATCACAAACTATGCAGACTTCGTGAAGGGCCGATTC
     1  ------+---------+---------+---------+---------+---------+---------+---------+--------  540
        GCGGTCCGAGGTCCCTTCGTCGCGCTCAACCAGCGTTGGTAATTATCATCTCCATAGTGTTTGATACGTCTGAAGCACTTCCCGGCTAAG
         R  Q  A  P  G  K  Q  R  E  L  V  A  T  I  N  S  R  G  I  T  N  Y  A  D  F  V  K  G  R  F
                                          1->                  CDR II                      <-1
                                                                                        EagI

ACCATCTCCAGAGACAATGCCAAGAAGACAGTGTATTTGGAAATGAACAGCCTGGAACCTGAAGACACGGCCGTTTATTACTGTTACACT
     1  ------+---------+---------+---------+---------+---------+---------+---------+--------  630
        TGGTAGAGGTCTCTGTTACGGTTCTTCTGTCACATAAACCTTTACTTGTCGGACCTTGGACTTCTGTGCCGGCAAATAATGACAATGTGA
         T  I  S  R  D  N  A  K  K  T  V  Y  L  E  M  N  S  L  E  P  E  D  T  A  V  Y  Y  C  Y  T
                                                                                      BstEII

CACTACTTCAGATCCTCAGGGGTCAGGGGACCCAGTCCACC
     1  ------+---------+---------+---------+--  672
        GTGATGAAGTCTAGGAGTCCCCAGTCCCCTGGGTCAGGTGG
         H  Y  F  R  S  Y  W  G  Q  G  T  Q  V  T
         1-> CDR III  <-1
```

FIG. 9B

R 4620 (BIHEAD HI 15-R7)

```
       XhoI
    CTCGAGTCTGGGGGAGAATTGGTGCAGCCTGGGGGCTCTCTGAAACTCTCCTGCGCAGCCTCTGGACTTACCTTCACTAATTATAGCATG
1   ---------+---------+---------+---------+---------+---------+---------+---------+---------+   90
    GAGCTCAGATCCCCCTCTTAACCACGTCGGACCCCCGAGAGACTTTGAGAGGACGCGTCGGAGACCTGAATGGAAGTGATTAATATCGTAC
     L  E  S  G  G  E  L  V  Q  P  G  G  S  L  K  L  S  C  A  A  S  G  L  T  F  T  N  Y  S  M
                                                                        1->    CDR I

GGCTGGTTCCGCCCAGGTCCAGGAGTGGACTGGAGCCCGTAGCCGCTATTAGCTGGAGTGGTGATAACACATATTATGTAAGCTCCGTG
1   ---------+---------+---------+---------+---------+---------+---------+---------+---------+   180
    CCGACCAAGGCGGGTCCAGGTCCTCAGTGCACTCCGGGCATCGGCGATAATCGACCTCACCACTATTGTGTATAATACATTCGAGGCAC
     G  W  F  R  P  G  P  G  V  D  R  E  A  V  A  A  I  S  W  S  G  D  N  T  Y  Y  V  S  S  V
                                           <-1                    1->    CDR II
                                                   EagI
    AAGGGGACGATTCACCATCTCCAGAGAGACAACGCCAAGAACACCGTGTATCTGCAAATGAACAGCCTGAAACTCAAGACACGGCCGTTTAT
1   ---------+---------+---------+---------+---------+---------+---------+---------+---------+   270
    TTCCCCTGCTAAGTGGTAGAGGTCTCTCTGTTGCGGTTCTTGTGGCACATAGACGTTTACTTGTCGGACTTTGAGTTCTGTGCCGGCAAATA
     K  G  R  F  T  I  S  R  D  N  A  K  N  T  V  Y  L  Q  M  N  S  L  K  P  Q  D  T  A  V  Y
    <-1
                                                       BstEII                      PstI
    TACTGTGCAGTAAAACCCGACGATGGTTGGTGGACTACTGGGGCCAGGGGACTCCTCACAGGTCACCGTCTCCTCAGGTGCCAGCTGCAGGAG
1   ---------+---------+---------+---------+---------+---------+---------+---------+---------+   360
    ATGACACGTCATTTTGGGCTGCTACCAACCACCCTGATGACCCCGGTCCCCTGAGGAGTGTCCAGTGGCAGAGGAGTGTCCACGTCGACGTCCTC
     Y  C  A  V  K  P  D  D  G  W  D  Y  W  G  Q  G  T  Q  V  T  V  S  S  Q  V  Q  L  Q  E
     1->     CDR III                     <-1
```

FIG. 10A

R 4620 (BIHEAD HI 15-R7)

```
                                                                                    KpnI
     TCAGGGGGAGGATTGTGCAGGCTGGGACTCTCTGAGACTCTCCTGCGCGGCCTCGGGGACGCACTTCTCATGGTTATGTGGTGGCTATGGC
  1  ------+---------+---------+---------+---------+---------+---------+---------+---------+  450
     AGTCCCCCCTCCTAACCACGTCCGACCCTGAGAGACTCTGAGAGGACGCGCCGGAGCCCTGCGTGAAGAGTACCCAATACCACCGATACCG
     S  G  G  G  L  V  Q  A  G  D  S  L  R  L  S  C  A  A  S  G  R  T  S  H  G  G  Y  G
                                                                                       CDR I
                                                                                       1->

ATGGGCTGGTTCCGCCAAATTCCAGGGAAGGAGCGTGAGCTTGTCGCAGCAATTAGGTGGAGCGGTCGTAATACATACTATGCAGACTCC
  1  ------+---------+---------+---------+---------+---------+---------+---------+---------+  540
     TACCCGACCAAGGCGGTTTAAGGTCCCTTCCTCGCACTCGAACAGCGTCGTTAATCCACCTCGCCAGCATTATGTATGATACGTCTGAGG
     M  G  W  F  R  Q  I  P  G  K  E  R  E  L  V  A  A  I  R  W  S  G  R  N  T  Y  Y  A  D  S
     <-1                                               1->                         CDR II

EagI
     GTGAAGGGCCGATTCACCATCTCCAGAGACAACGTCAAGGACATGCTATCTGCAAATGAACAGTTTGAAACCTGAGGACACGGCCGTT
  1  ------+---------+---------+---------+---------+---------+---------+---------+---------+  630
     CACTTCCCGGCTAAGTGGTAGAGGTCTCTGTTGCAGTTCCTGTACGACATAGACGTTTACTTGTCAAACTTTGGACTCCTGTGCCGGCAA
     V  K  G  R  F  T  I  S  R  D  N  V  K  D  M  L  Y  L  Q  M  N  S  L  K  P  E  D  T  A  V
     <-1

BstEII
     TACACTTGTGCAGTTCGGACGGTTCGCGTGTTGACATTTCCAGTCCGGTTGGTTTGCCTACTGGGGCCAGGGGACCCAGGTCACC
  1  ------+---------+---------+---------+---------+---------+---------+---------+---------+  717
     ATGTGAACACGTCAAGCCTGCCAAGGCGCACCAACTGTAAAGGTCAGGCCAACCAAACGGATGACCCCGGTCCCCTGGGTCCAGTGG
     Y  T  C  A  V  R  T  V  R  V  V  D  I  S  S  P  V  G  F  A  Y  W  G  Q  G  T  Q  V  T
     1->                       CDR III                           <-1
```

*FIG. 10B*

R 4621 (BIHEAD HI 15-R9)

```
            XhoI
      CTCGAGTCTGGGGGAGAATTGGTGCAGCCTGGGGGCTCTCTGAAACTCTCCTGCGCAGCCTCTGGACTTACCTTCACTAATTATAGCATG
1     ---------+---------+---------+---------+---------+---------+---------+---------+---------    90
      GAGCTCAGACCCCCTCTTAACCACGTCGGACCCCCGAGAGACTTTGAGAGGACGCGTCGGAGACCTGAATGGAAGTGATTAATATCGTAC
       L  E  S  G  G  E  L  V  Q  P  G  G  S  L  K  L  S  C  A  A  S  G  L  T  F  T  N  Y  S  M
                                                                              1-> CDR I

GGCTGGTTCCGCCCAGGTCCAGGAGAGTGGAGACCGTGAGGCCGTAGCCGCGTATTAGCTGGAGTGGTGATAACACATACTATGTAAGCTCCGTG
1     ---------+---------+---------+---------+---------+---------+---------+---------+---------   180
      CCGACCAAGGCGGGTCCAGGTCCAGGTCCTCACCTCTGGCACTCCGGCATGGCGCATAATCGACCTCACCACTATTGTGTGATGATACATTCGAGGCAC
       G  W  F  R  P  G  P  G  V  D  R  E  A  V  A  A  I  S  W  S  G  D  N  T  Y  Y  V  S  S  V
                                                              1->              CDR II      EagI

AAGGGACGATTCACCATCTTCCAGAGACAACAAGCCTCAAGAACACGGTGTATCTGCAAATGAACAGCCTGAAACCTGAAGACTTTGGAGTTCTGTGCCGCAAATA
1     ---------+---------+---------+---------+---------+---------+---------+---------+---------   270
      TTCCCTGCTAAGTGGTAGAGGTCTCTGTTGTTCGGAGTTCTTGTGCCACATAGACGTTTACTTGTCGGACTTTGGACTTCTGAAACCTCAAGACACGGCGTTTAT
       K  G  R  F  T  I  S  R  D  N  A  K  N  T  V  Y  L  Q  M  N  S  L  K  P  Q  D  T  A  V  Y
       <-1                                                                            BstEII        PstI

TACTGTGCAGTAAAACCCGACGATGGTTGGTGGGACTACTGGGGCCAGGGGACCCAGGTCACCGTCTCCTCACAGGTGTCACGTGTCAGCTGCAGGAG
1     ---------+---------+---------+---------+---------+---------+---------+---------+---------   360
      ATGACACGTCATTTGGGCTGCTACCAACCACCCTGATGACCCCGGTCCCCTGGGTCCAGTGGCAGAGGAGTGTCCAGTGGCAGAGTGCACGTCCTC
       Y  C  A  V  K  P  D  D  G  W  D  Y  W  G  Q  G  T  Q  V  T  V  S  S  Q  V  L  Q  E
       1->     CDR III                  <-1
```

FIG. 11A

R 4621 (BIHEAD HI 15-R9)

```
                                                                            KpnI
     TCAGGGGGAGGCTTGTGTGCAGGCTGGGGGAGTCTCCTGTGCAGCCTCTGGAAACACCTTCAGTGGCGGCTTCATGGGCTGG
1    ---------+---------+---------+---------+---------+---------+---------+---------+  450
     AGTCCCCCTCCGAACCACACGTCCGACCCCCTCAGAGACTTTGTGGAAGTCACCGCCGAAGTACCCGACC
     S  G  G  G  L  V  Q  A  G  E  S  L  K  L  S  C  A  A  S  G  N  T  F  S  G  G  F  M  G  W
                                                              1->    CDR I            <-1

TACCGCCAGGCTCCAGGGAAGCAGCGGGAGTTGGTCGCCAACCATTAATAGTAGAGGTATCACAAACTATGCAGACTTCGTGAAGGGCCGA
1    ---------+---------+---------+---------+---------+---------+---------+---------+  540
     ATGGCGGTCCGAGGTCCCTTCGTCGCGCTCAACCAGCGGTTGGTAATTATCATCTCCATAGTGTTTGATACGTCTGAAGCACTTCCCGGCT
     Y  R  Q  A  P  G  K  Q  R  E  L  V  A  T  I  N  S  R  G  I  T  N  Y  A  D  F  V  K  G  R
                                           1->      CDR II                            <-1
                                                                            EagI

TTCACCATCTCCAGAGACAATGCCAAGAAGACAGTGTATTTGGAAATGAACAGCCTGAAGACCTGAAGACACGGCCGTTTATTACTGTTAC
1    ---------+---------+---------+---------+---------+---------+---------+---------+  630
     AAGTGGTAGAGGTCTCTGTTACGGTTCTTCTGTCACATAAACCTTTACTTGTCGGACTTCTGTGCCGGCAAATAATGACAATG
     F  T  I  S  R  D  N  A  K  K  T  V  Y  L  E  M  N  S  L  E  P  E  D  T  A  V  Y  Y  C  Y

BstEII
     ACTCACTACTTCAGATCCTACTGGGGTCAGGGGACCCAGGTCACC
1    ---------+---------+---------+---------+----  675
     TGAGTGATGAAGTCTAGGATGACCCCAGTCCCCTGGGTCCAGTGG
     T  H  Y  F  R  S  Y  W  G  Q  G  T  Q  V  T
     1->     CDR III           <-1
```

FIG. 11B

JUR 4622 (BIHEAD R7-R7)

```
        PstI
     CTGCAGGAGTCAGGGGAGGATTGGTGCAGGCTGGGGACTCTCTGAGACTCTCCTGCGCGGCCTCCGGACGCACTTCTCATGGGTATGGT
1    ---------+---------+---------+---------+---------+---------+---------+---------+---------+    90
     GACGTCCTCAGTCCCCTCCTAACCACGTCCGACCCCTGAGAGACTCTGAGAGGACGCGCCGGAGGCCTGCGTGAAGAGTACCCATACCA
      L  Q  E  S  G  G  G  L  V  Q  A  G  D  S  L  R  L  S  C  A  A  S  G  R  T  S  H  G  Y  G
                                                                     1-->     CDR I

GGCTATGGCATGGGCTGGTTCCGCCAAATTCCAGGGAAGGAGCGTGAGCTTGTCGCAGCAATTAGGTGGAGCGGTCGTAATACATACTAT
1    ---------+---------+---------+---------+---------+---------+---------+---------+---------+    180
     CCGATACCGTACCCGACCAAGGCGGTTTAAGGTCCCTTCCTCGCACTCGAACAGCGTCGTTAATCCACCTCGCCAGCATTATGTATGATA
      G  Y  G  M  G  W  F  R  Q  I  P  G  K  E  R  E  L  V  A  A  I  R  W  S  G  R  N  T  Y  Y
                           <--1                                 1-->     CDR II

GCAGACTCCGTGAAGGGCCGATTCACCATCTCCAGAGACAACGTCAAGGACATGCTGTATCTGCAAATGAACAGTTTGAAACCTGAGGAC
1    ---------+---------+---------+---------+---------+---------+---------+---------+---------+    270
     CGTCTGAGGCACTTCCCGGCTAAGTGGTAGAGGTCTCTGTTGCAGTTCCTGTACGACATAGACGTTTACTTGTCAAACTTTGGACTCCTG
      A  D  S  V  K  G  R  F  T  I  S  R  D  N  V  K  D  M  L  Y  L  Q  M  N  S  L  K  P  E  D
                        <--1

EagI                                                              BstEII
     ACGGCCGTTTACACTTGTGCAGTTCGGACGGTTCGAGTCCGGTTGACATTTCCAGTCCGGTTGGGTTTGCCTACTGGGGCCAGGGGACCCAG
1    ---------+---------+---------+---------+---------+---------+---------+---------+---------+    360
     TGCCGGCAAATGTGAACACGTCAAGCCTGCCAAGCTCAGGCCAACTGTAAAGGTCAGGCCACCCAAACGGATGACCCCGGTCCCCTGGGTC
      T  A  V  Y  T  C  A  V  R  T  V  R  V  V  D  I  S  S  P  V  G  F  A  Y  W  G  Q  G  T  Q
                   1-->                        CDR III                                 <--1
```

FIG. 15 RESULTS OF A RR6/RR6 BIFUNCTIONAL BINDING ASSAY

PLASMID MAP OF pHP14.3A

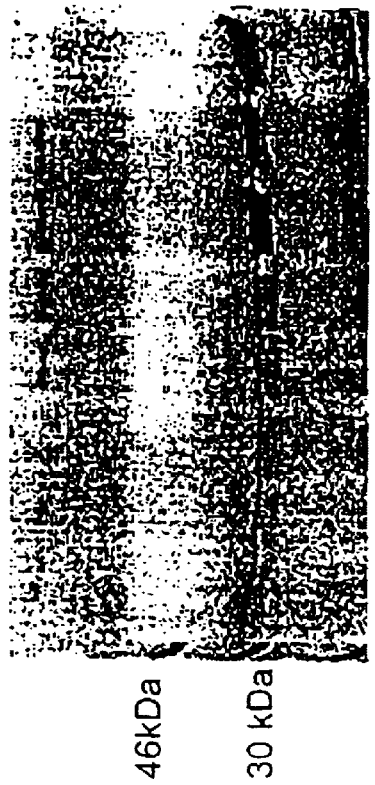
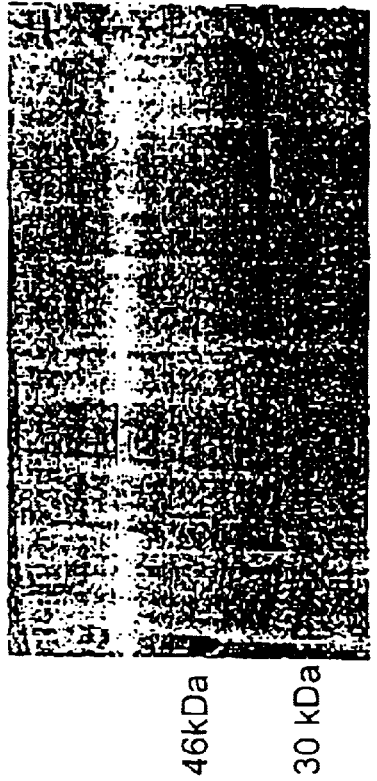
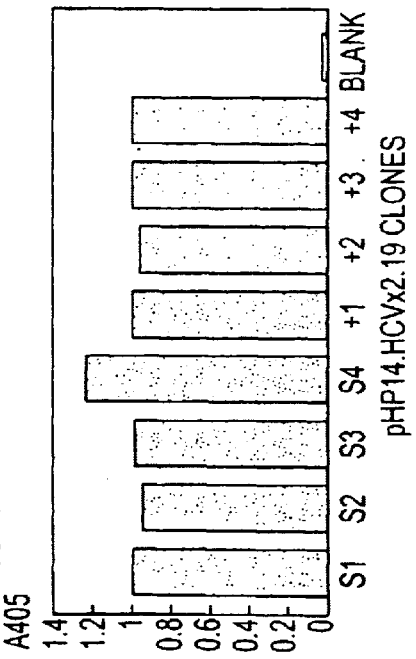
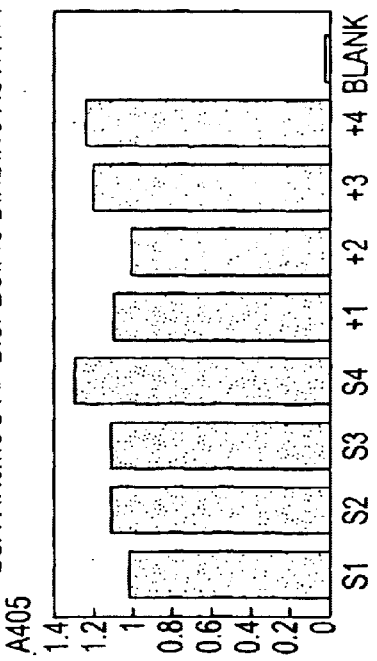
FIG. 18

Fig 19 : Effect of monovalent- and bivalent anti-RR6 antibody fragments on the infectivity of RR6 phages

R4618 (BIHEAD H14--R7)

```
        XhoI
     CTCGAGTCAGGGGGAGGATTGGTGCAGGCGGGGGGCTCTCTGAGACTCTCCTGTGCAGCCTCTGAGACGCACCGGCAGTACGTATGACATG    90
     GAGCTCAGTCCCCCTCCTAACCACGTCCGCCCCCCGAGAGACTCTGAGAGGACACGTCGGAGACCTGCTGCGTGGCCGTCATGCATACTGTAC
      L  E  S  G  G  G  L  V  Q  A  G  G  S  L  R  L  S  C  A  A  S  G  R  T  G  S  T  Y  D  M
                                                                            1->    CDR I

GGCTGGTTCCGCCAGGCTCCAGGGAAGGAGCGTGAGTCTGTAGCAGCTATTAACTGGGATAGTGCGCACATACTATGCAAGCTCCGTG        180
     CCGACCAAGGCGGTCCGAGGTCCCTTCCTCGCACTCAGACATCGTCGATAATTGACCCTATCACGCGTGTATGATACGTTCGAGGCAC
      G  W  F  R  Q  A  P  G  K  E  R  E  S  V  A  A  I  N  W  D  S  A  R  T  Y  Y  A  S  S  V
                                                              1->    CDR II

AGGGGCCGATTCACCATCTCCAGAGACAACGCCAAGAAGACGGTGTATCTGCAAATGAACAGCCTGAAACCTGAAGGACACGGCCGTTTAT    270
     TCCCCGGCTAAGTGGTAGAGGTCTCTGTTGCGGTTCTTCTGCCACATAGACGTTTACTTGTCGGACTTTGGACTTCCTGTGCCGGCAAATA
      R  G  R  F  T  I  S  R  D  N  A  K  K  T  V  Y  L  Q  M  N  S  L  K  P  E  D  T  A  V  Y
                                                                                    BstEII    PstI
     ACCTGTGCGGCGGGGGAAGGTGGGACTCCTGGGGCCAGGGGACCCCAGGGGTCCCCTGGTCCCCAGTGGCAGAGAGTGTCCACGTCGACGTCCTCAGT   360
     TGGACACGCCGCCCCCCTTCCACCCTGAGGACCCCGGTCCCCTGGGGTCCCCAGGGGACCAGGGGTCACCGTCTCACAGGAGTCA
      T  C  A  E  G  G  T  W  D  S  W  G  Q  G  T  Q  V  T  V  S  S  Q  V  Q  L  Q  E  S
                           1->     CDR III     <-1
```

FIG. 27A

IR4618 (BIHEAD H14--R7)

```
GGGGGAGGATTGGTGCAGGCTGGGGACTCTCTGAGACTCTCCTGCGCGGGCCTCGGGGACGCACTTCTCATGGTATGGTGGCTATGGCATG
------+---------+---------+---------+---------+---------+---------+---------+---------+    450
CCCCCTCCTAACCACGTCCGACCCCCTGAGAGACTCTGAGAGGACGCGCCCGGAGCCCCTGCGTGAAGAGTACCATACCACCGATACCGTAC
 G  G  L  V  Q  A  G  D  S  L  R  L  S  C  A  A  S  G  R  T  S  H  G  Y  G  G  Y  G  M
                                              1->  CDR I

GGCTGGGTCCGCCAAATTCCAGGGAAGGAGCGTGAGCTTGTGCGCAGCAATTAGTGGTGGAGCGGTCGTAATACATACTATGCAGACTCCGTG
------+---------+---------+---------+---------+---------+---------+---------+---------+    540
CCGACCCAGGCGGTTTAAGGTCCCTTCCTCGCACTCGAACAGCGTCGTTAATCACTCCGCCAGCATTATGTATGATACGTCGTTAATCACCAC
 G  W  F  R  Q  I  P  G  K  E  R  E  L  V  A  A  I  R  W  S  G  R  N  T  Y  Y  A  D  S  V
                                                 1->                         CDR II
                                                                                       EagI

AAGGGCCGATTCACCATCTCCAGAGACAACGTCAAGGACATGCTGTATCTGCAAATGAACAGTTTGAAACCTGAGGACACGGCCGTTTAC
------+---------+---------+---------+---------+---------+---------+---------+---------+    630
TTCCCGGCTAAGTGGTAGAGGTCTCTGTTGCAGTTCCTGTACGACATAGACGTTTACTTGTCAAACTTTGGACTCCTGTGCCGGCAAATG
 K  G  R  F  T  I  S  R  D  N  V  K  D  M  L  Y  L  Q  M  N  S  L  K  P  E  D  T  A  V  Y
<-1
                                                                          BstEII
ACTTGTGCAGTTCGGACGGTTCGCAGGTCCGCGGTGGTTGACATTTCCAGTCCGGTTGGGTTTGCCTACTGGGGCCAGGGGACCCAGGTCACC
------+---------+---------+---------+---------+---------+---------+---------+---------+    714
TGAACACGTCAAGCCTGCCAAGCGTCCAGGCGCCACCAACTGTAAAGGTCAGGCGCCAACCCAAACGGATGACCCGGTCCCCTGGGTCCAGTGG
 T  C  A  V  R  T  V  R  V  V  D  I  S  S  P  V  G  F  A  Y  W  G  Q  G  T  Q  V  T
1->        CDR III                                          <-1
```

FIG. 27B

MULTIVALENT ANTIGEN-BINDING PROTEINS

CROSS-REFERENCE TO RELATED APPLICATIONS

This application is a national phase application of PCT/EP98/06991, filed Oct. 27, 1998.

FIELD OF THE INVENTION

The present invention relates to multivalent and multi-specific antigen binding proteins, methods for their production and uses thereof. In particular, the invention relates to antigen binding proteins comprising a polypeptide comprising in series two or more single domain binding units which are preferably variable domains of a heavy chain derived from an immunoglobulin naturally devoid of light chains.

BACKGROUND OF THE INVENTION

Antibodies are protein molecules belonging to a group of immunoglobulins generated by the immune system in response to an antigen. The structure of most antibody molecules is based on a unit comprising four polypeptides, two identical heavy chains and two identical light chains, which are covalently linked together by disulphide bonds. Each of these chains is folded in discrete domains. The C-terminal regions of both heavy and light chains are conserved in sequence and are called the constant regions, comprising one or more so-called C-domains. The N-terminal regions of the heavy and light chains, also known as V-domains, are variable in sequence and determine the specificity of the antibody. The regions in the variable domains of the light and heavy chains ($V_L$ and $V_H$ respectively) responsible for antigen binding activity are known as the hypervariable or complementarity determining regions (CDR).

Natural antibodies generally have at least two identical antigen-binding sites defined by the association of the heavy and light chain variable regions. Individual heavy or light chain domains having the capability to bind antigens have been described in the literature (Ward et al, Nature 341 (1989), 544–546) although generally most naturally occurring antibodies need both a $V_H$ and $V_L$ to form a complete antigen binding site and retain full immunoreactivity.

More recently, immunoglobulins capable of exhibiting the functional properties of the four-chain immunoglobulins described above but which comprise two heavy polypeptide chains and which furthermore are devoid of light polypeptide chains have been described (see European Patent Application EP-A-0584421, Casterman et al, 1994). Methods for the preparation of such antibodies or fragments thereof on a large scale comprising transforming a mould or yeast with an expressible DNA sequence encoding the antibody or fragment are described in patent application WO 94/25591 (Unilever).

The immunoglobulins described in EP-A-0584421, which may be isolated from the serum of Camelids, do not rely upon the association of heavy and light chain variable domains for the formation of the antigen-binding site but instead the heavy polypeptide chains alone naturally form the complete antigen binding site. These immunoglobulins, hereinafter referred to as "heavy-chain immunoglobulins" are thus quite distinct from the heavy chains obtained by the degradation of common (four-chain) immunoglobulins or by direct cloning which contribute part only of the antigen-binding site and require a light chain partner for antigen-binding, thus forming a complete antigen binding site.

As described in EP-A-0584421, heavy chain immunoglobulin $V_H$ regions isolated from Camelids (forming a complete antigen binding site and thus constituting a single domain binding site) differ from the $V_H$ regions derived from conventional four-chain immunoglobulins in a number of respects, notably in that they have no requirement for special features for facilitating interaction with corresponding light chain domains. Thus, whereas in common (four-chain) immunoglobulins the amino acid residues at the positions involved in the $V_H/V_L$ interaction is highly conserved and generally apolar leucine, in Camelid derived $V_H$ domains this is replaced by a charged amino acid, generally arginine. It is thought that the presence of charged amino acids at this position contributes to increasing the solubility of the camelid derived $V_H$. A further difference which has been noted is that one of the CDRs of the heavy chain immunoglobulins of EP-A-0584421, the $CDR_3$, may contain an additional cysteine residue associated with a further additional cysteine residue elsewhere in the variable domain. It has been suggested that the establishment of a disulphide bond between the $CDR_3$ and the remaining regions of the variable domain could be important in binding antigens and may compensate for the absence of light chains.

In the search for multivalent and multispecific antigen binding proteins, attention has been directed towards the use of fragments, or portions, of a whole antibody which can nevertheless exhibit antigen binding activity. By comparison with the whole antibody, the smaller antibody fragment is advantageous for use in therapy, for example, as it is likely to be less immunogenic and more able to penetrate tissue.

Binding fragments of common (four-chain) antibodies which have been considered include Fab (light chain associated with the $V_H$ and $C_{H1}$ domains of a heavy chain), $F_V$ (comprising of the V-domains of the heavy and light chains associated with each other) and ScFv (comprising a $V_H$ domain linked to a $V_L$ domain by a flexible peptide linker) fragments. These fragments have only one site for antigen binding compared to the two or more sites contained in the whole antibody, however, and in an attempt to overcome this problem, recombinant fragments having two or more binding sites have been proposed.

In general, those multivalent and/or multispecific constructions which have been described in the literature either comprise two or more polypeptide chains, see for example, patent application WO 94/09131 (Scotgen Limited) and WO 97/14719 (Unilever) or are based on a 'double ScFv' approach, wherein the multivalency arises when two or more monovalent ScFv molecules are linked together, providing a single chain molecule comprising at least four variable domains, as described, for example, in WO 93/11161 (Enzon Inc) and WO 94/13806 (Dow Chemical Co). In all of these cases, the binding site is formed through the association of light and heavy chain variable domains. In WO 93/11161, reference is made to a single-chain protein comprising the binding portions of the variable regions of an antibody light (or heavy) chain but it is stated that as such proteins are comprised of two similar variable regions, they do not necessarily have any antigen-binding capability.

EP-A-0584421 (Casterman), referred to above, discloses fragments of heavy chain immunoglobulins devoid of light chains, including fragments corresponding to isolated $V_H$ domains or to $V_H$ dimers linked by the hinge disulphide. Further disclosed, but not exemplified, are antibodies having different specificities on each heavy polypeptide chain which could be prepared by combining two heavy chain immunoglobulins or one heavy chain of an immunoglobulin of EP-A-0584421 with a fragment of a conventional four-chain immunoglobulin. There is no suggestion that multivalent and/or multispecific constructs may be prepared by joining together individual $V_H$ domains. Indeed, in the absence of the inherent conformational constraints conferred on the position of the binding sites by the presence of a corresponding light chain, it might generally be expected that the binding domains in constructs of this type would sterically hinder each other, unfavourably influencing binding activity.

SUMMARY OF THE INVENTION

In a first aspect, the invention provides a multivalent antigen binding protein comprising a single polypeptide chain comprising, connected in series, two or more single domain binding units.

In another aspect, the invention provides nucleotide sequences coding for multivalent antigen binding proteins according to the invention and cloning and expression vectors comprising such nucleotide sequences. Further provided are host cells transformed with vectors comprising such nucleotide sequences and methods of producing antigen binding proteins according to the invention by expression of the nucleotide sequences in such hosts.

The invention also provides compositions comprising multivalent antigen binding proteins according to the invention.

In a further aspect, the invention provides the use of multivalent antigen binding proteins as set forth above in diagnosis or therapy or in other methods for which antibodies or fragments thereof can be used, such as in immunoassay or purification methods. Methods of treatment using the multivalent antigen binding proteins according to the invention are also provided.

In a particular embodiment of the invention, there is provided the use of said multivalent antigen binding proteins in inactivating (bacterio)phages.

By means of the invention, antigen binding proteins having the specificity and binding affinity of the whole immunoglobulin but which have the additional advantage of smaller size are obtained. Furthermore, where the multivalent antigen binding proteins of the present invention comprise variable domains having different antigen specificity, multispecific binding molecules may be obtained. Another advantage is that the constructs according to the invention may conveniently be produced at high yields economically and efficiently on a scale appropriate for industrial use.

The present invention may be more fully understood with reference to the following description, when read together with the accompanying drawings. For convenience, an antigen binding protein according to the invention comprising two single binding units is herein referred to as a 'bihead'.

BRIEF DESCRIPTION OF THE DRAWINGS

FIG. 2 shows the nucleotide sequence of the PstI-BstEII insert of plasmid pUR4638, encoding the heavy chain variable domain of an anti-RR6 antibody (denoted R7) from a llama.

FIG. 3 shows the nucleotide sequence of the PstI-BstEII insert of plasmid pUR4640, encoding the heavy chain variable domain of another anti-RR6 antibody (denoted R9) from a llama.

FIG. 4 shows the nucleotide sequence of the PstI-BstEII insert of plasmid pUR4601, encoding the heavy chain variable domain of an anti-hCG antibody (denoted H14) from a llama.

FIG. 5 shows the nucleotide sequence of the PstI-BstEII insert of plasmid pUR4602, encoding the heavy chain variable domain or another anti-hCG antibody (denoted HI-15) form a llama.

FIG. 6 shows the nucleotide sequence of the PstI-BstEII insert of plasmid pUR4603, encoding the heavy chain variable domain of an anti-Streptococcus antibody (denoted S36) from a llama.

FIG. 7 shows the nucleotide sequence of the PstI-BstEII insert of plasmid pUR4642, encoding the heavy chain variable domain of another anti-Streptococcus antibody (denoted S120) from a llama.

FIG. 9 shows the nucleotide sequence within plasmid pUR4619, which encodes an anti-hCG-anti-RR6 bispecific biheaded antigen binding protein (denoted H14-R9), missing the first 4 and last 3 amino acids.

FIG. 10 shows the nucleotide sequence within plasmid pUR4620, which encodes an anti-hCG-anti-RR6 bispecific biheaded antigen binding protein (denoted HI15-R7), missing the first 4 and last 3 amino acids.

FIG. 11 shows the nucleotide sequence within plasmid pUR4621, which encodes an anti-hCG-anti-RR6 bispecific biheaded antigen binding protein (denoted HI15-R9), missing the first 4 and last 3 amino acids.

FIG. 12 shows the nucleotide sequence within plasmid pUR4622, which encodes a homodimeric bivalent anti-RR6 antigen binding protein (denoted R7—R7), missing the first 4 and last 3 amino acids.

FIG. 13 shows the nucleotide sequence within plasmid pUR4623, which encodes a heterodimeric bivalent anti-RR6 antigen binding protein (denoted R7-R9).

FIG. 18 shows the binding activity and SDS-PAGE analysis of crude *H. polymorpha* supernatants expressing the constructs of Example 5.

FIG. 27 shows the nucleotide sequence within plasmid pUR4618 which encodes an anti-hcg anti-RR6 bispecific biheaded antigen binding protein (denoted H14-R7, missing the first 4 and last 3 amino acids.

DETAILED DESCRIPTION OF THE INVENTION

Figure 1:
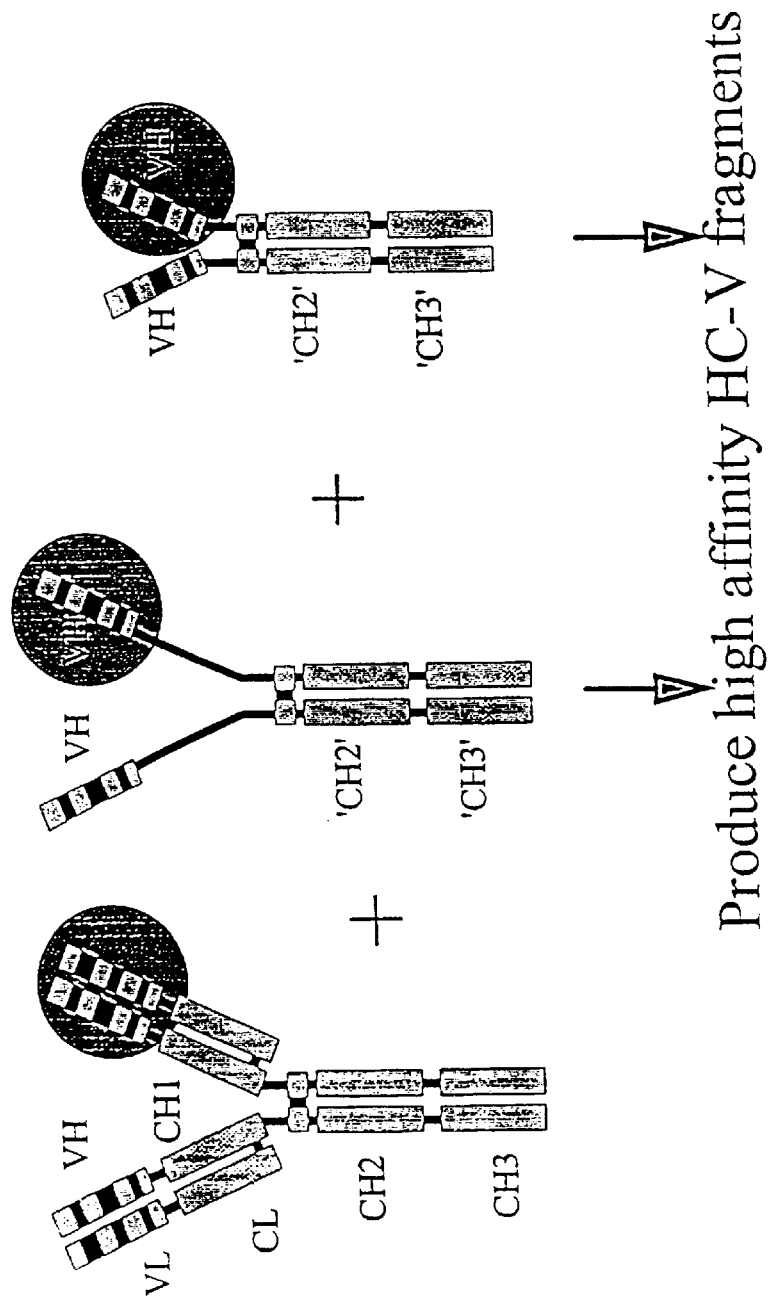
FIG. 1 shows a schematic representation of Camelidae IgG types.

The invention is based on the finding that the variable domains of a heavy chain derived from an immunoglobulin naturally devoid of light chains may be joined together to form a multivalent single polypeptide which retains the antigen binding affinity of the parent whole immunoglobulin but which is much smaller in size and therefore less immunogenic, thereby providing important benefits over the use of whole antibody molecules, particularly, for example, in the area of diagnostics, therapy and targeting. Accordingly, the invention as described herein is directed to multivalent forms of antigen binding proteins, methods for preparing them and new and improved methods for their use.

As used herein, a multivalent antigen binding protein is a protein which has more than one antigen binding site.

Included within this are bivalent, trivalent, tetravalent and so on. According to one aspect, bivalent forms, that is forms having two antigen-binding sites, are preferred but it will be appreciated that higher multivalent forms may find application in certain circumstances.

A single domain binding unit means an immunoglobulin variable domain which naturally forms a complete antigen binding site.

The single domain binding units for use according to the present invention are preferably heavy chain variable domains derived from any immunoglobulin naturally devoid of light chains, such that the antigen-binding site is located exclusively in the heavy chain variable domain. Preferably, the heavy chain variable domains for use in the invention are derived from immunoglobulins naturally devoid of light chains such as may be obtained from camelids as described in EP-A-0584421, discussed above.

Where the individual single domain binding units which are joined together to form the multivalent antigen binding proteins of the invention have the same antigen specificity, a binding protein which binds more than one molecule of the same type will be produced. Alternatively, multivalent and multispecific binding proteins according to the invention which are able to bind different epitopes from each other may be obtained by assembling together single domain binding units directed against different antigens. Heavy chain variable domains derived from an immunoglobulin naturally devoid of light chains having a determined antigen specificity may conveniently be obtained by screening expression libraries of cloned fragments of genes encoding camelid immunoglobulins generated using conventional techniques, as described, for example, in EP-A-0584421 and Example 1.

The multivalent antigen-binding proteins of the invention may be formed by linking together the single domain binding units in series, such that each single domain binding unit is linked to at least one other variable domain.

The individual single domain binding unit may be linked sequentially by means of peptide linkers, conveniently flexible peptide linkers which allow the domains to flex in relation to each other such that simultaneous binding to multiple antigenic determinants may be achieved. It will be appreciated that the binding of the linker to the individual single domain binding unit will be such that it does not affect the binding capacity of the single domain antigen binding site. Any peptide linker which permits the single domain binding units components to be linked in such a way that each variable domain retains the binding specificity of the whole immunoglobulin from which it is derived may suitably be used. Such linkers include, e.g., peptides derived from known proteins, such as glucoamylase, cellobiohydrolase, or cell wall proteins (CWP), or synthetic peptides which are rationally designed. The linker may suitably comprise from 1 to 400 or more amino acid residues; conveniently, the peptide linker comprises from 5 to 20 amino acid residues. This group of antigen binding proteins according to the invention with such a linker between the two single domain binding units is usually preferred because of its good production yields.

In another preferred embodiment of the invention, the individual single domain binding units may be connected directly in series without any intervening linker. In this way, the binding sites in the multivalent binding proteins according to the invention are held in much closer proximity to each other than would be the case in the whole immunoglobulin from which the immunoglobulin fragments are derived. It might generally be expected that this would give rise to unfavourable steric interactions, but surprisingly, full binding activity is found to be retained. Furthermore, these fragments with directly linked single domain binding units appear to be more stable, e.g. towards proteolytic degradation.

In an alternative embodiment, functional groups such as enzymes may be fused to the antigen binding protein.

The multivalent antigen binding proteins according to the invention may suitably find application in a wide variety of uses for which antibodies, or fragments thereof, have been proposed in the art. These uses include diagnosis, therapy, targeting, immunoassays, in agglutination, agglutination assays and purification processes, and detergents.

For use in diagnosis or therapy targeting, antigen binding proteins according to the invention having binding activity directed against both target site and the diagnostic or therapeutic agent may be constructed. Multivalent binding proteins having two or more distinct binding specificities are of particular use, for example, in the targeted delivery of therapeutic agents to their intended site of action. The binding proteins according to the invention establish the connection between therapeutic agent and target site by self-assembly, thereby avoiding the need for chemical conjugation reactions, and the therapeutic agent is guided to the target, giving increased local efficiency. Cytotoxic agents may be targeted directly to the tumour cell to be attacked, for example, by means of a bispecific, bivalent binding protein according to the invention having specificity for both the cell and the cytotoxic agent. Enzymes which are capable of generating a cytotoxic product at a target site, particularly oxido-reductases such as glucose oxidase (which catalyses the oxidation of glucose to gluconic acid, thereby producing hydrogen peroxide which exhibits cell toxicity) similarly can conveniently be delivered to the intended site of action using a binding protein according to the invention having both anti-target and anti-enzyme specificity.

Alternatively, the antigen binding proteins according to the invention may conveniently be attached to one or more appropriate diagnostically or therapeutically effective agents or carriers by methods conventional in the art.

Direct attachment of the diagnostically or therapeutically effective agent to the small antigen binding proteins of the invention runs the risk that the binding activity will be adversely affected through steric hindrance of the binding site. In a particular embodiment, therefore, the antigen binding protein has an additional polypeptide group appended to it, which additional polypeptide group does not contribute to the binding properties but which provides a "handle" for the attachment of the diagnostic or therapeutic agent.

Such antigen binding proteins with an attached polypeptide also find particular application in immunoadsorption processes, especially immunoaffinity purification processes which require that the binding protein be linked to another material, for example a label, such as an enzyme, or a solid phase, for example, a carrier material in a column.

The additional peptide group is generally attached to the antigen binding protein at or near one end of its polypeptide chain through a peptide bond, such that this polypeptide chain is prolonged by the additional peptide which now forms the terminal portion of the chain. Conveniently, the additional peptide group will be attached at its amino terminus. Suitable additional peptide linking groups and methods for their attachment are described in WO 91/08492 (Unilever). Conveniently, they comprise at least 5 but preferably not more than 20 amino acid residues and preferably include at least one lysine residue as this provides a convenient site for covalent attachment onto surfaces or proteinaceous tracers such as enzymes. A particularly suitable additional peptide linking group, particularly for coupling the antigen binding protein to a solid plastics surface, comprises the "Myc" amino acid sequence:
GLU-GLN-LYS-LEU-ILE-SER-GLU-GLU-ASP-LEU-ASN. (see SEQ ID. NO: 1)

Coupling of the additional peptide to a solid surface such as latex particles and other structures formed from plastics material commonly used in immunoassays may conveniently be achieved by means of conventional chemical cross-linking agents. It will be appreciated that the chemical coupling site in the additional peptide should preferably be sufficiently remote from the variable domain binding sites such that the coupled molecule does not affect binding activity. Alternatively, therapeutic agents and tracers such as enzymes (for example horse radish peroxidase, alkaline phosphatase, glucose oxidase) may be covalently coupled to the additional peptide via the E-amino (epsilon)group of the lysine group.

Multivalent, multispecific binding proteins according to the invention may be used to particular advantage in adsorption and purification techniques by value of their ability to exhibit specificity for two or more distinct materials. The detection and purification of ligands may conveniently be achieved using surfaces activated with constructs according to the invention. By way of illustration, a suitable support incorporating molecules for which a binding protein according to the invention has binding specificity can be activated or sensitised by coating it with a bispecific binding protein of appropriate binding specificity, the remaining binding specificity being free to bind with analyte or contaminant as appropriate depending on the intended use. Suitable molecules which can be incorporated into the support, either by adsorption or covalent bonding, include proteins, peptides, carbohydrates, DNA, RNA or conjugates thereof. Particularly preferred ligands which may be detected or purified in this way include human chorionic gonadotrophin, luteinising hormone, estrone, progesterone or metabolites thereof. The support may be particulate, planar or porous in nature. Suitable supports include those conventionally used in immuno-adsorption and purification techniques, particularly latex particles, polystyrene wells and dextran surfaces.

In an alternative aspect, binding proteins according to the invention may be used as cross-linking reagents. For example, a bispecific binding protein can link one phage to another, thereby leading to their inactivation. Inactivation of viruses or microorganisms may similarly be accomplished through agglutination.

In a further embodiment of the invention, binding proteins may be used in detergent compositions, and the like, for the treatment of stains essentially as described in PCT/EP 98/03438. Thus, for example, a bispecific protein according to the invention can have high binding affinity for stain as one specificity and for enzyme as another one. Such a bispecific protein could fulfil the requirement of accumulating enzyme on stain either by supplying said protein together with enzyme as a pre-formed non-covalent complex or by supplying the two separately and allowing them to self-assemble either in the wash liquor or on the stain. A further important aspect is to use a binding protein that binds to several different, but structurally-related, molecules in a class of "stain substances". This would have the advantage of enabling a single enzyme species to bind (and bleach) several different stains. An example would be to use a binding protein which binds to the polyphenols in wine, tea, and blackberry.

Multivalent antigen binding proteins according to the invention may be prepared by transforming a host by incorporating a gene encoding the polypeptide as set forth above and expressing said gene in said host.

Suitably the host or hosts may be selected from prokaryotic bacteria, such as Gram-negative bacteria, for example *E. coli*, and Gram-positive bacteria, for example *B. subtilis* or lactic acid bacteria, lower eukaryotes such as yeasts, for example belonging to the genera Saccharomyces, Kluyveromyces, Hansenula or Pichia, or moulds such as those belonging to the genera Aspergillus or Trichoderma.

Preferred hosts for use in connection with the present invention are the lower eukaryotic moulds and yeasts.

Techniques for synthesising genes, incorporating them into hosts and expressing genes in hosts are well known in the art and the skilled person would readily be able to put the invention into effect using common general knowledge.

Methods for producing antibody fragments or functionalised fragments thereof derived from the heavy chain immunoglobulin of Camelidae using a transformed lower eukaryotic host are described, for example in patent application WO 94/25591 and such techniques may suitably be applied to prepare constructs according to the present invention.

Proteins according to the invention may be recovered and purified using conventional techniques such as affinity chromatography, ion exchange chromatography or gel filtration chromatography.

The activity of the multivalent binding proteins according to the invention may conveniently be measured by standard techniques known in the art such as enzyme-linked immunoadsorbant assay (ELISA), radioimmune assay (RIA) or by using biosensors.

The following examples are provided by way of illustration only. Techniques used for the manipulation and analysis of nucleic acid materials were performed as described in Sambrook et al, Molecular Cloning, Cold Spring Harbor Press, New York:, 2nd Ed.(1989) unless otherwise indicated.

HC-V denotes heavy chain variable domain.
Restriction sites are underlined.

EXAMPLES

Example 1

Induction of Humeral Immune Responses in Llama

Male llamas were immunised with a water in oil emulsion (1:9 V/V, antigen in water: Specol (Bokhout et al.) subcutaneously and intramuscularly. Per immunisation site 0.75–1.5 ml water in oil emulsion was inoculated containing 100:g antigen. The antigens used were: hCG (Sigma), azo-dye RR6 (ICI) which was coupled to BSA via its reactive triazine group and *Streptococcus mutans* HG982 cells. Immunisations were performed according to the following time table: The second immunisation was performed three weeks after the first. The third was performed two weeks after the second immunisation. The immune response was followed by antigen specific ELISAs.

The anti-RR-6 response was measured by using Nunc Covalink plates, which where coated with the azo-dye. After incubation with (diluted) serum samples, the bound llama antibodies were detected via a incubation with poly-clonal rabbit-anti-llama antiserum (obtained via immunising rabbits with llama immunoglobulines which were purified via ProtA and ProtG columns; ID-DLO), followed by an incubation with swine-anti-rabbit immunoglobulines (Dako) conjugated with alkaline phosphatase. Finally the alkaline phosphatase enzyme-activity was determined after incubation with p-nitro-phenyl phosphate and the optical density was measured at 405 nm. The anti-hCG response, was measured in essentially the same way using Nunc maxi-sorb plates coated with hCG. The anti-Streptococcus response, was measured in essentially the same way using nunc maxi-sorb plates sensitised with *Streptococcus mutans* HG982.

Example 2

Cloning, Expressing and Screening of Llama EC-V Fragments 2.1 Isolation of Gene Fragments Encoding Llama HC-V Domains.

From an immunised llama a blood sample of about 200 ml was taken and an enriched lymphocyte population was obtained via Ficoll (Pharmacia) discontinuous gradient centrifugation. From these cells, total RNA was isolated by acid guanidium thiocyanate extraction (e.g. via the method described by Chomczynnski and Sacchi, 1987). After first strand cDNA synthesis (e.g. with the Amersham first strand cDNA kit), DNA fragments encoding HC-V fragments and part of the long or short hinge region were amplified by PCR using specific primers:

```
             PstI
V_H-2B    5'-AGGTSMARCTGCAGSAGTCWGG-3'            (see SEQ. ID. NO:2)
S = C and G, M = A and C, R = A and G, W = A and T, HindIII
Lam-07   5'-AACAGTTAAGCTTCCGCTTGCGGCCGCGGAGCTGGGGTCTTCGCTGTG    (see SEQ. ID. NO:3)
         GTGCC-3'
(short hinge)

HindIII
Lam-08   3'-AACAGTTAAGCTTCCGCTTGCGGCCGCTGGTTCTGGTTTTGGTGTCTT    (see SEQ. ID. NO:4)
         GGGTT-3'
(long hinge)
```

Upon digestion of the PCR fragments with PstI (coinciding with codon 4 and 5 of the HC-V domain, encoding the amino acids L–Q) and BstEII (located at the 3'-end of the HC-V gene fragments, coinciding with the amino acid sequence Q-V-T), the DNA fragments with a length between 300 and 400 bp (encoding the HC-V domain, but lacking the first three and the last three codons) were purified via gel electrophoresis and isolation from the agarose gel.

2.2 Construction of *Saccharomyces cerevisiae* Expression Plasmids Encoding Llama HC-V Domains.

Plasmids pUR4547 and pUR4548 are *Saccharomyces cerevisiae* episomal expression plasmids, derived from pSY1 (Harmsen et al., 1993). From pSY1 the PstI site, located in front of the GAL7 promoter was removed after partial digestion with PstI, incubation with Klenow fragment and subsequent blunt end ligation. After transformation the desired plasmid could be selected on the basis of restriction pattern analysis. Subsequently, the BstEII site in the Leu2 selection marker was removed by replacing the about 410 bp AflII/PflMI fragment with a corresponding fragment in which the BstEII site was removed via a three step PCR mutagenesis, using the primers:

```
                                                  (see SEQ. ID. NO:5)
PCR-A:

PflMI
BOLI 1 5'-GGGAATTCCAATAGGTGGTTAGCAATCG (see SEQ. ID. NO:6)
                (BstEII)
BOLI 4 5'-GACCAACGTGGTCGCCTGGCAAAACG (see SEQ. ID. NO:7)
PCR-B:

(BstEII)
BOLI 3 5'-CGTTTTGCCAGGCGACCACGTTGGTC (see SEQ. ID. NO:8)
                AflII
BOLI 2 5'-CCCCAAGCTTACATGGTCTTAAGTTGCCGT
```

PCR-A was performed with primers BOLI 1 and BOLI 4 and resulted in an about 130 bp fragment with the PflMI restriction site at the 3'-end and the inactivated BstEII site at the 5'-end. PCR-B was performed with primers BOLI 2 and BOLI 3 and resulted in an about 290 bp fragment with the AflII site at the 5'-end. The third PCR was with the fragments obtained from reaction A and B, together with the primers BOLI 1 and BOLI 2.

Finally, the about 1.8 kb SacI-HindIII fragment was replaced with synthetic fragments, having sequences as presented below, resulting the plasmids pUR4547 and pUR4548, respectively.

```
                                    (see SEQ. ID. NO:9 and NO:10)
SacI/HindIII fragment of pUR4547
─────────────────────────────

SacI
  GAGCTCATCACACAAACAAACAAAACAAAATGATGCTTTTGCAAGCCTTCCCTT
1 ---------+---------+---------+---------+---------+----  54
  CTCGAGTAGTGTGTTTGTTTGTTTTGTTTTACTACGAAAACGTTCGGAAGGGAA
                                  M  M  L  L  Q  A  F  L  F
                                  |→     SUC2 ss

PstI
   TTCCTTTTGGCTGGTTTTGCAGCCAAAATATCTGCGCAGGTGCAGCTGCAGG
55 ------+---------+---------+---------+---------+-----  105
   AAGGAAAACCGACCAAAACGTCGGTTTTATAGACGCGTCCACGTCGACGTCC
     L  L  A  G  F  A  A  K  I  S  A  Q  V  Q  L  Q  E
                                            |→

BstEII                  HindIII
    AGTCATAATGAGGGACCCAGGTCACCGTCTCCTCATAATGACTTAAGCTT
106 ----+---------+---------+---------+---------+-----   155
    TCAGTATTACTCCCTGGGTCCAGTGGCAGAGGAGTATTACTGAATTCGAA
      E  S  *  *  G  T  Q  V  T  V  S  S  *  *
         HC-V cassette                   ←|
    and (see SEQ. ID. NO:11 and NO:12)
SacI/HindIII fragment of pUR4548
─────────────────────────────

SacI
  GAGCTCATCACACAAACAAACAAAACAAAATGATGCTTTTGCAAGCCTTCCTTT
1 ---------+---------+---------+---------+---------+----  54
  CTCGAGTAGTGTGTTTGTTTGTTTTGTTTTACTACGAAAACGTTCGGAAGGAAA
                                  M  M  L  L  Q  A  F  L  F
                                  |→     SUC2 ss

PstI
   TCCTTTTGGCTGGTTTTGCAGCCAAAATATCTGCGCAGGTGCAGCTGCAGG
55 -----+---------+---------+---------+---------+-----  105
   AGGAAAACCGACCAAAACGTCGGTTTTATAGACGCGTCCACGTCGACGTCC
     L  L  A  G  F  A  A  K  I  S  A  Q  V  Q  L  Q  E
                                            |→

BstEII
    AGTCATAATGAGGGACCCAGGTCACCGTCTCCTCAGAACAAAAACTCATC
106 ----+---------+---------+---------+---------+-----   155
    TCAGTATTACTCCCTGGGTCCAGTGGCAGAGGAGTCTTGTTTTTGAGTAG
      S  *  *  G  T  Q  V  T  V  S  S  E  Q  K  L  I
    HC-V cassette                     ←|→     myc tail HindIII
    TCAGAAGAGGATCTGAATTAATGACTTAAGCTT
156 ----+---------+---------+--------                    188
    AGTCTTCTCCTAGACTTAATTACTGAATTCGAA
      S  E  E  D  L  N  *  *
                 ←|
```

Both plasmids contain the GAL7 promoter and PGK terminator sequences as well as the invertase (SUC2) signal sequence. In both plasmids the DNA sequence encoding the SUC2 signal sequence is followed by the first 5 codons, (encoding Q-V-Q-L-Q=SEQ. ID. NO: 13) of the HC-V domain (including the BstII site), a stuffer sequence, the last six codons (encoding Q-V-T-V-S-S=SEQ. ID. NO: 14) of the HC-V domain. In pUR4547, this is followed by two stop codons, an AflII and HindIII site. In pUR4548, this sequence is followed by eleven codons encoding the myc-tag, two stop codons, an AflII and HindIII site.

Plasmids pUR4547 and pUR4548 were deposited under the Budapest Treaty at the Centraal Bureau voor Schimmelcultures, Baarn on Aug. 18, 1997 with deposition numbers: CBS 100012 and CBS 100013, respectively. In accordance with Rule 28(4) EPC, or a similar arrangement from a state not being a contracting state of the EPC, it is hereby requested that a sample of such deposit, when requested, will be submitted to an expert only.

Upon digesting pUR4548 with PstI and BstEII, the about 6.4 kb vector fragment was isolated and ligated with the PstI-BstEII fragments of about 350 bp obtained as described above. After transformation of *S. cerevisiae*, via electroporation, transformants were selected from minimal medium agar plates (comprising 0.7% yeast nitrogen base, 2% glucose and 2% agar, supplemented with the essential amino acids and bases).

2.3 Screening for Antigen Specific HC-V Domains.

For the production of llama HC-V fragments with myc-tail, individual transformants were grown overnight in selective minimal medium (comprising 0.7% yeast nitrogen base, 2% glucose, supplemented with the essential amino acids and bases) and subsequently diluted ten times in YPGal medium (comprising 1% yeast extract, 2% bacto pepton and 5% galactose). After 24 and 48 hours of growth, the culture supernatant of the colonies was analysed by ELISA for the presence of HC-V fragments which specifically bind to the antigens hCG, RR6 or Streptococcus in essential the same way as described in Example 1. In this case, however, the presence of specifically bound HC-V fragments was detected by incubation with monoclonal anti-myc antibodies, followed by incubation with poly-clonal rabbit-anti-mouse conjugate with alkaline phosphatase. In this way a number of anti-hCG, anti-Streptococcus and anti-RR6 HC-V fragments have been isolated, among which are:

| anti-RR6: | | |
|---|---|---|
| R7 | pUR4638 | (see FIG. 2; SEQ. ID. NO: 15 and NO: 16) |
| R9 | pUR4640 | (see FIG. 3; SEQ. ID. NO: 17 and NO: 18) |
| anti-hCG (alpha unit): | | |
| HI4 | pUR4601 | (see FIG. 4; SEQ. ID. NO: 19 and NO: 20) |
| HI15 | pUR4602 | (see FIG. 5; SEQ. ID. NO: 21 and NO: 22) |
| anti-*Streptococcus*: | | |
| S36 | pUR4603 | (see FIG. 6; SEQ. ID. NO: 23 and NO: 24) |
| S120 | pUR4642 | (see FIG. 7; SEQ. ID. NO: 25 and NO: 26) |

```
MPG158WB                                      (see SEQ. ID. NO:27)
                      XhoI
5'-GAATTAAGCGGCCGCCCAGGTGAAACTGCTCGAGTCWGGGGGA-3' and

MPG159WB                                      (see SEQ. ID. NO:28)
             BstEII
3'-CCCTGGGTCCAGTGGCAGAGGAGTGGCAGAGGAGTCTTGTTT-5'
```

In this way the sequence:

```
                        (see SEQ. ID. NO:29 and NO:30)
           PstI
CAG GTC CAG CTG CAG GAG TCT GGG
 Q   V   Q   L   Q   E   S   G became (see SEQ. ID. NO:31 and NO:32)
           XhoI
GAG GTG AAA CTG CTC GAG TCW GGG
 Q   V   K   L   L   E   S   G
```

Upon digesting the PCR fragments with XhoI and BstEII, the about 330 bp fragments were purified via agarose gel electrophoresis and isolation from the gel. The fragments were cloned into pUR4421 (see Example 1 in WO 94/25591) which was digested with the same enzymes, resulting in pJS2 (HI4) and pJS3 (HI15). Subsequently, the about 420 bp EagI-HindIII fragments of pJS2 and pJS3 were isolated and ligated in the about 6.6 kb EagI-HindIII vector fragment of the pSY1 plasmid of which the PstI and BstEII sites were removed as described in Example 2.2. The resulting plasmids pJS7 and pJS8, respectively, were digested with BstEII and HindIII, after which the purified vector fragment was religated in the presence of a synthetic linker having the following sequence:

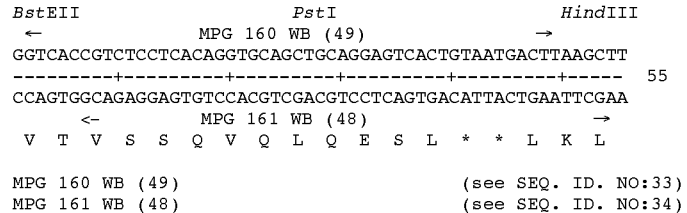

```
MPG 160 WB (49)                              (see SEQ. ID. NO:33)
MPG 161 WB (48)                              (see SEQ. ID. NO:34)
```

Example 3

Production of Llama HC-V Biheads by *S. cerevisiae*

3.1 Construction of Episomal Expression Plasmids Encoding Anti-hCG/Anti-RR6 bispecific Biheads.

Figure 8:
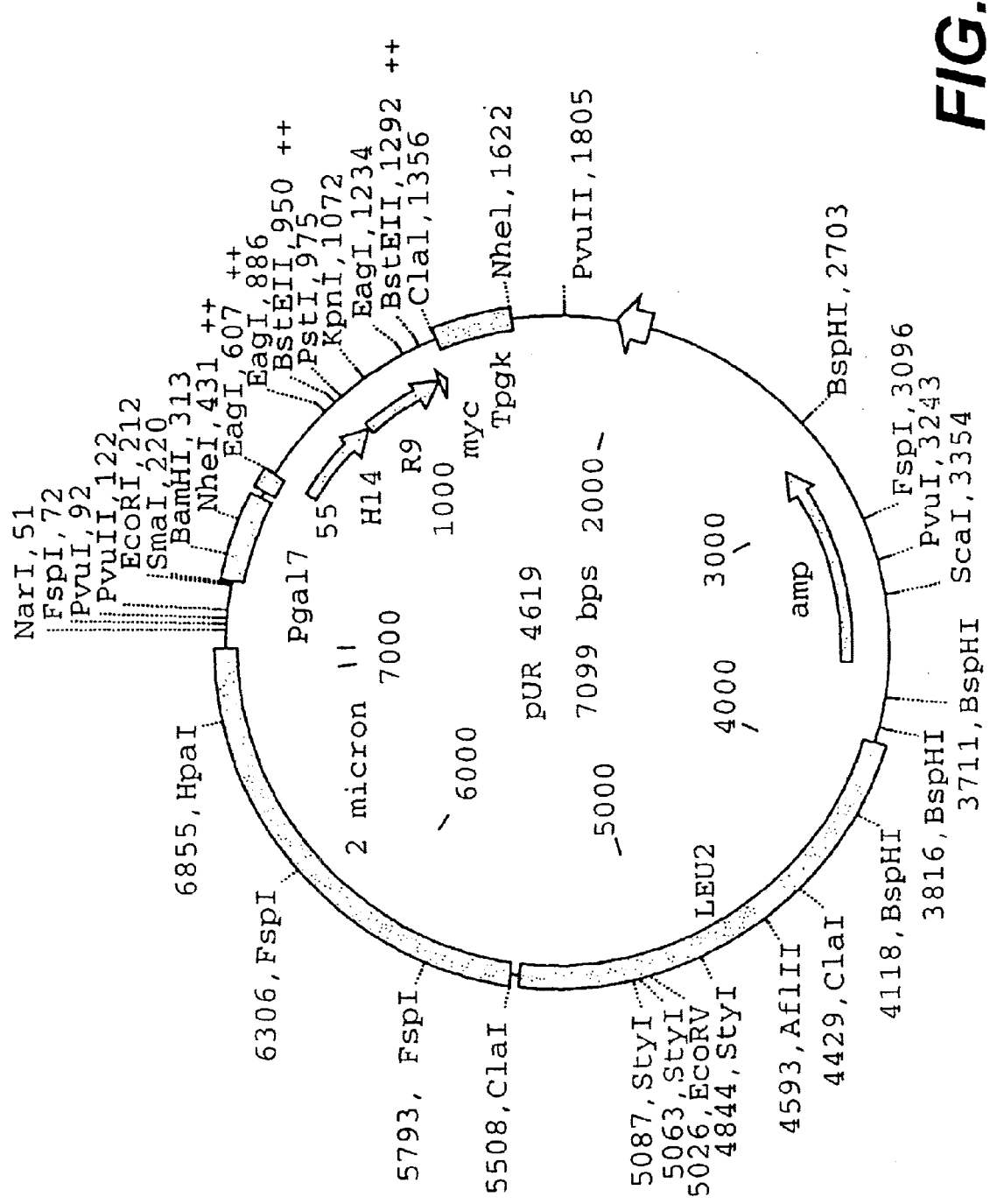
FIG. 8 shows a map of plasmid pUR4619.

In the anti-hCG HC-V fragments HI4 and HI15 (anti-alpha-subunit), the PstI site was removed and a XhoI site was introduced via PCR, using the primers:

resulting in plasmids pJS9 and pJS1O. Finally, these plasmids were digested with PstI and HindIII, after which 35 the purified vector fragments of about 7.0 kb were ligated with the PstI-HindIII fragments of about 350 bp of pUR4638 and pUR4640, encoding the anti-RR6 HC-V fragments R7 and R9, respectively, followed by the myc-ta-1. The resulting *S. cerevisiae* episomal expression plasmids pUR4618, pUR4619, pUR4620 and pUR4621 encode a anti-hCG-anti-RR6 bispecific bihead preceded by the SUC2 signal sequence and followed by the myc-tail.

pUR4618:  SUC2 - H14 - R7 - myc   (see FIG. 27; SEQ. ID. NO: 35 and NO: 36)

pUR4619:  SUC2 - H14 - R9 - myc   (see FIG. 8–9; SEQ. ID. NO: 37 and NO: 38)

pUR4620:  SUC2 - HI15 - R7 - myc  (see FIG. 10; SEQ. ID. NO: 39 and NO: 40)

pUR4621:  SUC2 - HI15 - R9 - myc  (see FIG. 11; SEQ. ID. NO: 41 and NO: 42)

Upon digesting these plasmids with XhoI and partially with BstEII, XhoI-BstEII fragments of about 0.7 kb can be isolated and subsequently cloned into the vector fragment of pUR4547 (digested with the same enzymes). In this way biheads can be obtained without the myc tail.

It will be appreciated that expression vectors can be constructed in which different promoter systems, e.g. the constitutive GAPDH promoter or different signal sequences, e.g. the mating factor prepro sequence are used.

3.2 Construction of Episomal Expression Plasmids Encoding Anti-RR6 Bivalent Biheads.

Upon digesting plasmids pUR4618 and pUR4619 with BstEII (partially) and HindIII, DNA fragments of about ~440 and ~400 bp could be purified, respectively. These fragments were subsequently ligated with the BstEII-HindIII vector fragment (~6.7 kb) of pUR4638 resulting in pUR4622 and pUR4623 (see FIGS. 12–13; SEQ. ID. NOS: 43/44 and 45/46, respectively), encoding a homodimeric bivalent and a heterodimeric bivalent bihead, respectively.

pUR4622:     SUC2 - R7 - R7 - myc pUR4623:     SUC2 - R7 - R9 - myc 3.3 Production and Analysis of the HC-V Biheads.

After introducing the expression plasmids pUR4618 through pUR4623 into *S. cerevisiae* via electroporation, transformants were selected from minimal medium agar plates as described in Example 2.3. For the production of biheads, the transformants were grown overnight in selective minimal medium and subsequently diluted ten times in YPGal medium. After 24 and 48 hours of growth, samples were taken for Western blot analysis. For the immuno detection of the produced biheads via Western blot analysis, monoclonal anti-myc antibodies were used, followed by incubation with poly-clonal rabbit-anti-mouse conjugate with alkaline phosphatase.

Figure 14:
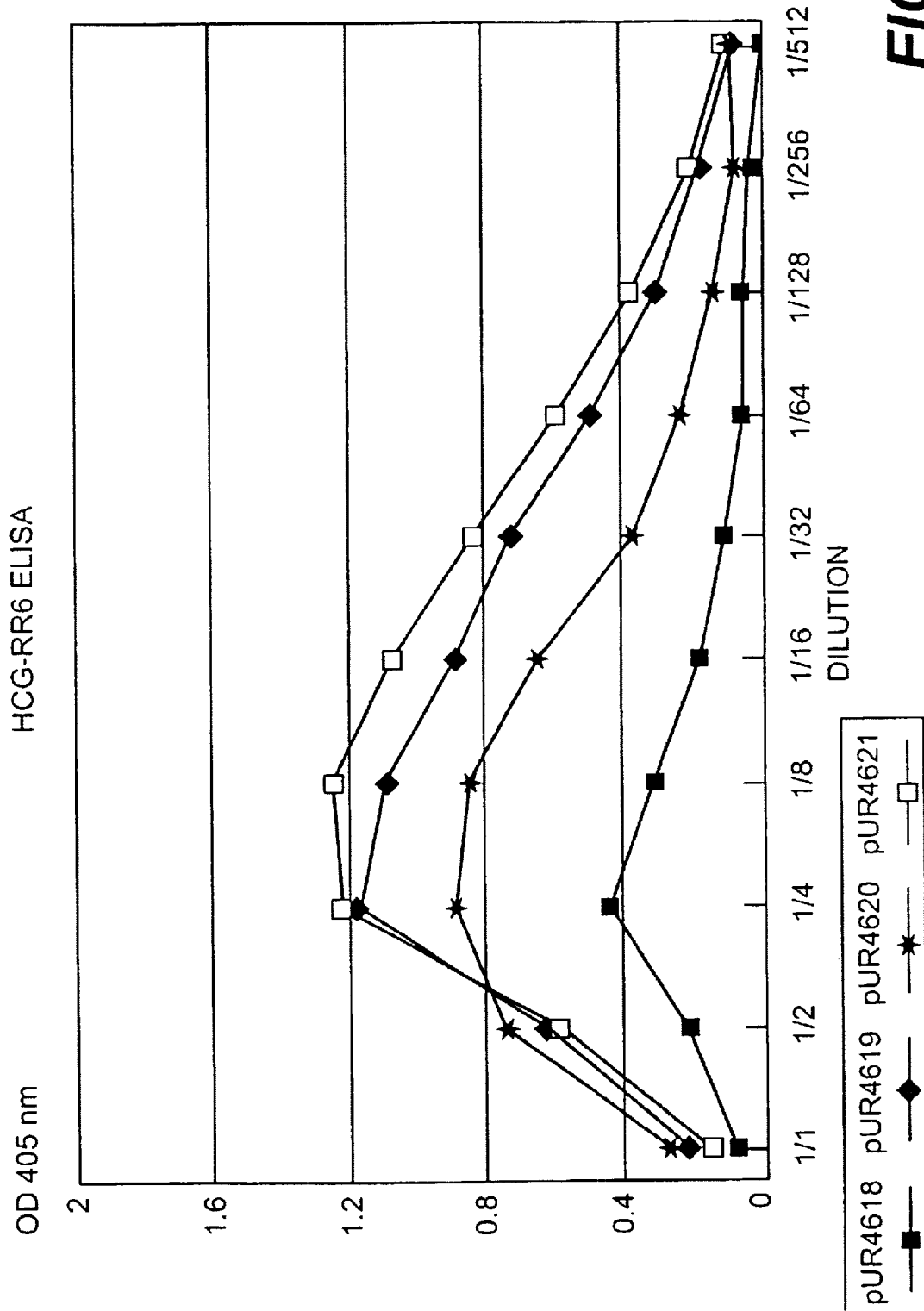
FIG. 14 shows the results of an hCG/RR-6 bispecific binding assay.

Bi-Functionality of the Bispecific Biheads was Tested as Follows:

PINs coated with hCG were incubated with (diluted) medium samples. Subsequently, the PINs were incubated with a RR6-alkaline phosphatase conjugate, in which the azo-dye RR6 was coupled to the alkaline phosphatase via its reactive triazine group. Finally the alkaline phosphatase enzyme-activity was determined after incubation of the PINs with p-nitro-phenyl phosphate and the optical density was measured at 405 nm (see FIG. 14).

Figure 15:
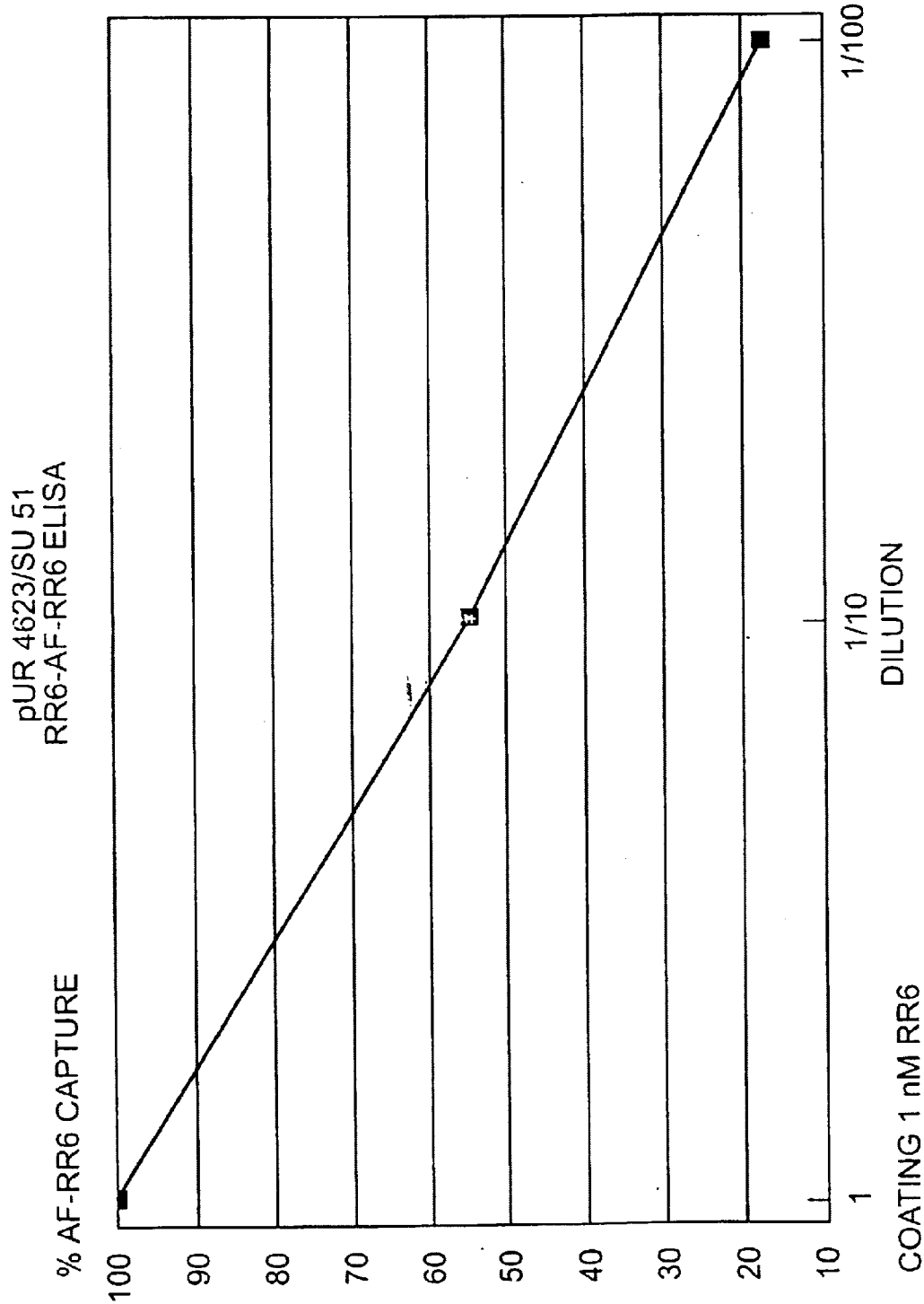
FIG. 15 shows the results of a RR6/RR6 bifunctional binding assay.

Bi-Functionality of the Mono-Specific, Bivalent Biheads was Tested as Follows:

Nunc Covalink plates, coated with RR6 were incubated with (diluted) medium samples. Subsequently, they were incubated with a RR6-alkaline phosphatase conjugate, in which the azo-dye RR6 was coupled to the alkaline phospathase via its reactive triazine group. Finally the alkaline phosphatase enzyme-activity was determined after incubation with p-nitro-phenyl phosphate and the optical density was measured at 405 nm (see FIG. 15).

Example 4

Production of HC-V Biheads by *P. pastoris*

4.1 Construction of Integration Vectors for the Expression of Anti-hCG/Anti-RR6 Bispecific Biheads.

To allow the expression and secretion of the Llama bihead constructs in *P. pastoris*, the gene encoding the bispecific construct was fused to the alpha-mating factor leader sequence in the commercially available *P. pastoris* expression vector pPIC9 (Invitrogen). The construction of the final expression vectors involved several cloning steps.

Step 1:

The construction of the bispecific HCV expression vectors required the construction of two shuttle vectors, pPIC9N and pUC.HCVx2. For pUC.HCVx2 the HindIII/EcoRI polylinker of pUC19 was replaced with a synthetic HindIII/EcoRI fragment, destroying the original HindIII site, introducing a NheI site which allows the direct fusion to the alpha-Mating Factor leader sequence in pPIC9N, and introducing the XhoI and HindIII HCVx2 insertion sites.

Synthetic Insert of pUC.HCVx2:

```
                                   (see SEQ. ID. NO:47 and NO:48)
    ----A  S  Q  V  K  L  L  E-----
AAGCTGCTAGCCAGGTGAAACTGCTCGAGCCCGGGAAGCTTGAATTC
    NheI              XhoI        HindIII
```

The synthetic linker was constructed by annealing the synthetic oligonucleotides PCR.650 and PCR.651.

PCR.650:  5'-AGCTGCTAGCCAGGTGAAACTGCTCGAGCCCGGGAAGCTTG-3'   (see SEQ. ID. NO: 49)

PCR.651:  5'-AATTCAAGCTTCCCGGGCTCGAGCAGTTTCACCTGGCTAGC-3'   (see SEQ. ID. NO: 50)

The XhoI/HindIII gene fragments encoding the bispecific HCV fragments were excised from pUR4619 and pUR4621 (see Example 3.1) and inserted into the XhoI/HindIII opened pUC.HCVx2 shuttle vector, thus yielding the intermediate constructs pUC.HCV.19 and pUC.HCV21. For pPIC9N the XhoI/EcoRI polylinker of pPIC9 (Invitrogen) was replaced with a synthetic XhoI/EcoRI fragment which introduces a NheI restriction site immediately downstream of the alpha-Mating Factor leader sequence.

```
                                (see SEQ. ID. NO:51 and NO:52)
  L  E  K  R  A  S
CTCGAGAAAAGAGCTAGCCCCGGGGAATTC
  XhoI       NheI       EcoRI
```

The new insert was constructed by annealing the synthetic oligonucleotides PCR.648 and PCR.649.

PCR.648: 5'-TCGAGAAAAGAGCTAGCCCCGGGG-3' (see SEQ. ID. NO: 53)

PCR.649: 5'-AATTCCCCGGGGCTAGCTCTTTTC-3' (see SEQ. ID. NO: 54)

Step 2:

The final expression vectors were constructed via a three point ligation. The BamHI/NheI fragment from pPIC9N which contains the alpha-Mating Factor encoding sequence and the NheI/EcoRI HCVx2 inserts from pUC.HCV21 and pUC.HCV19 were cloned together into a BamHI/EcoRI opened pPIC9 vector. This resulted in the isolation of the *P. pastoris* transformation and expression vectors pPIC.HCV19 and pPIC.HCV21 respectively.

4.2 Production and Analysis of HC-V Biheads.

Step 1: Transformation and Selection of Transformed *P. pastoris* Cells:

*P. pastoris* cells were transformed essentially as described by Faber et al. Briefly: *P. pastoris* GS115 cells were grown overnight at 30EC in 500 ml YPD medium (1% Yeast Extract, 2% Peptone, 1% Glucose) too $OD_{600}$=1.4. The cells were spun and the pellet was washed with sterile distilled water before re-suspending in 100 ml KDTT buffer (50 mM Potassium Phosphate pH 7.5, 25 mM DTT). After 15 minutes incubation at 37EC the cells were pelleted (3 minuntes 3000 rpm) and re-suspended in 100 ml ice-cold STM buffer (92.4 g Glucose/l, 10 mM Tris.HCl pH 7.5, 1 mM $MgCl_2$). After 5 washes with this buffer the cell pellet was re-suspended in a final volume of 0.5 ml STM buffer. Approximately 2–5 μg DNA in 2 μl $H_2O$ (BglII digested pPIC constructs: DNA purified via Phenol/Chloroform extractions and precipitation) was mixed with 70 μl of fresh competent *P. pastoris* cells (on ice). The cells were electroporated in a 0.2 cm cuvette at 1.5 kV, 400, 25 μF in a BioRad Gene-Pulser. Immediately after electroporation, 1 ml of YPD medium was added to the cells. After recovery for 1 hour at 30EC, the cells were pelleted and re-suspended in 200 μl M Sorbitol and plated out onto MD plates (1.34% YNB, $4\times10^{-5}$% Biotin, 1% Glucose, 0.15% Agar). Colonies formed by transformed cells (His$^+$) were visible within 48 hours incubation at 30EC. Transformed *P. pastoris* cells GS115 were selected essentially as recommended by the Invitrogen *Pichia pastoris* expression manual. The plates containing the His$^+$ transformants were used to screen for the Mut$^+$ and Mut$^S$ phenotype as follows: Using sterile toothpicks, colonies were patched on both an MM plate (1.34% YNB, $4\times10^{-5}$% Biotin, 0.5% MeOH, 0.15% Agar) and an MD plate, in a regular pattern, making sure to patch the MM plate first. Approximately 100 transformants were picked for each construct. After incubating the plates at 30EC for 2–3 days the plates were scored. Colonies that grow normally on the MD plates but show little or no growth on the MM plates were classified as Mut$^S$ clones.

Step 2: Production and Evaluation of the Bispecific HC-V Biheads.

Transformed and selected *P. pastoris* clones were induced to express bispecific antibody using the protocol outlined below:

1) Using a single colony from the MD plate, inoculate 10 ml of BMGY (1% Yeast Extract, 2% Peptone, 100 mM potassium phosphate pH 6.0, 1.34% YNB, $4\times10^{-5}$% Biotin, 1% Glycerol) in a 50 ml Falcon tube.
2) Grow at 30EC in a shaking incubator (250 rpm) until the culture reaches an $OD_{600}$=2-8.
3) Spin the cultures at 2000 g for 5 minutes and re-suspend the cells in 2 ml of BMMY medium (1% Yeast Extract, 2% Peptone, 100 mM potassium phosphate pH 6.0, 1.34% YNB, $4\times10^{-5}$% Biotin, 0.5% Glycerol).
4) Return the cultures to the incubator.
5) Add 20 μl of MeOH to the cultures after 24 hours to maintain induction.
6) After 48 hours harvest the supernatant by removing the cells by centrifugation.

Figure 16:
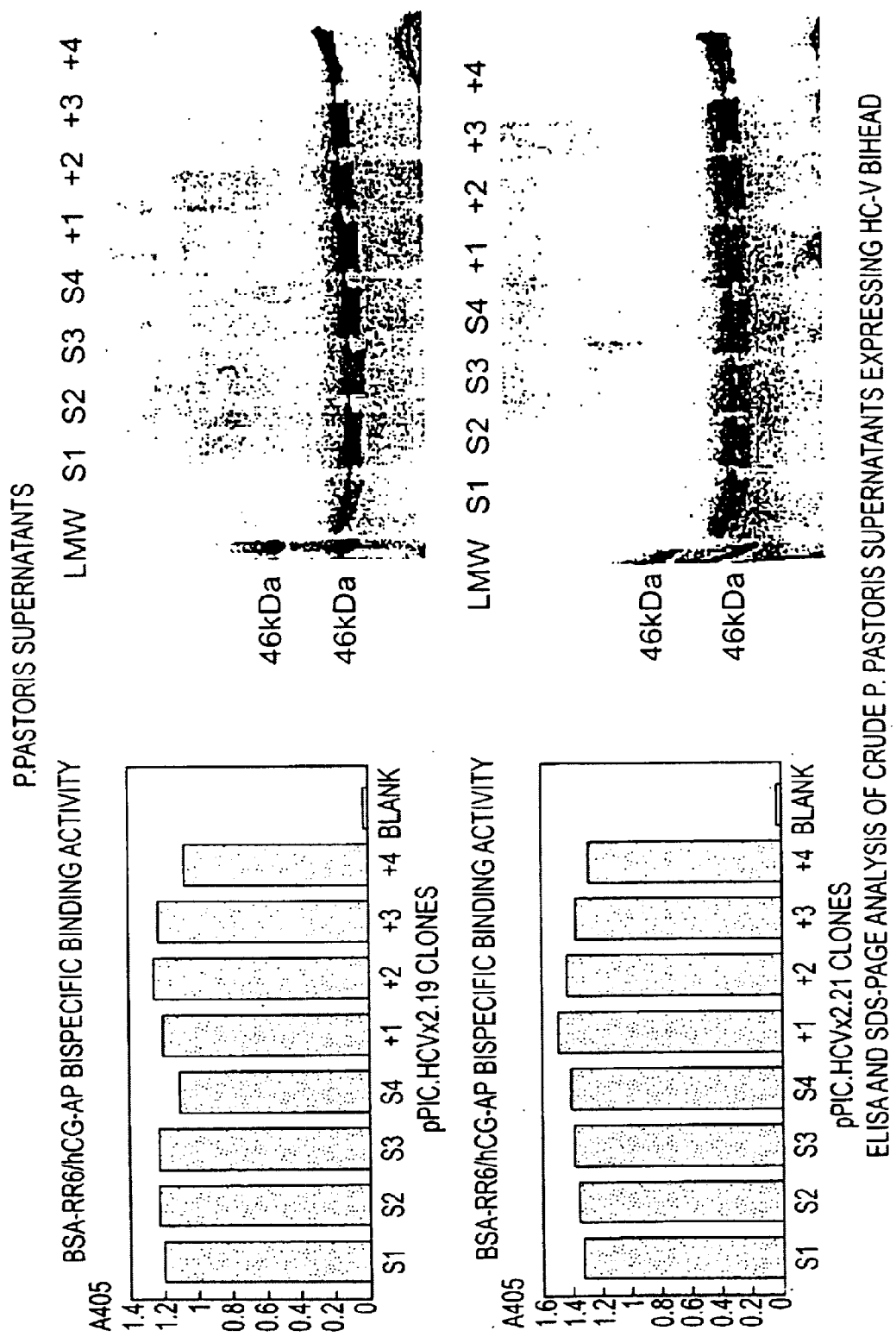
FIG. 16 shows the binding activity and SDS-PAGE analysis of crude *P. Pastoris* supernatants expressing the constructs of Example 4.

The crude supernatants were tested for the presence of HC-V bihead fragment via analysis on 12% acrylamide gels using the Bio-Rad mini-Protean II system (FIG. 16). Bispecific binding activity via shown via ELISA as follows:

1) 96 well ELISA plates (Greiner HC plates) were activated overnight at 37EC with 200 μl/well of the BSA-RR6 conjugate (see Example 1) in PBS.
2) Following one wash with PBST the wells were incubated for 1 hour at 37EC with 200 μl blocking buffer per well. Blocking buffer: 1% BSA in PBS-T.
3) Serial dilutions of test samples (100 μl) were mixed with equal volumes of blocking buffer and added to the sensitised ELISA wells. Incubated at 37EC for 1–2 hours.
4) 200 μl hCG-AP conjugate in blocking buffer was added to each well in which the hCG was coupled to the alkaline phospathase via glutaraldehyde coupling.
5) Following one wash with PBST captured hCG-AP was detected by adding 100 μl/well pNPP substrate (1 mg/ml pNPP in 1M diethanolamine/1 mM $MgCl_2$).

Example 5

Production of HC-V Biheads by *H. polymorpha*

5.1 Construction of Integration Vectors for the Expression of Anti-hCG/Anti-RR6 Bispecific Biheads.

Figure 17:
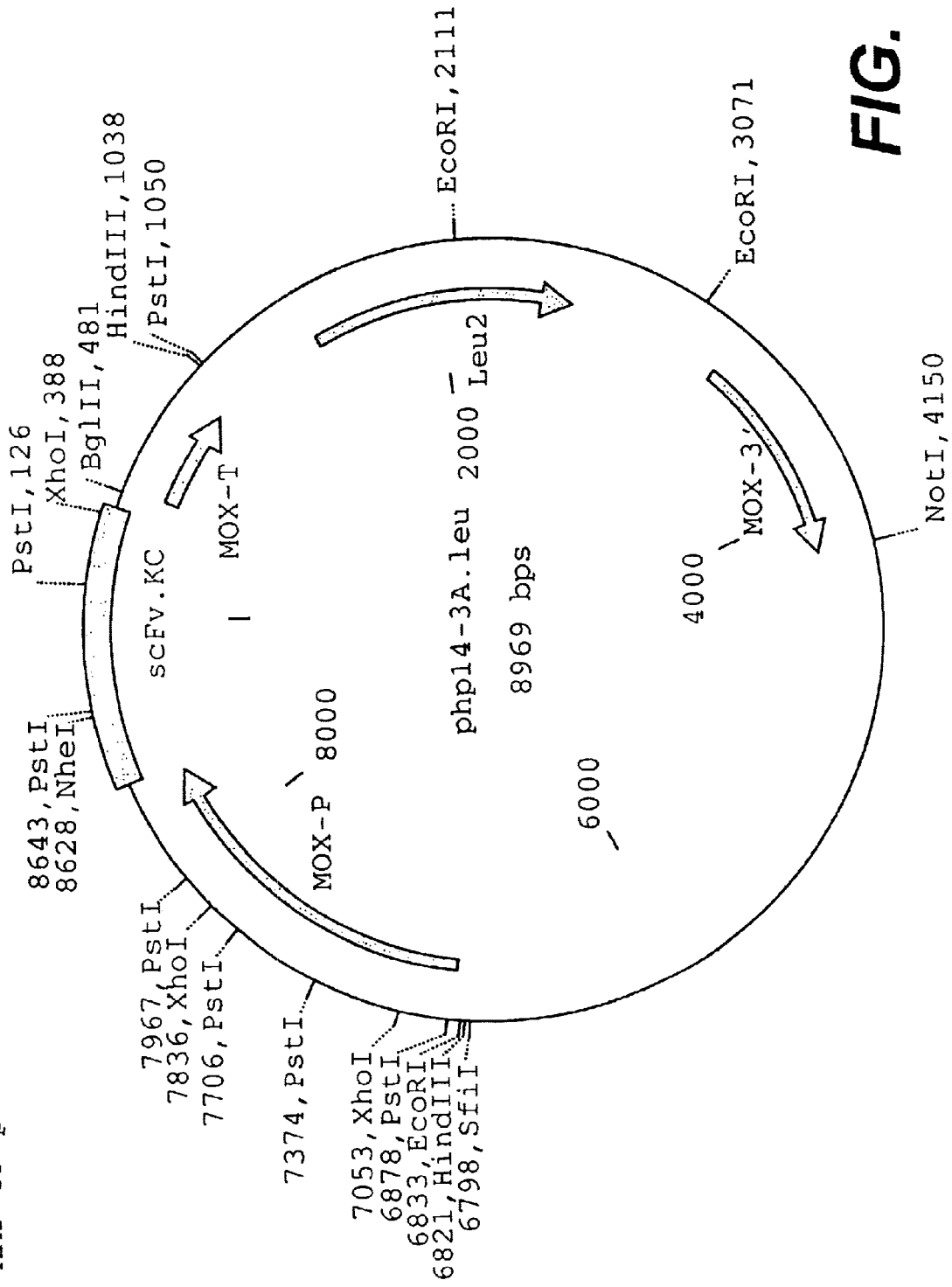
FIG. 17 shows a plasmid map of pHP14.3A.

To allow the expression and secretion of the Llama bihead constructs in *H. polymorpha* strain A16 (Leu-) (Hodgkins et al), the bispecific HC-V gene construct was fused to the alpha-mating factor leader sequence and cloned downstream of the MOX promoter in the *H. polymorpha* transformation and expression vector pHP14.3 (See FIG. 17). A culture of *E. coli* cells harbouring plasmid pHP14.3 was deposited under the Budapest treaty at the National collection of Type Cultures (Central Public Health Laboratory) in London (United Kingdom) under deposition number NCTC13048. The construction of the final expression vectors involved several cloning steps.

Step 1:

Construction of the pUC19 based shuttle vector pHP.1 in which the HindIII/EcoRI polylinker is replaced with a synthetic HindIII/EcoRI fragment, destroying the original EcoRI site and introducing a BamHI, MunI and two BglII sites:

(see SEQ. ID. NO:55)
AAGCTTAGATCTGATCCCGGGCAATTGAGATCTAATTC
HindIII BglII BamHI     MunI  BglII The new insert was constructed by annealing the synthetic oligonucleotides PCR.448 and PCR.449.

```
PCR.448:  5'-AGCTTAGATCTGGATCCCGGGCAATTGAGATCT-3' (see SEQ. ID. NO: 56)

PCR.449:  5'-AATTAGATCTCAATTGCCCGGGATCCAGATCTA-3' (see SEQ. ID. NO: 57)
```

Step 2:

The alpha-mating factor leader-bispecific HC-V gene from the pPIC9-HCV19 and pPIC9-HCV21 vectors were excised as BamHI-EcoRI fragments and inserted into the BamHI/MunI opened shuttle vector pHP.1 giving pHP1.HCV19 and pHP1.HCV21 respectively.

Step 3:

In the final cloning step, the NheI/BglII inserts from the intermediate constructs pHP1.HCV19 and pHP1.HCV21 were inserted into the NheI/BglII opened *H. polymorpha* transformation vector pHP14.3 yielding pHP14.HCV19 and pHP14.HCV21 respectively.

5.2 Production and Analysis of the HC-V Biheads.

Step 1: Transformation and selection of transformed *H. polymorpha* Cells:

*H. polymorpha* cells (strain A16) were transformed essentially as described under 4.2 except that all culturing was done at 37EC and the pHP constructs were digested with SfiI/NotI before transformation. The plates containing the Leu$^+$ transformants were used to screen for the Mut$^+$ and Mut$^-$0 phenotype as described under 4.2.

Step 2: Production and Evaluation of the Bispecific HC-V Biheads:

Transformed and selected *H. polymorpha* clones were induced to express bispecific antibody using the same protocol used to express HC-V bihead in *P. pastoris* as described under 4.2. The crude supernatants were tested for the presence of HC-V bihead fragment via analysis on 12% acrylamide gels using the Bio-Rad mini-Protean II system (FIG. 18). Bispecific binding activity via shown via ELISA (see 4.2).

Example 6

Production of Llama HC-V Triple-Heads by *S. cerevisiae*

Upon digesting pUR4603 and pUR4642 with BstEII and HindIII, the about 6.8 kb vector fragment can be isolated and religated in the presence of the oligonucleotides MPG160WB and MPG161WB (see Example 3.1). From the resulting plasmids, an about 0.4 kb PstI fragment can be isolated, encoding the anti-Streptococcus HC-V fragments, from which the first five amino acids are lacking at the N-terminus and are fused to the C-terminus. Upon digesting either one of the plasmids pUR4618–pUR4621 with PstI, and subsequently religating the vectors with the about 0.4 PstI fragments obtained as described above, a new set of yeast expression plasmids can be obtained. The orientation of the about 0.4 PstI fragment in the newly obtained plasmid can be determined via a digestion with BstEII. The proper orientation will result in two fragments of about 0.4 kb. The wrong orientation will result in a fragment of about 0.75 and a small fragment of about 0.05 kb. Plasmids with the PstI fragment in the proper orientation will encode tripleheads consisting of an HC-V fragment binding to HCG, directly followed by an HC-V fragment binding to Streptococcus, directly followed by an HC-V fragment binding to RR6 and finally the myc-tail.

It will be appreciated that it is possible (for those skilled in the art) to design alternative construction routes.

Example 7

Reduction of the Infectivity of Lactic Acid Bacteria Phages by the Use of Llama HC-V Biheads 7.1 Coupling of RR6-Dye Molecules to the Phage To coat the phages with RR6 molecules 10 µl P2 phage stock (~$10^{12}$ phages/ml)+890 µl coupling buffer (0.1M sodium tetraborate, 0.15M NaCl, pH 8.5)+100 µl RR6 solution in coupling buffer, were mixed and incubated for 1 hour at 37EC (ration of 5*$10^4$ RR6 molecules to 1 phage). To inactivate non-reacted chloro-atoms of RR6, 5 µl blocking buffer (1.0M Tris blocking buffer pH 9, with an excess of primary amino groups) was added and incubated 30 minutes at 37EC.

7.2 Effect of Biheads on the Infectivity of RR6-Coated Phages.

Figure 19:
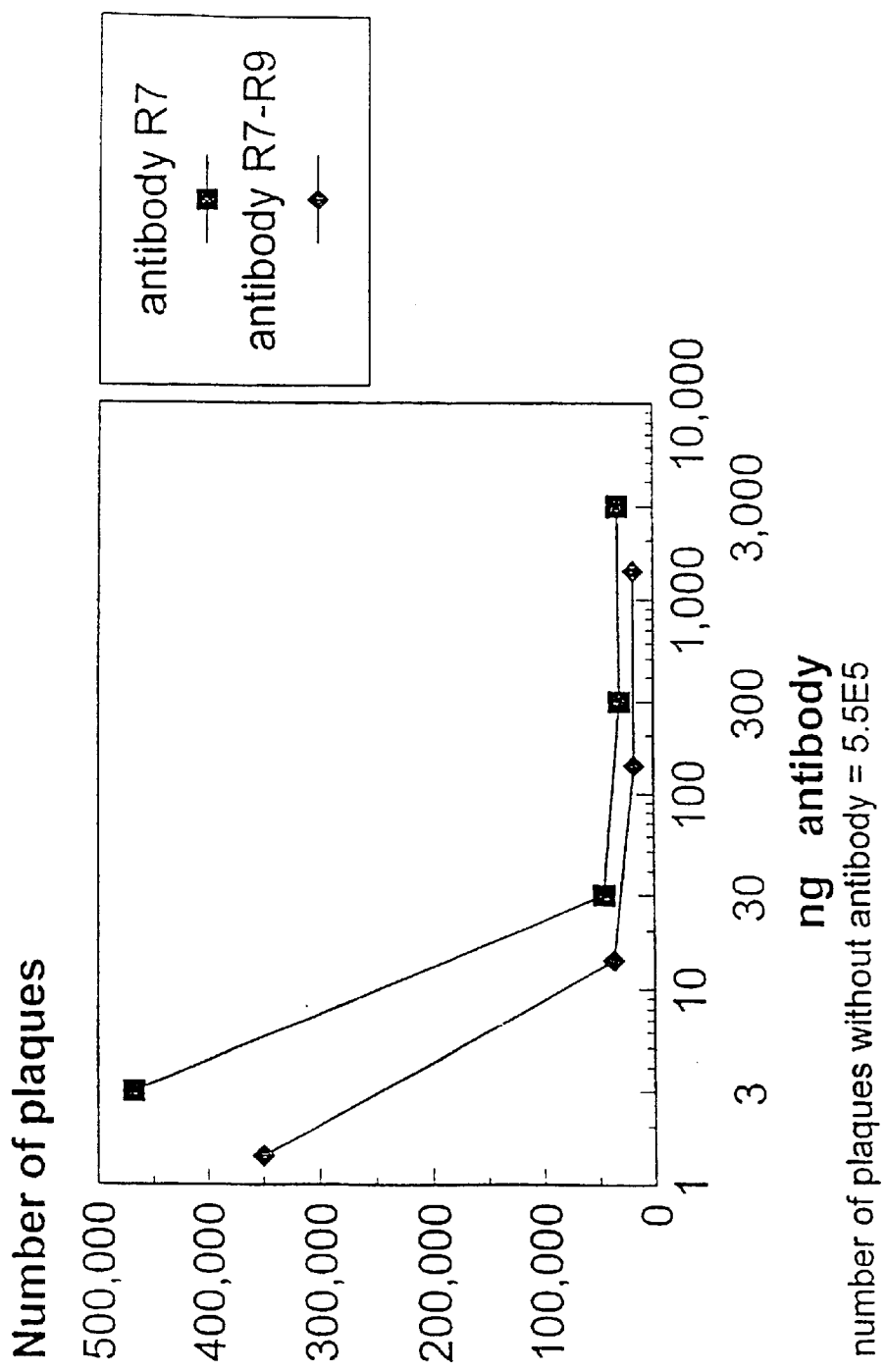
FIG. 19 shows the reduction of infectivity of lactic acid bacteria phages using the constructs according to the invention.
Figure 20:
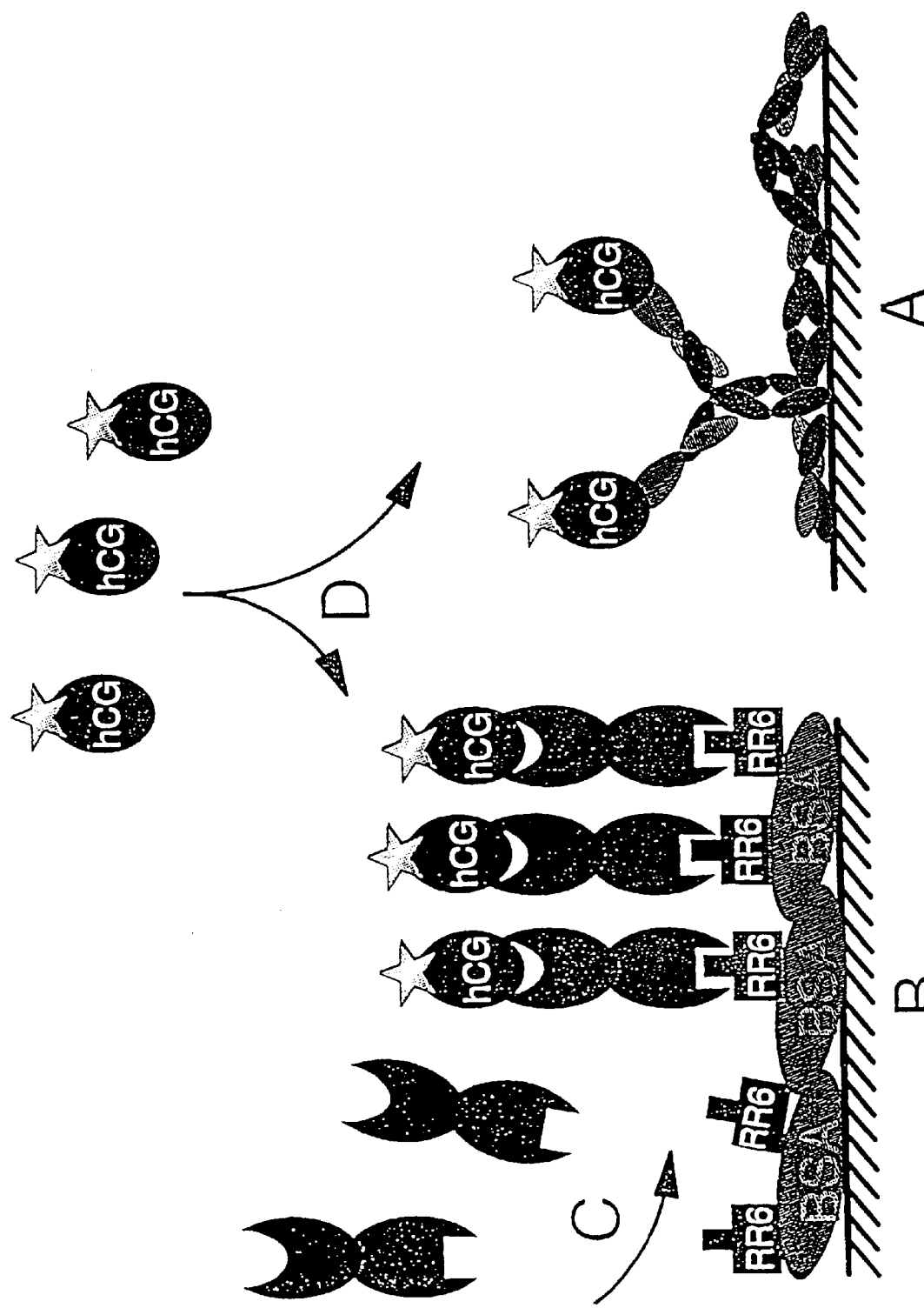
FIG. 20 shows a diagrammatic representation of the use of a biheaded antibody to form an active binding layer.

To test the neutralising effect of the anti-RR6 bihead produced by *S. cerevisiae* containing plasmid pUR4623, this bihead was mixed (in a range of 0–300 ng) with 5.5*$10^5$ phages in 200 µl total volume and incubated for 0.5 hours at 37EC. From this mixture, 100 µl was added to 100 µl of an overnight culture of *Lactococcus lactis* subsp. *cremoris* LM0230, grown in M17 (1*$10^9$ cfu/ml) and spread on a plate of M17 containing 0.5% glucose and 10 mM CaCl$_2$. Plates were incubated overnight at 30EC. In FIG. 19 it is shown that 14 ng bivalent antibody fragments give a reduction of infection of over 90%.

Example 8

Reduction of the Infectivity of Lactic Acid Bacteria (LAB) Phages by the Use of Llama HC-V Biheads 8.1 Raising Heavy Chain Antibodies against the LAB Phage P2 and Obtaining Antigen Specific HC-V Fragments An immune response directed against the LAB P2 phages was induced and followed in essentially the same way as described in Example 1. The llama was injected several times with about 0.2 mg phage protein. From the immunised llama an enriched lymphocyte population was obtained and subsequently HC-V gene fragments were obtained as described in Example 2.1. The construction and screening of a yeast HC-V library was performed essentially as described in Examples 2.2 and 2.3.

In this way a number of anti-LAB-phage fragments were obtained. The sequence of three of these are presented below:

```
pUR3823:                (see SEQ. ID. NO:58)
QVQLQESGGG LVQTGGSLRL SCAASGRTSS DYSVGWFRQA

PGKEREFLAV MMLSGTGTYY ADSVKGRAAI SRDLAKNTVY

LEMNSLKPED TAVYYCALDR AGWLRTEENV YDYWGQGTQV

TVSS pUR3824:                (see SEQ. ID. NO:59)
QVQLQESGGG LVQPGGSLRL SCAVSGAPFR ESTMAWYRQT

PGKERETVAF ITSGGSKTYG VSVQGRFTIS RDSDRRTVLL

QMNNLQPEDT AVYYCHRALS NTWGQGIQVT VSS pUR3825:                (see SEQ. ID. NO:60)
QVQLQESGGG LVQPGGSLRL SCVVSGEGFS NYPMGWYRQA

PGKQRELVAA MSEOGDRTNY ADAVKGRFTI SRDNAKKTVY

LQMSSLKPED TAVYYCNAAR WDLGPAPFGS WGQGTQVTVS

S
```

8.2 Construction of Episomal Expression Plasmids Encoding Anti-LAB-Phage Bivalent Biheads Episomal expression plasmids encoding bivalent anti-LAB phage biheads were constructed essentially as described in Examples 3.1 and 3.2, using the above mentioned fragments as starting material. In this way amongst others the plasmids pUR3843 and pUR3850 were constructed encoding the bihead preceded by the SUC2 secretion signal.

```
pUR3843:        SUC2 - 3823 - 3825 pUR3850:        SUC2 - 3825 - 3824
```

The HC-V biheads 3843 and 3850 were produced by yeast transformants obtained essentially as described in Example 3.3.

8.3 Effect of Biheads on the Infectivity of LAB-Phages

To test the neutralising effect of the anti-LAB-phage biheads produced by *S. cerevisiae* containing plasmids pUR3843 or pUR3850, the biheads were mixed (45 $\mu$g of 3843 and 24 $\mu$g of 3850) with $10^3$, $10^6$ or $10^8$ phages in 200 $\mu$l total volume. After an incubation for 0.5 hours at 37EC, 100 $\mu$l of an overnight culture of *Lactococcus lactis* subsp. *cremoris* LM0230, grown in M17 ($1*10^6$ cfu/ml) was added to these mixtures. Subsequently the mixture was spread on a plate of M17 containing 0.5% glucose and 10 mM $CaCl_2$. Plates were incubated overnight at 30EC after which the number of pfu's was estimated.

TABLE 1

| | Number of plague forming units | | |
|---|---|---|---|
| Bihead ($\mu$g) | $10^3$ phages | $10^6$ phages | $10^8$ phages |
| 3843 (45) | 0 | $<10^3$ | Confluent |
| 3850 (24) | 0 | 0 | $<10^3$ |

8.4 Effect of Biheads on the Acidification of Milk

Figure 25:
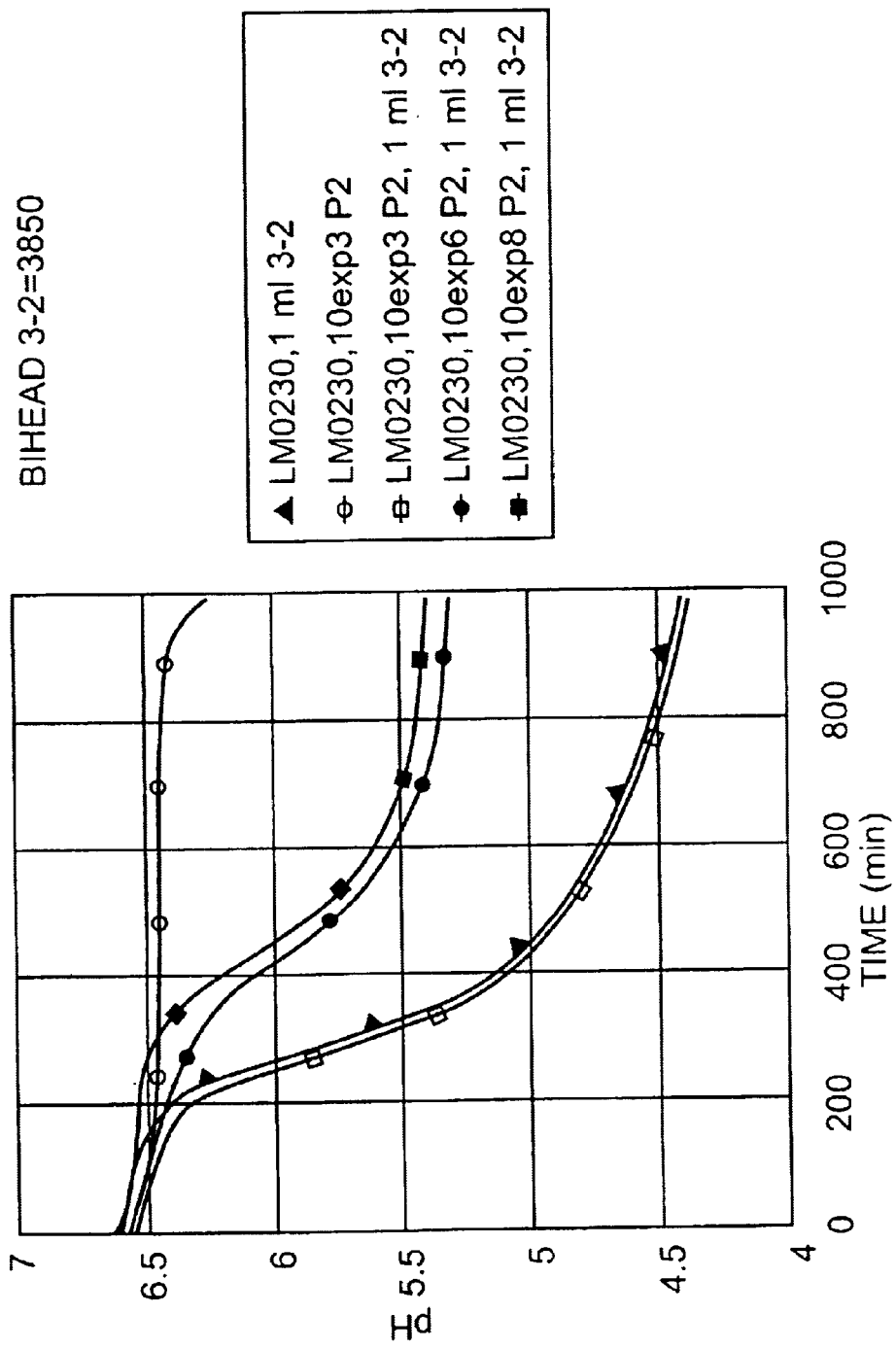
FIG. 25 shows acidification curves of milk by the lactic acid bacterium *Lactococcus lactis* subsp. *cremoris* LM0230 with and without phage P2 and/or bihead 3850 (also referred to as bihead 3-2).

In a subsequent experiment the acidification of milk upon inoculation with lactic acid bacteria at 30° C. was followed by the simultaneous registration of the pH with a HP-3852A Data Acquisition logger. To this end 100 ml XVM-glucose medium (=skim milk containing 0.35% yeast extract, 0.35% peptone and 1% glucose) was inoculated with 100 $\mu$l of an overnight culture of *Lactococcus lactis* subsp. *cremoris* LM0230 in XVM-glucose ($10^9$ cfu/ml) and incubated for 17 h at 30° C. after addition of 240 $\mu$g bihead 3850. The XVM is acidified by the culture in a period of 4 h (FIG. 25, graph 1) and is not influenced by the presence of the bihead. When $10^3$ pfu/ml P2 phage was added with the LM0230 culture in a parallel experiment, no acidification occurred during the whole period of 17 h (FIG. 25, graph 2). When $10^3$, $10^6$, or $10^8$ pfu/ml P2 phage was added, together with 240 $\mu$g bihead 3850, the acidification by the culture can be completely (in the case of $10^3$ cfu/ml phage) or partially restored (FIG. 25, graphs 3, 4, 5).

Example 9

Figure 21:
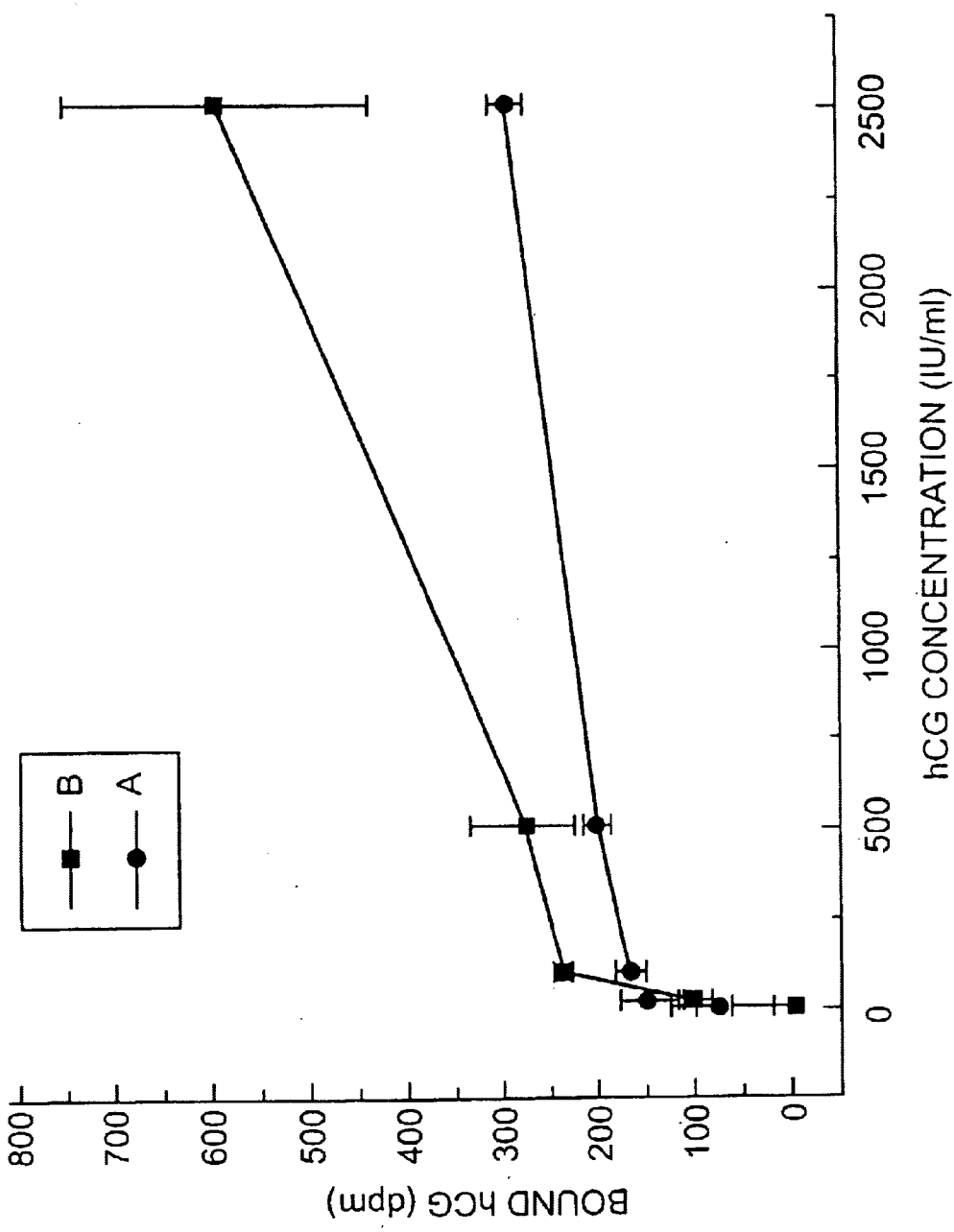
FIG. 21 shows the capture of $I^{125}$ labelled hCG to antibody adsorbed and double headed antibody fragment sensitised RR6-BSA wells.

Activating Surfaces Using HC-V Biheads Via Self Assembly, for Detection and Purification of Analytes 9.1 Use of Bispecific HC-V Bihead to Form an Active Binding Layer on Polystyrene Wells by Self Assembling onto Pre-Adsorbed Molecules.

In summary, this example shows how double headed antibody fragments can be used to form an active binding layer on polystyrene wells by self assembling onto pre-adsorbed molecules. FIG. 20 shows a diagrammatic representation of this. The adsorbed antibody surface is shown (A) as is a surface sensitised with double headed antibody fragment (B) made by the self assembly of double headed antibody fragment onto a pre-adsorbed RR6-BSA surface (C). These two surfaces are then able to bind hCG (D).

Preparation of a Reactive Red 6 Bovine Serum Albumin Conjugate

A conjugate of reactive red 6 (RR6) and bovine serum albumin (BSA) was made by incubating 200 $\mu$l of RR6 (10 mg/ml in distilled $H_2O$) with 1 ml of BSA (10 mg/ml in phosphate buffered saline) with constant mixing for 3 hours at room temperature. A 200 $\mu$l solution of ethanolamine (1M in distilled $H_2O$) was added and the resulting solution mixed constantly for 15 minutes at room temperature. The BSA-RR6 conjugate was separated from free RR6 by application of 0.75 ml to a PD10 column (Pharmacia) and the column eluted with phosphate buffered saline containing 0.1% sodium azide. The eluent was collected as 1 ml fractions. Fractions 4 and 5 were red in colour and were pooled (the RR6-BSA conjugate elutes before unreacted or free RR6). Fractions 10 onwards were also red in colour but these fractions contain the unbound RR6 and so were discarded.

Preparation of Polystyrene Wells Adsorbed with RR6-BSA

Individual wells from Greiner high binding plates were isolated from a 96 well plate by sawing. Into these wells, 100 $\mu$l aliquots of 10 $\mu$g/ml of RR6-BSA or monoclonal antibody recognising hCG was added and incubated for 3 hours at room temperature. Both the antibody adsorbed and RR6-BSA adsorbed wells were then washed 3 times with PBSTA.

Self Assembly of a Double Headed Antibody Fragment onto RR6-BSA Wells

Following the PBSTA wash of RR6-BSA wells, 100 $\mu$l of affinity purified double headed antibody fragment (HI15-R9: pPIC.HCV2l) at 20 $\mu$g/ml in PBSTA was added per well. After 1 hour the RR6-BSA wells were washed 3 times with PBSTA.

Capture of $I^{125}$ labelled hCG to Antibody Adsorbed and Double Headed Antibody Fragment Sensitised RR6-BSA Wells hCG (2500 IU/ml in PBSTA) was spiked with 10 $\mu$Ci $I^{125}$ hCG (Amersham) and then diluted to 500, 100, 20 and 4

IU/ml of hCG with PBSTA. Aliquots (100 µl) of these dilutions were incubated in the wells for 1 hour at room temperature after which time the wells were extensively washed with PBSTA. Wells were then counted on a gamma counter. FIG. 21 shows the amount of dpm captured by the monoclonal antibody adsorbed wells (A) and by the double headed antibody fragment sensitised wells (B) over a range of hCG concentrations.

The double headed antibody fragment sensitised wells (HI15-R9: pPIC.HCV21) bound approximately twice as much hCG than the adsorbed antibody wells at saturating hCG concentrations. This would indicate that the double headed antibody fragment sensitised wells possessed a higher density of active hCG binding sites than the adsorbed antibody wells.

9.2 Use of Bispecific HC-V Bihead to Self Assemble on Latex Particles for the Detection of Human Chorionic Gonadotrophin (hCG)

Preparation of a RR6-BSA Latex

To 950 µl of 10 mM borate buffer, 0.01% merthiolate, pH 8.5 a 50 µl aliquot of Duke blue latex (10% solids) was added and mixed by inverting. The diluted latex was then centrifuged at 8,000 g for 10 minutes at room temperature, the supernatant removed and the pellet vortexed briefly. The pellet was re-suspended in a solution made up of 900:1 of borate buffer (as above) and 100 µl of the previously prepared RR6-BSA conjugate. Latex particles were sonicated for 10 s using a sonic probe. The solution containing the latex was mixed for 30 minutes at room temperature. Following this the latex was pelleted as before and re-suspended in 1 ml of the borate buffer.

Self Assembly of a Double Headed Antibody Fragment onto RR6-BSA Latex

By virtue of its specificity the double headed antibody fragment: (HI15-R9: pPIC.HCV21) self assembles on the surface of a RR6-BSA latex. This was achieved by incubating 5:1 of the RR6-BSA latex with 3:1 of supernatant from *Pichia pastoris* expressing the bihead HI15-R9 (pPIC.HCV21) made up to 40 µl with phosphate buffered saline containing 0.1% sodium azide and 0.1% Tween 20 (PBSTA) for 15 minutes at room temperature.

Figure 22:
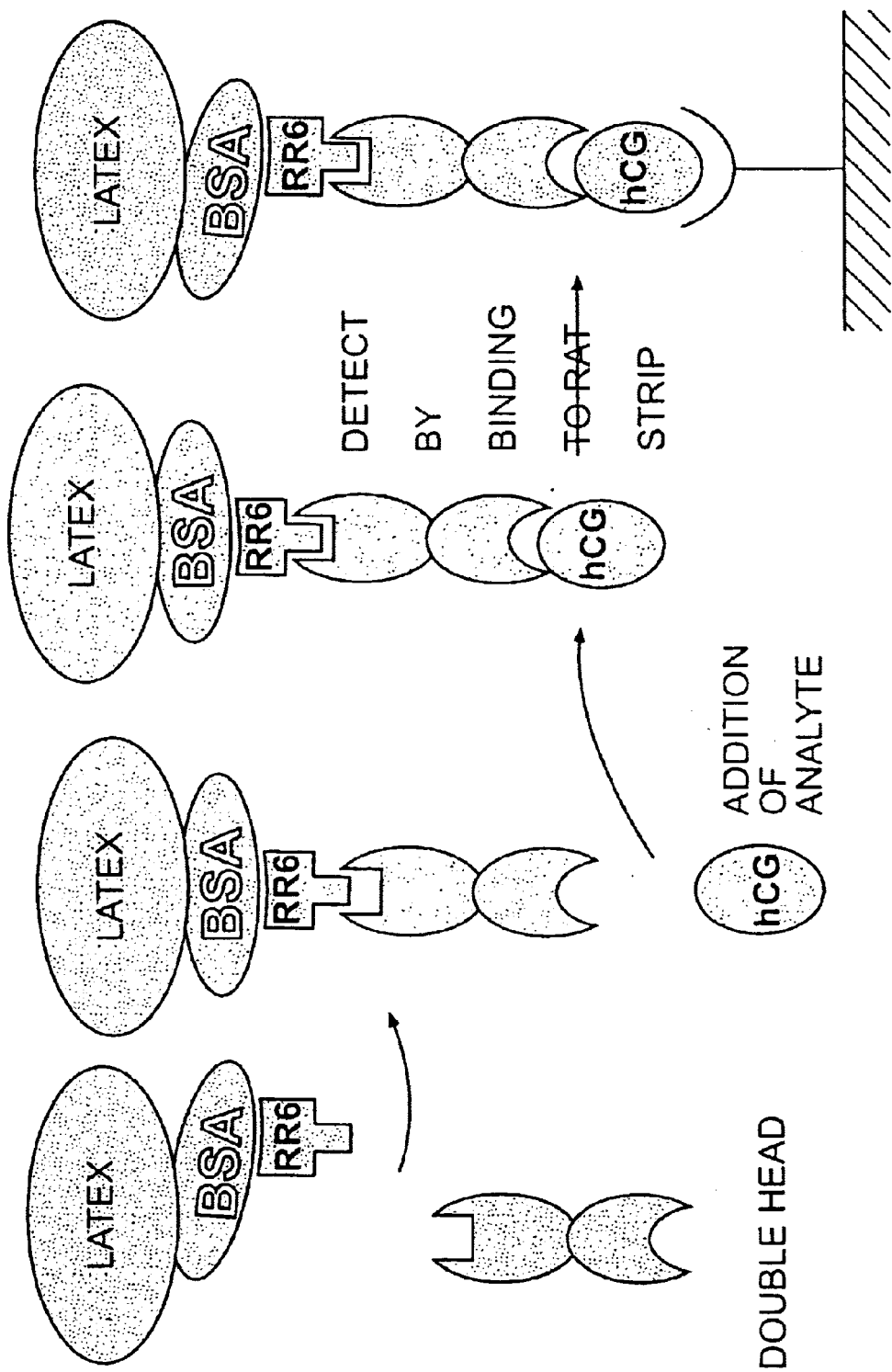
FIG. 22 shows a schematic representation of the use of a bispecific biheaded antibody fragment of the invention in an immunoassay to detect hCG antigen.
Figure 23:
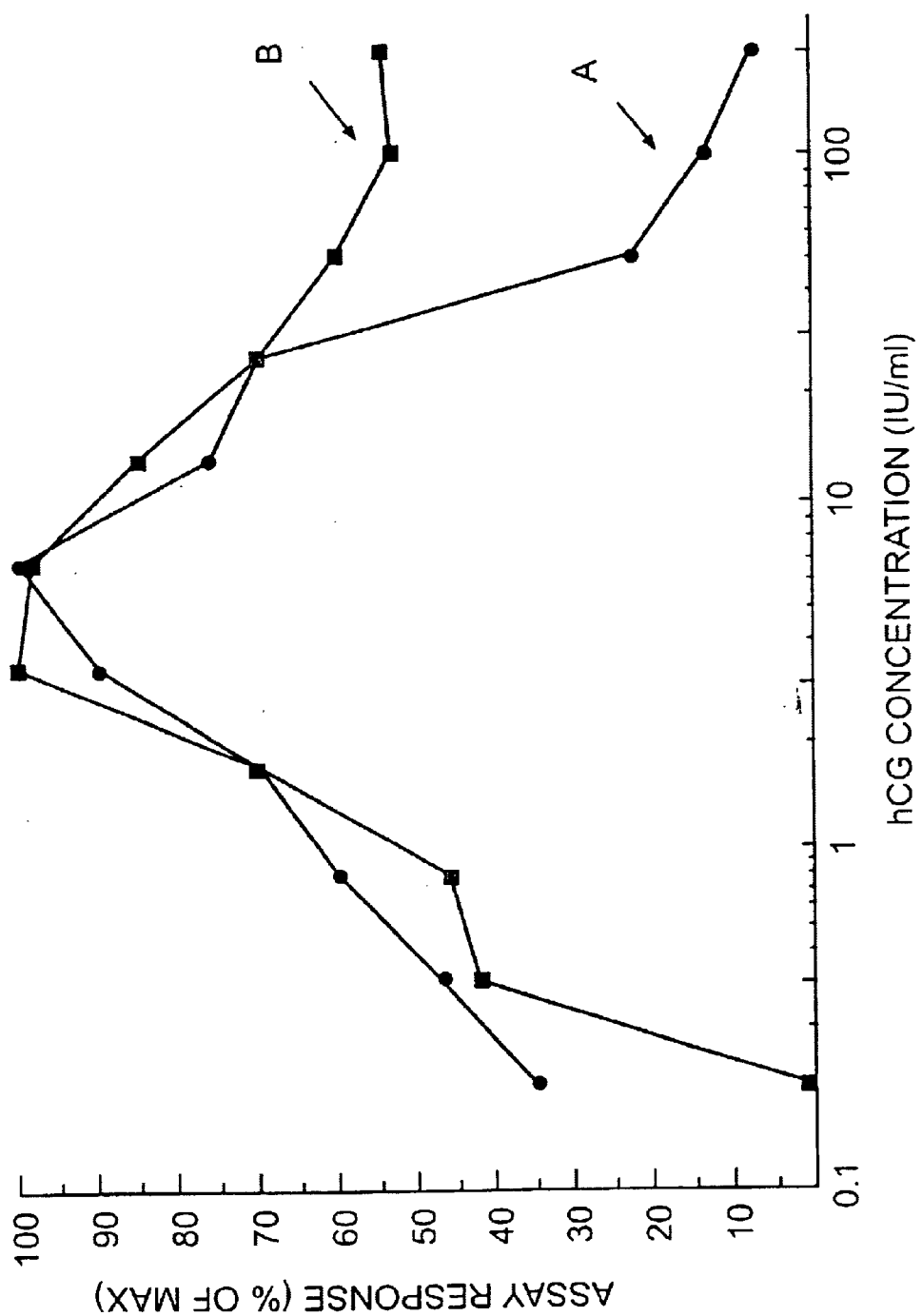
FIG. 23 shows the assay response of latex made by adsorption of a monoclonal antibody and self-assembled bihead/RR6-BSA latex.
Figure 24:
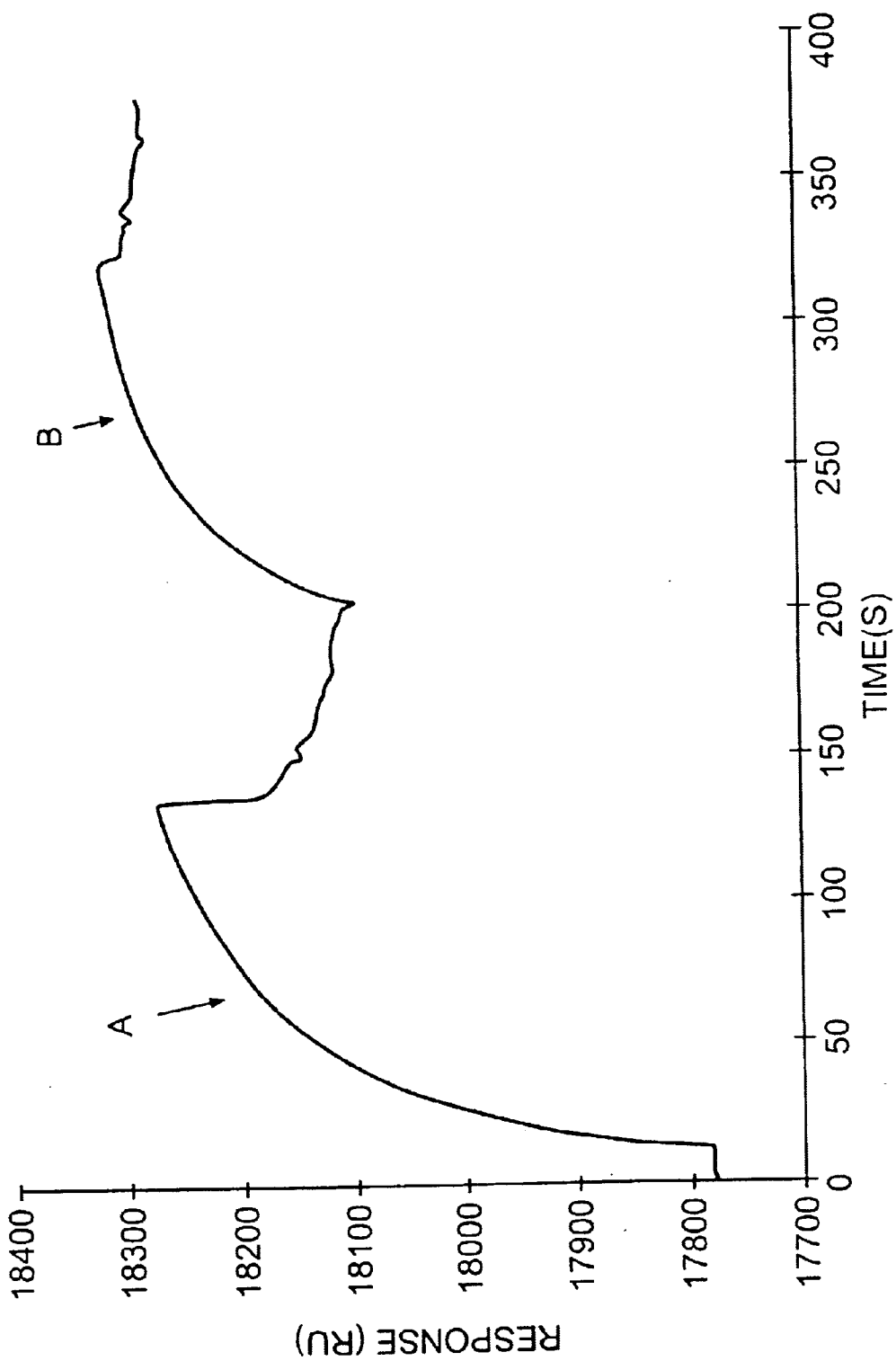
FIG. 24 shows the assembly of a bispecific antibody fragment on a dextran surface coated with RR6-BSA.

Assessing the Self Assembled Double Head for Use in hCG Assay hCG (10 µl at various concentrations) was added to the self assembled double head RR6-BSA latex and incubated for 15 minutes at room temperature. The mixture was then allowed to flow up a nitrocellulose strip. The nitrocellulose strip had a line of antibody recognising a different epitope to hCG than the double headed antibody fragment (FIG. 22 shows a schematic representation of the principle). The amount of latex binding at the antibody line was determined by scanning the intensity of the line using an autoreader. The results are shown in FIG. 23. By way of comparison a latex was made by adsorption of a monoclonal antibody, specific for hCG, using a similar methodology as that for the RR6-BSA latex. This latex was incubated with hCG (10 µl at the various concentrations) and also subjected to the same evaluation on a nitrocellulose strip (results shown in FIG. 23).

FIG. 23 shows that the self assembling latex compares well with the adsorbed antibody latex. In fact, the hook effect seen with the adsorbed latex (labelled A in FIG. 23) at the higher hCG concentrations is less pronounced with the self assembling latex (labelled B in FIG. 23) giving the assay a higher range of hCG detection. The most likely explanation for this is an increased number of hCG binding sites on the self assembling latex compared with the adsorbed latex.

9.3 Assembly of Bispecific HC-V Antibody Fragments to a Dextran Surface Coupled with RR6-BSA Conjugate Preparation of a Bialite Chip Coupled with RR6-BSA A new CM5 biosensor chip (Biacore AB) was docked into a Bialite biosensor (Biacore AB). The flow rate, of HEPES buffered saline (HBS) was set to 10 μl/min. The RR6-BSA conjugate was amine coupled to the CM5 chip using an amine coupling kit (Biacore AB) according to the manufacturer's instructions. Briefly, two 40 μl injections of NHS/EDC were performed to activate the biosensor chip surface. Following activation, two 40 μl injections of RR6-BSA (diluted 1:10 in 10 mM sodium acetate, pH 4.0) were performed. The biosensor chip surface was then blocked by two injections of 40:1 ethanolamine (1M).

Preparation of a Binding Surface by Self Assembly of Double Headed Antibody Fragment and Subsequent Detection of hCG Double headed antibody fragment (HI15-R9: pPIC.HCV21) was assembled onto the RR6-BSA coupled dextran surface by injection of 20 μl purified double headed antibody fragment (HI15-R9: pPIC.HCV21, 100 μg/ml in HBS). This can be seen as an increase in response units (RU) on the Bialite sensorgram shown in FIG. 24 labelled A. hCG was then injected (20 μl of a 10 IU/ml solution made up in HBS). Detection of hCG can be seen by an increase in RU (FIG. 24, labelled B).

Example 10

Anti-hCG/Anti-RR6 Bispecific Biheads Containing a Linker Peptide 10.1 Construction of *S. cerevisiae* Episomal Expression Plasmids Encoding Anti-hCG/Anti-RR6 Bispecific Biheads Containing a Linker Peptide.

Between the H14 and the R9 encoding DNA fragments synthetic linkers were introduced encoding different linker peptides. To this end the about 50 bp long BstEII-HindIII fragment of pJS7 (see Example 3.1) was replaced by an about 50 bp long BstEII-HindIII fragment having the following sequence:

```
MVaJA                                      (see SEQ. ID. NO:61)
   BstEII    XbaI       DraIII       PstI             HindIII
5' GTCACCGTCTCTAGATGGCCACCAGGTGCAGCTGCAGGAGTCAACTTA 3'

MVbJA                                      (see SEQ. ID. NO:62)
3' GCAGAGATCTACCGGTGGTCCACGTCGAGCTCCTCAGTTGAATTCGA 5'
```

This resulted in pSJ7a. In this plasmid the about 20 bp PstI-HindIII fragment was replaced with the about 370 bp PstI-HindIII fragment encoding the anti-RR6 HC-V fragment R9 and/with the myc-tail of pUR4640 (see Example 3.1) and resulting in pSJ7b.

Upon digesting plasmid pSJ7b with XbaI and DraIII the about 7 kb vector fragment was ligated with five synthetic oligo nucleotide linker fragments presented below:

MV01JA (see SEQ. ID. NO:63)
5' CTAGTGGTACTTCCGGTTCCCAG 3'

MV02JA (see SEQ. ID. NO:64)
3'     ACCATGAAGGCCAAGG 5'

(see SEQ. ID. NO:65)
    S  G  T  S  G  S  Q

MV03JA (see SEQ. ID. NO:66)
5' CTAGTTCTTCATCTGCTTCTGCCTCTTCAGCCCAG 3'

MV04JA (see SEQ. ID. NO:67)
3'     AAGAAGTAGACGAAGACGGAGAAGTCGG 5'

(see SEQ. ID. NO:68)
    S  S  S  S  A  S  A  S  S  A  Q

MV05JA (see SEQ. ID. NO:69)
5' CTAGTGGTTCTCCAGGTTCACCAGGTCAG 3'

MV06JA (see SEQ. ID. NO:70)
3'     ACCAAGAGGTCCAAGTGGTCCA 5'

(see SEQ. ID. NO:71)
    S  G  S  P  G  S  P  G  Q

MV07JA (see SEQ. ID. NO:72)
5' CTAGTGCTACTACAACTGGTTCTTCACCAGGTCCAACTCAG 3'

MV08JA (see SEQ. ID. NO:73)
3'     ACGATGATGTTGACCAAGAAGTGGTCCAGGTTGA 5'

(see SEQ. ID. NO:74)
    S  A  T  T  T  G  S  S  P  G  P  T  Q

MV09JA (see SEQ. ID. NO:75)
5' CTAGTGCTAATCATTCTGGTAATGCTTCTCAG 3'

MV10JA (see SEQ. ID. NO:76)
3'     ACGATTAGTAAGACCATTACGAAGA 5'

(see SEQ. ID. NO:77)
    S  A  N  H  S  G  N  A  S  Q

The oligonucleotide linker fragments encode the last amino acid of the N-terminal HC-V fragment (S) and the first amino acid of the C-terminal HC-V fragment, intersected by the connecting linker peptide. This resulted in plasmids pUR5330 to 5334, respectively.

After transformation of *S. cerevisiae* with these plasmids, the production levels of the biheads were determined via Western blot analysis and a anti-hCG ELISA using anti-myc mAb for detection of the bound bihead (see Example 2.3). Production levels are presented in Table 2 below:

TABLE 2

| Plasmid | Linker | Production level (mg/l) |
|---|---|---|
| pUR4619 | None | 11 |
| pUR5330 | S-G-T-S-G-S-Q | 36 |

TABLE 2-continued

| Plasmid | Linker | Production level (mg/l) |
|---|---|---|
| pUR5331 | S-S-S-S-A-S-A-S-S-A-Q | 49 |
| pUR5332 | S-G-S-P-G-S-P-G-Q | 33 |
| pUR5333 | S-A-T-T-T-G-S-S-P-G-P-T-Q | 56 |
| pUR5334 | S-A-N-H-S-G-N-A-S-Q | 51 |

The production levels of the biheads in which the two HC-V domains are separated by a linker peptide (consisting of between 5 and 11 amino acids) were found to be 3 to 5 times higher as found for the bihead in which the two HC-V fragments are connected without a peptide linker.

It is therefore expected that other linker peptides, e.g. the short hinge regions found in the heavy chain antibodies are equally suitable and give even better production yields.

Figure 26:
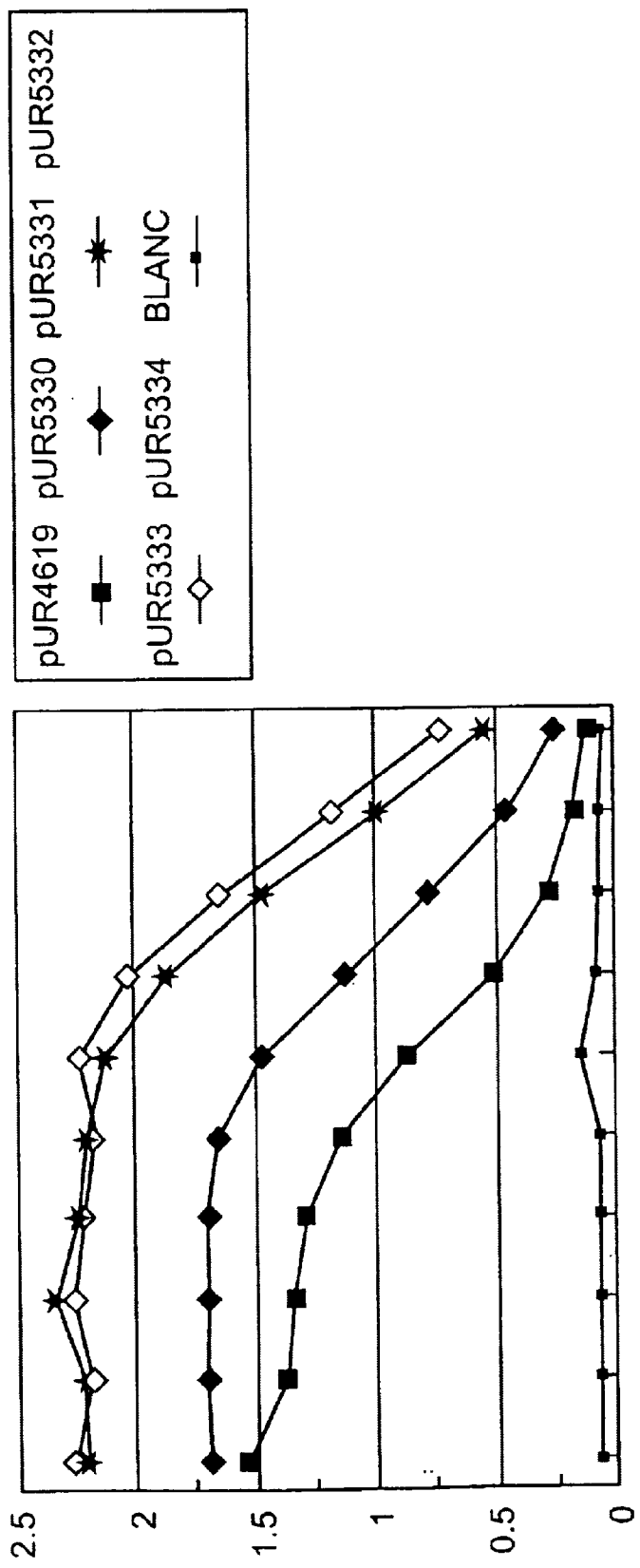
FIG. 26 shows the A405 signals of an ELISA to determine bispecificity of H14-R9 biheads A405.

Finally, the bispecificity of the biheads was demonstrated using the ELISA as described in Example 3.3, the results of which are presented in FIG. 26.

LITERATURE REFERRED TO IN THE EXAMPLES

Chomczynnski, P. and Sacchi, N. (1987) Single step method of RNA isolation by acid guanidium thiocyanate-phenol-chloroform extraction. Analytical Biochem. 162: 156–159.

Bokhout, B. A., Van Gaalen, C., and Van Der Heijden, Ph. J., (1981), A selected water-in-oil emulsion: composition and usefulness as an immunological adjuvant. Vet. Immunol. Immunopath., 2: 491–500

Bokhout, B. A., Bianchi, A. T. J., Van Der Heijden, Ph. J., Scholten, J. W. and Stok, W., (1986), The influence of a water-in-oil emulsion on humoral immunity. Comp. Immun. Microbiol. Infect. Dis., 9: 161–168.

Giuseppin, M. L. F., Lopes, M. T. S., Planta, R. J., Verbakel, J. M. A., Verrips, C. T. (1991) Process for preparing a protein by a yeast transformed by multicopy integration of an expression vector. PCT application WO 91/00920 (UNILEVER)

Harmsen, M. M., Langedijk, A. C., van Tuinen, E., Geerse, R. H., RauP, H. A., Maat, J., (1993) Effect of pmr1 disruption and different signal sequences on the intracellular processing and secretion of *Cyamopsis tetragonoloba*—galactosidase by *S. cerevisiae*. Gene 125 115–123

Faber, K. N., Haima, P., Harder, W., Veenhuis, M and Geert, A. B., (1994) Highly efficient electrotransformation of the yeast Hansenula polymorpha. Current Genetics, 25: 305–310

Hodgkins, M., Mead, D., Ballance, D. J., Goodey, A. and Sudbery, P., (1993) Expression of the Glucose Oxidase Gene from *Aspergillus niger* in *Hansenula Polymorpha* and its use as a reporter gene to isolate regulatory mutations. Yeast, 9:625–635

What is claimed is:

1. A multivalent antigen binding protein comprising a single polypeptide chain comprising two or more single domain binding units, which are connected directly in series, wherein the single domain binding units are heavy chain variable domains obtained from an immunoglobulin naturally devoid of light chains.

2. A protein according to claim 1, wherein the single domain binding units are heavy chain variable domains obtained from a Camelid immunoglobulin.

3. A protein according to claim 2, comprising a bivalent antigen binding protein.

4. A protein according to claim 2, wherein the protein has an additional peptide appended to it.

5. A protein according to claim 2, wherein the protein has an enzyme fused to it.

6. A protein according to claim 2, wherein the single domain binding units have different antigen specificity from each other.

7. A protein according to claim 2, wherein the single domain binding units have the same antigen specificity as each other.

* * * * *

SEQUENCE LISTING

<160> NUMBER OF SEQ ID NOS: 77

<210> SEQ ID NO 1
<211> LENGTH: 11
<212> TYPE: PRT
<213> ORGANISM: Unknown Organism

```
<220> FEATURE:
<223> OTHER INFORMATION: Description of Unknown Organism: Suitable
      peptide linking group

<400> SEQUENCE: 1

Glu Gln Lys Leu Ile Ser Glu Glu Asp Leu Asn
 1               5                  10

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 2
aggtsmarct gcagsagtcw gg                                              22

<210> SEQ ID NO 3
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 3
aacagttaag cttccgcttg cggccgcgga gctggggtct tcgctgtggt gcg            53

<210> SEQ ID NO 4
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 4
aacagttaag cttccgcttg cggccgctgg ttgtggtttt ggtgtcttgg gtt            53

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 5
gggaattcca ataggtggtt agcaatcg                                        28

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 6
gaccaacgtg gtcgcctggc aaaacg                                          26

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 7
```
cgttttgcca ggcgaccacg ttggtc                                               26

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 8
ccccaagctt acatggtctt aagttggcgt                                           30

<210> SEQ ID NO 9
<211> LENGTH: 155
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: CDS
<222> LOCATION: (30..110, 117..140)

<400> SEQUENCE: 9
gagctcatca cacaaacaaa caaaacaaa atg atg ctt ttg caa gcc ttc ctt            53
                                 Met Met Leu Leu Gln Ala Phe Leu
                                  1               5 ttc ctt ttg gct ggt ttt gca gcc aaa ata tct gcg cag gtg cag ctg           101
Phe Leu Leu Ala Gly Phe Ala Ala Lys Ile Ser Ala Gln Val Gln Leu
         10                  15                  20 cag gag tca taatga ggg acc cag gtc acc gtc tcc tca taatgactta             150
Gln Glu Ser        Gly Thr Gln Val Thr Val Ser Ser
 25                 30                  35 agctt                                                                     155

<210> SEQ ID NO 10
<211> LENGTH: 35
<212> TYPE: PRT
<213> ORGANISM: Artificial Sequence
<220> FEATURE:
<223> OTHER INFORMATION: Description of Artificial Sequence: Synthetic
      amino acid

<400> SEQUENCE: 10

Met Met Leu Leu Gln Ala Phe Leu Phe Leu Leu Ala Gly Phe Ala Ala
 1               5                  10                  15

Lys Ile Ser Ala Gln Val Gln Leu Gln Glu Ser Gly Thr Gln Val Thr
             20                  25                  30

Val Ser Ser
         35

<210> SEQ ID NO 11
<211> LENGTH: 188
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: CDS
<222> LOCATION: (30..110, 117..173)

<400> SEQUENCE: 11
gagctcatca cacaaacaaa caaaacaaa atg atg ctt ttg caa gcc ttc ctt            53
                                 Met Met Leu Leu Gln Ala Phe Leu
                                  1               5 ttc ctt ttg gct ggt ttt gca gcc aaa ata tct gcg cag gtg cag ctg           101
Phe Leu Leu Ala Gly Phe Ala Ala Lys Ile Ser Ala Gln Val Gln Leu

```
Phe Leu Leu Ala Gly Phe Ala Ala Lys Ile Ser Ala Gln Val Gln Leu
         10                  15                  20 cag gag tca taatga ggg acc cag gtc acc gtc tcc tca gaa caa aaa    149
Gln Glu Ser        Gly Thr Gln Val Thr Val Ser Ser Glu Gln Lys
 25                     30                  35 ctc atc tca gaa gag gat ctg aat taatgactta agctt                  188
Leu Ile Ser Glu Glu Asp Leu Asn
     40                  45

<210> SEQ ID NO 12
<211> LENGTH: 46
<212> TYPE: PRT
<213> ORGANISM: Artificial Sequence
<220> FEATURE:
<223> OTHER INFORMATION: Description of Artificial Sequence: Synthetic
      amino acid

<400> SEQUENCE: 12

Met Met Leu Leu Gln Ala Phe Leu Phe Leu Leu Ala Gly Phe Ala Ala
 1               5                  10                  15

Lys Ile Ser Ala Gln Val Gln Leu Gln Glu Ser Gly Thr Gln Val Thr
             20                  25                  30

Val Ser Ser Glu Gln Lys Leu Ile Ser Glu Glu Asp Leu Asn
         35                  40                  45

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Val Gln Leu Gln
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Val Thr Val Ser Ser
 1               5

<210> SEQ ID NO 15
<211> LENGTH: 384
<212> TYPE: DNA
<213> ORGANISM: Lama peruana
<220> FEATURE:
<221> NAME/KEY: CDS
<222> LOCATION: (1)..(384)

<400> SEQUENCE: 15 cag gtg cag ctg cag gag tca ggg gga gga ttg gtg cag gct ggg gac    48
Gln Val Gln Leu Gln Glu Ser Gly Gly Gly Leu Val Gln Ala Gly Asp
 1               5                  10                  15 tct ctg aga ctc tcc tgc gcg gcc tcg gga cgc act tct cat ggg tat    96
Ser Leu Arg Leu Ser Cys Ala Ala Ser Gly Arg Thr Ser His Gly Tyr
             20                  25                  30 ggt ggc tat ggc atg ggc tgg ttc cgc caa att cca ggg aag gag cgt   144
```

```
Gly Gly Tyr Gly Met Gly Trp Phe Arg Gln Ile Pro Gly Lys Glu Arg
            35                  40                  45 gag ctt gtc gca gca att agg tgg agc ggt cgt aat aca tac tat gca      192
Glu Leu Val Ala Ala Ile Arg Trp Ser Gly Arg Asn Thr Tyr Tyr Ala
 50                  55                  60 gac tcc gtg aag ggc cga ttc acc atc tcc aga gac aac gtc aag gac      240
Asp Ser Val Lys Gly Arg Phe Thr Ile Ser Arg Asp Asn Val Lys Asp
 65                  70                  75                  80 atg ctg tat ctg caa atg aac agt ttg aaa cct gag gac acg gcc gtt      288
Met Leu Tyr Leu Gln Met Asn Ser Leu Lys Pro Glu Asp Thr Ala Val
                 85                  90                  95 tac act tgt gca gtt cgg acg gtc cgc gtg gtt gac att tcc agt ccg      336
Tyr Thr Cys Ala Val Arg Thr Val Arg Val Val Asp Ile Ser Ser Pro
            100                 105                 110 gtt ggg ttt gcc tac tgg ggc cag ggg acc cag gtc acc gtc tcc tca      384
Val Gly Phe Ala Tyr Trp Gly Gln Gly Thr Gln Val Thr Val Ser Ser
            115                 120                 125

<210> SEQ ID NO 16
<211> LENGTH: 128
<212> TYPE: PRT
<213> ORGANISM: Lama peruana

<400> SEQUENCE: 16

Gln Val Gln Leu Gln Glu Ser Gly Gly Gly Leu Val Gln Ala Gly Asp
 1               5                   10                  15

Ser Leu Arg Leu Ser Cys Ala Ala Ser Gly Arg Thr Ser His Gly Tyr
             20                  25                  30

Gly Gly Tyr Gly Met Gly Trp Phe Arg Gln Ile Pro Gly Lys Glu Arg
            35                  40                  45

Glu Leu Val Ala Ala Ile Arg Trp Ser Gly Arg Asn Thr Tyr Tyr Ala
 50                  55                  60

Asp Ser Val Lys Gly Arg Phe Thr Ile Ser Arg Asp Asn Val Lys Asp
 65                  70                  75                  80

Met Leu Tyr Leu Gln Met Asn Ser Leu Lys Pro Glu Asp Thr Ala Val
                 85                  90                  95

Tyr Thr Cys Ala Val Arg Thr Val Arg Val Val Asp Ile Ser Ser Pro
            100                 105                 110

Val Gly Phe Ala Tyr Trp Gly Gln Gly Thr Gln Val Thr Val Ser Ser
            115                 120                 125

<210> SEQ ID NO 17
<211> LENGTH: 342
<212> TYPE: DNA
<213> ORGANISM: Lama peruana
<220> FEATURE:
<221> NAME/KEY: CDS
<222> LOCATION: (1)..(342)

<400> SEQUENCE: 17 cag gtg cag ctg cag gag tca ggg gga ggc ttg gtg cag gct ggg gag       48
Gln Val Gln Leu Gln Glu Ser Gly Gly Gly Leu Val Gln Ala Gly Glu
 1               5                   10                  15 tct ctg aaa ctc tcc tgt gca gcc tct gga aac acc ttc agt ggc ggc       96
Ser Leu Lys Leu Ser Cys Ala Ala Ser Gly Asn Thr Phe Ser Gly Gly
             20                  25                  30 ttc atg ggc tgg tac cgc cag gct cca ggg aag cag cgc gag ttg gtc      144
Phe Met Gly Trp Tyr Arg Gln Ala Pro Gly Lys Gln Arg Glu Leu Val
            35                  40                  45 gca acc att aat agt aga ggt atc aca aac tat gca gac ttc gtg aag      192
```

```
Ala Thr Ile Asn Ser Arg Gly Ile Thr Asn Tyr Ala Asp Phe Val Lys
         50                  55                  60 ggc cga ttc acc atc tcc aga gac aat gcc aag aag aca gtg tat ttg      240
Gly Arg Phe Thr Ile Ser Arg Asp Asn Ala Lys Lys Thr Val Tyr Leu
 65                  70                  75                  80 gaa atg aac agc ctg gaa cct gaa gac acg gcc gtt tat tac tgt tac      288
Glu Met Asn Ser Leu Glu Pro Glu Asp Thr Ala Val Tyr Tyr Cys Tyr
                 85                  90                  95 act cac tac ttc aga tcc tac tgg ggt cag ggg acc cag gtc acc gtc      336
Thr His Tyr Phe Arg Ser Tyr Trp Gly Gln Gly Thr Gln Val Thr Val
                100                 105                 110 tcc tca                                                              342
Ser Ser <210> SEQ ID NO 18
<211> LENGTH: 114
<212> TYPE: PRT
<213> ORGANISM: Lama peruana

<400> SEQUENCE: 18

Gln Val Gln Leu Gln Glu Ser Gly Gly Gly Leu Val Gln Ala Gly Glu
 1               5                  10                  15

Ser Leu Lys Leu Ser Cys Ala Ala Ser Gly Asn Thr Phe Ser Gly Gly
                 20                  25                  30

Phe Met Gly Trp Tyr Arg Gln Ala Pro Gly Lys Gln Arg Glu Leu Val
             35                  40                  45

Ala Thr Ile Asn Ser Arg Gly Ile Thr Asn Tyr Ala Asp Phe Val Lys
         50                  55                  60

Gly Arg Phe Thr Ile Ser Arg Asp Asn Ala Lys Lys Thr Val Tyr Leu
 65                  70                  75                  80

Glu Met Asn Ser Leu Glu Pro Glu Asp Thr Ala Val Tyr Tyr Cys Tyr
                 85                  90                  95

Thr His Tyr Phe Arg Ser Tyr Trp Gly Gln Gly Thr Gln Val Thr Val
                100                 105                 110

Ser Ser

<210> SEQ ID NO 19
<211> LENGTH: 351
<212> TYPE: DNA
<213> ORGANISM: Lama peruana
<220> FEATURE:
<221> NAME/KEY: CDS
<222> LOCATION: (1)..(351)

<400> SEQUENCE: 19 cag gtg cag ctg cag gag tca ggg gga gga ttg gtg cag gcg ggg ggc       48
Gln Val Gln Leu Gln Glu Ser Gly Gly Gly Leu Val Gln Ala Gly Gly
 1               5                  10                  15 tct ctg aga ctc tcc tgt gca gcc tct gga cgc acc ggc agt acg tat       96
Ser Leu Arg Leu Ser Cys Ala Ala Ser Gly Arg Thr Gly Ser Thr Tyr
                 20                  25                  30 gac atg ggc tgg ttc cgc cag gct cca ggg aag gag cgt gag tct gta      144
Asp Met Gly Trp Phe Arg Gln Ala Pro Gly Lys Glu Arg Glu Ser Val
             35                  40                  45 gca gct att aac tgg gat agt gcg cgc aca tac tat gca agc tcc gtg      192
Ala Ala Ile Asn Trp Asp Ser Ala Arg Thr Tyr Tyr Ala Ser Ser Val
         50                  55                  60 agg ggc cga ttc acc atc tcc aga gac aac gcc aag aag acg gtg tat      240
Arg Gly Arg Phe Thr Ile Ser Arg Asp Asn Ala Lys Lys Thr Val Tyr
 65                  70                  75                  80
```

```
ctg caa atg aac agc ctg aaa cct gag gac acg gcc gtt tat acc tgt       288
Leu Gln Met Asn Ser Leu Lys Pro Glu Asp Thr Ala Val Tyr Thr Cys
                85                  90                  95 ggc gcg ggg gaa ggt ggt act tgg gac tcc tgg ggc cag ggg acc cag       336
Gly Ala Gly Glu Gly Gly Thr Trp Asp Ser Trp Gly Gln Gly Thr Gln
            100                 105                 110 gtc acc gtc tcc tca                                                   351
Val Thr Val Ser Ser
        115
```

<210> SEQ ID NO 20
<211> LENGTH: 117
<212> TYPE: PRT
<213> ORGANISM: Lama peruana

<400> SEQUENCE: 20

```
Gln Val Gln Leu Gln Glu Ser Gly Gly Gly Leu Val Gln Ala Gly Gly
 1               5                  10                  15

Ser Leu Arg Leu Ser Cys Ala Ala Ser Gly Arg Thr Gly Ser Thr Tyr
            20                  25                  30

Asp Met Gly Trp Phe Arg Gln Ala Pro Gly Lys Glu Arg Glu Ser Val
        35                  40                  45

Ala Ala Ile Asn Trp Asp Ser Ala Arg Thr Tyr Tyr Ala Ser Ser Val
    50                  55                  60

Arg Gly Arg Phe Thr Ile Ser Arg Asp Asn Ala Lys Lys Thr Val Tyr
65                  70                  75                  80

Leu Gln Met Asn Ser Leu Lys Pro Glu Asp Thr Ala Val Tyr Thr Cys
                85                  90                  95

Gly Ala Gly Glu Gly Gly Thr Trp Asp Ser Trp Gly Gln Gly Thr Gln
            100                 105                 110

Val Thr Val Ser Ser
        115
```

<210> SEQ ID NO 21
<211> LENGTH: 354
<212> TYPE: DNA
<213> ORGANISM: Lama peruana
<220> FEATURE:
<221> NAME/KEY: CDS
<222> LOCATION: (1)..(354)

<400> SEQUENCE: 21

```
cag gtg cag ctg cag gag tct ggg gga gaa ttg gtg cag cct ggg ggc        48
Gln Val Gln Leu Gln Glu Ser Gly Gly Glu Leu Val Gln Pro Gly Gly
 1               5                  10                  15 tct ctg aaa ctc tcc tgc gca gcc tct gga ctt acc ttc act aat tat       96
Ser Leu Lys Leu Ser Cys Ala Ala Ser Gly Leu Thr Phe Thr Asn Tyr
            20                  25                  30 agc atg ggc tgg ttc cgc cag gct cca gga gtg gac cgt gag gcc gta      144
Ser Met Gly Trp Phe Arg Gln Ala Pro Gly Val Asp Arg Glu Ala Val
        35                  40                  45 gcc gct att agc tgg agt ggt gat aac aca tac tat gta agc tcc gtg      192
Ala Ala Ile Ser Trp Ser Gly Asp Asn Thr Tyr Tyr Val Ser Ser Val
    50                  55                  60 aag gga cga ttc acc atc tcc aga gac aac gcc aag aac acg gtg tat      240
Lys Gly Arg Phe Thr Ile Ser Arg Asp Asn Ala Lys Asn Thr Val Tyr
65                  70                  75                  80 ctg caa atg aac agc ctg aaa cct caa gac acg gcc gtt tat tac tgt      288
Leu Gln Met Asn Ser Leu Lys Pro Gln Asp Thr Ala Val Tyr Tyr Cys
                85                  90                  95
```

```
gca gta aaa ccc gac gat ggt tgg tgg gac tac tgg ggc cag ggg acc    336
Ala Val Lys Pro Asp Asp Gly Trp Trp Asp Tyr Trp Gly Gln Gly Thr
            100                 105                 110 cag gtc acc gtc tcc tca                                             354
Gln Val Thr Val Ser Ser
        115

<210> SEQ ID NO 22
<211> LENGTH: 118
<212> TYPE: PRT
<213> ORGANISM: Lama peruana

<400> SEQUENCE: 22

Gln Val Gln Leu Gln Glu Ser Gly Gly Glu Leu Val Gln Pro Gly Gly
1               5                   10                  15

Ser Leu Lys Leu Ser Cys Ala Ala Ser Gly Leu Thr Phe Thr Asn Tyr
            20                  25                  30

Ser Met Gly Trp Phe Arg Gln Ala Pro Gly Val Asp Arg Glu Ala Val
        35                  40                  45

Ala Ala Ile Ser Trp Ser Gly Asp Asn Thr Tyr Tyr Val Ser Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Gln Asp Thr Ala Val Tyr Tyr Cys
                85                  90                  95

Ala Val Lys Pro Asp Asp Gly Trp Trp Asp Tyr Trp Gly Gln Gly Thr
            100                 105                 110

Gln Val Thr Val Ser Ser
        115

<210> SEQ ID NO 23
<211> LENGTH: 387
<212> TYPE: DNA
<213> ORGANISM: Lama peruana
<220> FEATURE:
<221> NAME/KEY: CDS
<222> LOCATION: (1)..(387)

<400> SEQUENCE: 23 cag gtg cag ctg cag gag tca ggg gga ggc ttg gtg cag cct ggg ggg    48
Gln Val Gln Leu Gln Glu Ser Gly Gly Gly Leu Val Gln Pro Gly Gly
1               5                   10                  15 tct ctg aga ctc tcc tgt gca gcc tct gga ttc gcc ttc aat ctc tac    96
Ser Leu Arg Leu Ser Cys Ala Ala Ser Gly Phe Ala Phe Asn Leu Tyr
            20                  25                  30 tgg atg tat tgg ttc cgt cag gct cca ggg aag gga ctc gag tgg gtc   144
Trp Met Tyr Trp Phe Arg Gln Ala Pro Gly Lys Gly Leu Glu Trp Val
        35                  40                  45 tcg agt gct agt cct ggt aat ggt atc act ttc aat aca ttc tac gcg   192
Ser Ser Ala Ser Pro Gly Asn Gly Ile Thr Phe Asn Thr Phe Tyr Ala
    50                  55                  60 gac tcc gtg aag gga cgg ttc gcc atc tcc aga gac aac gcc aaa aac   240
Asp Ser Val Lys Gly Arg Phe Ala Ile Ser Arg Asp Asn Ala Lys Asn
65                  70                  75                  80 aca ctg tat ctg gag atg aac agt cta caa cct gag gac acg gcc gtg   288
Thr Leu Tyr Leu Glu Met Asn Ser Leu Gln Pro Glu Asp Thr Ala Val
                85                  90                  95 tat tat tgt gct gcc gac ccc tcg tat caa ctc gcg gac ttt ttg act   336
Tyr Tyr Cys Ala Ala Asp Pro Ser Tyr Gln Leu Ala Asp Phe Leu Thr
            100                 105                 110
```

```
tcg ctg ccg aat gac tac tcg ggc cag gga acc cag gtc acc gtc tcc      384
Ser Leu Pro Asn Asp Tyr Ser Gly Gln Gly Thr Gln Val Thr Val Ser
        115                 120                 125 tca                                                                   387
Ser
```

<210> SEQ ID NO 24
<211> LENGTH: 129
<212> TYPE: PRT
<213> ORGANISM: Lama peruana

<400> SEQUENCE: 24

```
Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Ala Phe Asn Leu Tyr
            20                  25                  30

Trp Met Tyr Trp Phe Arg Gln Ala Pro Gly Lys Gly Leu Glu Trp Val
        35                  40                  45

Ser Ser Ala Ser Pro Gly Asn Gly Ile Thr Phe Asn Thr Phe Tyr Ala
    50                  55                  60

Asp Ser Val Lys Gly Arg Phe Ala Ile Ser Arg Asp Asn Ala Lys Asn
 65                 70                  75                  80

Thr Leu Tyr Leu Glu Met Asn Ser Leu Gln Pro Glu Asp Thr Ala Val
                85                  90                  95

Tyr Tyr Cys Ala Ala Asp Pro Ser Tyr Gln Leu Ala Asp Phe Leu Thr
            100                 105                 110

Ser Leu Pro Asn Asp Tyr Ser Gly Gln Gly Thr Gln Val Thr Val Ser
        115                 120                 125

Ser
```

<210> SEQ ID NO 25
<211> LENGTH: 369
<212> TYPE: DNA
<213> ORGANISM: Lama peruana
<220> FEATURE:
<221> NAME/KEY: CDS
<222> LOCATION: (1)..(369)

<400> SEQUENCE: 25

```
cag gtg cag ctg cag gag tca ggg gga gga ctg gtg cag gct ggg gag       48
Gln Val Gln Leu Gln Glu Ser Gly Gly Gly Leu Val Gln Ala Gly Glu
 1               5                  10                  15 agt ctg aga ctc tcc tgt gta gcc tcg ggc ctc tcc ttc agt gaa ttc       96
Ser Leu Arg Leu Ser Cys Val Ala Ser Gly Leu Ser Phe Ser Glu Phe
            20                  25                  30 gtc atg aca tgg ttc cgc cag gct cca ggg aag gag cgt gag ttt gta      144
Val Met Thr Trp Phe Arg Gln Ala Pro Gly Lys Glu Arg Glu Phe Val
        35                  40                  45 gca gcg att aac tgg atg gat gat cgt aca tat tat gga agt tcc gtg      192
Ala Ala Ile Asn Trp Met Asp Asp Arg Thr Tyr Tyr Gly Ser Ser Val
    50                  55                  60 aag ggc cga ttc ttc atc tcc aaa gac aac gcc aag aac aca gtg tat      240
Lys Gly Arg Phe Phe Ile Ser Lys Asp Asn Ala Lys Asn Thr Val Tyr
 65                 70                  75                  80 ctt caa atg aac ggc ctg aaa cct gag gac acg gcc gtt tat tac tgt      288
Leu Gln Met Asn Gly Leu Lys Pro Glu Asp Thr Ala Val Tyr Tyr Cys
                85                  90                  95 gca gcc agt agg gat tac tat ggc cac aat gcc aat cag tat cgc tac      336
Ala Ala Ser Arg Asp Tyr Tyr Gly His Asn Ala Asn Gln Tyr Arg Tyr
```

```
            100                 105                 110
tgg ggc cag ggg acc cag gtc acc gtc tcc tca                              369
Trp Gly Gln Gly Thr Gln Val Thr Val Ser Ser
            115                 120

<210> SEQ ID NO 26
<211> LENGTH: 123
<212> TYPE: PRT
<213> ORGANISM: Lama peruana

<400> SEQUENCE: 26

Gln Val Gln Leu Gln Glu Ser Gly Gly Gly Leu Val Gln Ala Gly Glu
  1               5                  10                  15

Ser Leu Arg Leu Ser Cys Val Ala Ser Gly Leu Ser Phe Ser Glu Phe
             20                  25                  30

Val Met Thr Trp Phe Arg Gln Ala Pro Gly Lys Glu Arg Glu Phe Val
         35                  40                  45

Ala Ala Ile Asn Trp Met Asp Asp Arg Thr Tyr Tyr Gly Ser Ser Val
     50                  55                  60

Lys Gly Arg Phe Phe Ile Ser Lys Asp Asn Ala Lys Asn Thr Val Tyr
 65                  70                  75                  80

Leu Gln Met Asn Gly Leu Lys Pro Glu Asp Thr Ala Val Tyr Tyr Cys
             85                  90                  95

Ala Ala Ser Arg Asp Tyr Tyr Gly His Asn Ala Asn Gln Tyr Arg Tyr
            100                 105                 110

Trp Gly Gln Gly Thr Gln Val Thr Val Ser Ser
            115                 120

<210> SEQ ID NO 27
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 27
gaattaagcg gccgcccagg tgaaactgct cgagtcwggg gga                           43

<210> SEQ ID NO 28
<211> LENGTH: 42
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
tttgttctga ggagacggtg aggagacggt gacctgggtc cc                            42

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: CDS
<222> LOCATION: (1)..(24)

<400> SEQUENCE: 29 cag gtc cag ctg cag gag tct ggg                                          24
Gln Val Gln Leu Gln Glu Ser Gly
  1               5
```

```
<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      amino acid

<400> SEQUENCE: 30

Gln Val Gln Leu Gln Glu Ser Gly
 1               5

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: CDS
<222> LOCATION: (1)..(24)

<400> SEQUENCE: 31 cag gtg aaa ctg ctc gag tcw ggg                              24
Gln Val Lys Leu Leu Glu Ser Gly
 1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      amino acid

<400> SEQUENCE: 32

Gln Val Lys Leu Leu Glu Ser Gly
 1               5

<210> SEQ ID NO 33
<211> LENGTH: 55
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: CDS
<222> LOCATION: (2..40, 47..55)

<400> SEQUENCE: 33 g gtc acc gtc tcc tca cag gtg cag ctg cag gag tca ctg taatga ctt    49
  Val Thr Val Ser Ser Gln Val Gln Leu Gln Glu Ser Leu         Leu
   1               5                   10 aag ctt                                                      55
Lys Leu
 15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      amino acid

<400> SEQUENCE: 34

Val Thr Val Ser Ser Gln Val Gln Leu Gln Glu Ser Leu Leu Lys Leu
```

<210> SEQ ID NO 35
<211> LENGTH: 714
<212> TYPE: DNA
<213> ORGANISM: Unknown Organism
<220> FEATURE:
<223> OTHER INFORMATION: Description of Unknown Organism: Nucleotide
sequence within plasmid pUR4618 which encodes an
anti-hcg anti-RR6 bispecific biheaded antigen
binding protein
<221> NAME/KEY: CDS
<222> LOCATION: (1)..(714)

<400> SEQUENCE: 35

```
ctc gag tca ggg gga gga ttg gtg cag gcg ggg ggc tct ctg aga ctc      48
Leu Glu Ser Gly Gly Gly Leu Val Gln Ala Gly Gly Ser Leu Arg Leu
  1               5                  10                  15 tcc tgt gca gcc tct gga cgc acc ggc agt acg tat gac atg ggc tgg      96
Ser Cys Ala Ala Ser Gly Arg Thr Gly Ser Thr Tyr Asp Met Gly Trp
             20                  25                  30 ttc cgc cag gct cca ggg aag gag cgt gag tct gta gca gct att aac     144
Phe Arg Gln Ala Pro Gly Lys Glu Arg Glu Ser Val Ala Ala Ile Asn
         35                  40                  45 tgg gat agt gcg cgc aca tac tat gca agc tcc gtg agg ggc cga ttc     192
Trp Asp Ser Ala Arg Thr Tyr Tyr Ala Ser Ser Val Arg Gly Arg Phe
     50                  55                  60 acc atc tcc aga gac aac gcc aag aag acg gtg tat ctg caa atg aac     240
Thr Ile Ser Arg Asp Asn Ala Lys Lys Thr Val Tyr Leu Gln Met Asn
 65                  70                  75                  80 agc ctg aaa cct gag gac acg gcc gtt tat acc tgt ggc gcg ggg gaa     288
Ser Leu Lys Pro Glu Asp Thr Ala Val Tyr Thr Cys Gly Ala Gly Glu
                 85                  90                  95 ggt ggt act tgg gac tcc tgg ggc cag ggg acc cag gtc acc gtc tcc     336
Gly Gly Thr Trp Asp Ser Trp Gly Gln Gly Thr Gln Val Thr Val Ser
            100                 105                 110 tca cag gtg cag ctg cag gag tca ggg gga gga ttg gtg cag gct ggg     384
Ser Gln Val Gln Leu Gln Glu Ser Gly Gly Gly Leu Val Gln Ala Gly
        115                 120                 125 gac tct ctg aga ctc tcc tgc gcg gcc tcg gga cgc act tct cat ggg     432
Asp Ser Leu Arg Leu Ser Cys Ala Ala Ser Gly Arg Thr Ser His Gly
    130                 135                 140 tat ggt ggc tat ggc atg ggc tgg ttc cgc caa att cca ggg aag gag     480
Tyr Gly Gly Tyr Gly Met Gly Trp Phe Arg Gln Ile Pro Gly Lys Glu
145                 150                 155                 160 cgt gag ctt gtc gca gca att agg tgg agc ggt cgt aat aca tac tat     528
Arg Glu Leu Val Ala Ala Ile Arg Trp Ser Gly Arg Asn Thr Tyr Tyr
                165                 170                 175 gca gac tcc gtg aag ggc cga ttc acc atc tcc aga gac aac gtc aag     576
Ala Asp Ser Val Lys Gly Arg Phe Thr Ile Ser Arg Asp Asn Val Lys
            180                 185                 190 gac atg ctg tat ctg caa atg aac agt ttg aaa cct gag gac acg gcc     624
Asp Met Leu Tyr Leu Gln Met Asn Ser Leu Lys Pro Glu Asp Thr Ala
        195                 200                 205 gtt tac act tgt gca gtt cgg acg gtc cgc gtg gtt gac att tcc agt     672
Val Tyr Thr Cys Ala Val Arg Thr Val Arg Val Val Asp Ile Ser Ser
    210                 215                 220 ccg gtt ggg ttt gcc tac tgg ggc cag ggg acc cag gtc acc                714
Pro Val Gly Phe Ala Tyr Trp Gly Gln Gly Thr Gln Val Thr
225                 230                 235
```

<210> SEQ ID NO 36

```
<211> LENGTH: 238
<212> TYPE: PRT
<213> ORGANISM: Unknown Organism
<220> FEATURE:
<223> OTHER INFORMATION: Description of Unknown Organism: Bispecific
      biheaded antigen binding protein

<400> SEQUENCE: 36

Leu Glu Ser Gly Gly Gly Leu Val Gln Ala Gly Gly Ser Leu Arg Leu
  1               5                  10                  15

Ser Cys Ala Ala Ser Gly Arg Thr Gly Ser Thr Tyr Asp Met Gly Trp
                 20                  25                  30

Phe Arg Gln Ala Pro Gly Lys Glu Arg Glu Ser Val Ala Ala Ile Asn
             35                  40                  45

Trp Asp Ser Ala Arg Thr Tyr Tyr Ala Ser Ser Val Arg Gly Arg Phe
     50                  55                  60

Thr Ile Ser Arg Asp Asn Ala Lys Lys Thr Val Tyr Leu Gln Met Asn
 65                  70                  75                  80

Ser Leu Lys Pro Glu Asp Thr Ala Val Tyr Thr Cys Gly Ala Gly Glu
                 85                  90                  95

Gly Gly Thr Trp Asp Ser Trp Gly Gln Gly Thr Gln Val Thr Val Ser
            100                 105                 110

Ser Gln Val Gln Leu Gln Glu Ser Gly Gly Gly Leu Val Gln Ala Gly
            115                 120                 125

Asp Ser Leu Arg Leu Ser Cys Ala Ala Ser Gly Arg Thr Ser His Gly
        130                 135                 140

Tyr Gly Tyr Gly Met Gly Trp Phe Arg Gln Ile Pro Gly Lys Glu
145                 150                 155                 160

Arg Glu Leu Val Ala Ala Ile Arg Trp Ser Gly Arg Asn Thr Tyr Tyr
                165                 170                 175

Ala Asp Ser Val Lys Gly Arg Phe Thr Ile Ser Arg Asp Asn Val Lys
            180                 185                 190

Asp Met Leu Tyr Leu Gln Met Asn Ser Leu Lys Pro Glu Asp Thr Ala
        195                 200                 205

Val Tyr Thr Cys Ala Val Arg Thr Val Arg Val Val Asp Ile Ser Ser
    210                 215                 220

Pro Val Gly Phe Ala Tyr Trp Gly Gln Gly Thr Gln Val Thr
225                 230                 235

<210> SEQ ID NO 37
<211> LENGTH: 672
<212> TYPE: DNA
<213> ORGANISM: Unknown Organism
<220> FEATURE:
<223> OTHER INFORMATION: Description of Unknown Organism: Nucleotide
      sequence within plasmid pUR4619, which encodes an
      anti-hGC-anti-RR6 bispecific biheaded antigen
      binding protein
<221> NAME/KEY: CDS
<222> LOCATION: (1)..(672)

<400> SEQUENCE: 37 ctc gag tca ggg gga gga ttg gtg cag gcg ggg ggc tct ctg aga ctc      48
Leu Glu Ser Gly Gly Gly Leu Val Gln Ala Gly Gly Ser Leu Arg Leu
  1               5                  10                  15 tcc tgt gca gcc tct gga cgc acc ggc agt acg tat gac atg ggc tgg      96
Ser Cys Ala Ala Ser Gly Arg Thr Gly Ser Thr Tyr Asp Met Gly Trp
                 20                  25                  30 ttc cgc cag gct cca ggg aag gag cgt gag tct gta gca gct att aac     144
Phe Arg Gln Ala Pro Gly Lys Glu Arg Glu Ser Val Ala Ala Ile Asn
```

|  |  |  |  |  |  |  |  |  |  |  |  |  |  |  |  |
|---|---|---|---|---|---|---|---|---|---|---|---|---|---|---|---|
|  |  | 35 |  |  |  | 40 |  |  |  |  | 45 |  |  |  |  |
| tgg | gat | agt | gcg | cgc | aca | tac | tat | gca | agc | tcc | gtg | agg | ggc | cga | ttc | 192 |
| Trp | Asp | Ser | Ala | Arg | Thr | Tyr | Tyr | Ala | Ser | Ser | Val | Arg | Gly | Arg | Phe |  |
|  | 50 |  |  |  | 55 |  |  |  | 60 |  |  |  |  |  |  |
| acc | atc | tcc | aga | gac | aac | gcc | aag | aag | acg | gtg | tat | ctg | caa | atg | aac | 240 |
| Thr | Ile | Ser | Arg | Asp | Asn | Ala | Lys | Lys | Thr | Val | Tyr | Leu | Gln | Met | Asn |  |
| 65 |  |  |  | 70 |  |  |  |  | 75 |  |  |  |  | 80 |  |
| agc | ctg | aaa | cct | gag | gac | acg | gcc | gtt | tat | acc | tgt | ggc | gcg | ggg | gaa | 288 |
| Ser | Leu | Lys | Pro | Glu | Asp | Thr | Ala | Val | Tyr | Thr | Cys | Gly | Ala | Gly | Glu |  |
|  |  |  |  | 85 |  |  |  |  | 90 |  |  |  |  | 95 |  |
| ggt | ggt | act | tgg | gac | tcc | tgg | ggc | cag | ggg | acc | cag | gtc | acc | gtc | tcc | 336 |
| Gly | Gly | Thr | Trp | Asp | Ser | Trp | Gly | Gln | Gly | Thr | Gln | Val | Thr | Val | Ser |  |
|  |  |  | 100 |  |  |  | 105 |  |  |  | 110 |  |  |  |  |
| tca | cag | gtg | cag | ctg | cag | gag | tca | ggg | gga | ggc | ttg | gtg | cag | gct | ggg | 384 |
| Ser | Gln | Val | Gln | Leu | Gln | Glu | Ser | Gly | Gly | Gly | Leu | Val | Gln | Ala | Gly |  |
|  |  | 115 |  |  |  | 120 |  |  |  |  | 125 |  |  |  |  |
| gag | tct | ctg | aaa | ctc | tcc | tgt | gca | gcc | tct | gga | aac | acc | ttc | agt | ggc | 432 |
| Glu | Ser | Leu | Lys | Leu | Ser | Cys | Ala | Ala | Ser | Gly | Asn | Thr | Phe | Ser | Gly |  |
|  | 130 |  |  |  | 135 |  |  |  | 140 |  |  |  |  |  |  |
| ggc | ttc | atg | ggc | tgg | tac | cgc | cag | gct | cca | ggg | aag | cag | cgc | gag | ttg | 480 |
| Gly | Phe | Met | Gly | Trp | Tyr | Arg | Gln | Ala | Pro | Gly | Lys | Gln | Arg | Glu | Leu |  |
| 145 |  |  |  | 150 |  |  |  |  | 155 |  |  |  |  | 160 |  |
| gtc | gca | acc | att | aat | agt | aga | ggt | atc | aca | aac | tat | gca | gac | ttc | gtg | 528 |
| Val | Ala | Thr | Ile | Asn | Ser | Arg | Gly | Ile | Thr | Asn | Tyr | Ala | Asp | Phe | Val |  |
|  |  |  |  | 165 |  |  |  |  | 170 |  |  |  |  | 175 |  |
| aag | ggc | cga | ttc | acc | atc | tcc | aga | gac | aat | gcc | aag | aag | aca | gtg | tat | 576 |
| Lys | Gly | Arg | Phe | Thr | Ile | Ser | Arg | Asp | Asn | Ala | Lys | Lys | Thr | Val | Tyr |  |
|  |  |  | 180 |  |  |  | 185 |  |  |  | 190 |  |  |  |  |
| ttg | gaa | atg | aac | agc | ctg | gaa | cct | gaa | gac | acg | gcc | gtt | tat | tac | tgt | 624 |
| Leu | Glu | Met | Asn | Ser | Leu | Glu | Pro | Glu | Asp | Thr | Ala | Val | Tyr | Tyr | Cys |  |
|  |  | 195 |  |  |  | 200 |  |  |  |  | 205 |  |  |  |  |
| tac | act | cac | tac | ttc | aga | tcc | tac | tgg | ggt | cag | ggg | acc | cag | gtc | acc | 672 |
| Tyr | Thr | His | Tyr | Phe | Arg | Ser | Tyr | Trp | Gly | Gln | Gly | Thr | Gln | Val | Thr |  |
|  | 210 |  |  |  | 215 |  |  |  | 220 |  |  |  |  |  |  |

<210> SEQ ID NO 38
<211> LENGTH: 224
<212> TYPE: PRT
<213> ORGANISM: Unknown Organism
<220> FEATURE:
<223> OTHER INFORMATION: Description of Unknown Organism: Bispecific
      biheaded antigen binding protein

<400> SEQUENCE: 38

Leu Glu Ser Gly Gly Gly Leu Val Gln Ala Gly Gly Ser Leu Arg Leu
 1               5                  10                  15

Ser Cys Ala Ala Ser Gly Arg Thr Gly Ser Thr Tyr Asp Met Gly Trp
                20                  25                  30

Phe Arg Gln Ala Pro Gly Lys Glu Arg Glu Ser Val Ala Ala Ile Asn
            35                  40                  45

Trp Asp Ser Ala Arg Thr Tyr Tyr Ala Ser Ser Val Arg Gly Arg Phe
        50                  55                  60

Thr Ile Ser Arg Asp Asn Ala Lys Lys Thr Val Tyr Leu Gln Met Asn
 65                  70                  75                  80

Ser Leu Lys Pro Glu Asp Thr Ala Val Tyr Thr Cys Gly Ala Gly Glu
                85                  90                  95

Gly Gly Thr Trp Asp Ser Trp Gly Gln Gly Thr Gln Val Thr Val Ser
            100                 105                 110

Ser Gln Val Gln Leu Gln Glu Ser Gly Gly Gly Leu Val Gln Ala Gly

```
                 115                 120                  125
Glu Ser Leu Lys Leu Ser Cys Ala Ala Ser Gly Asn Thr Phe Ser Gly
    130                 135                 140

Gly Phe Met Gly Trp Tyr Arg Gln Ala Pro Gly Lys Gln Arg Glu Leu
145                 150                 155                 160

Val Ala Thr Ile Asn Ser Arg Gly Ile Thr Asn Tyr Ala Asp Phe Val
                165                 170                 175

Lys Gly Arg Phe Thr Ile Ser Arg Asp Asn Ala Lys Lys Thr Val Tyr
            180                 185                 190

Leu Glu Met Asn Ser Leu Glu Pro Glu Asp Thr Ala Val Tyr Tyr Cys
        195                 200                 205

Tyr Thr His Tyr Phe Arg Ser Tyr Trp Gly Gln Gly Thr Gln Val Thr
    210                 215                 220
```

<210> SEQ ID NO 39
<211> LENGTH: 717
<212> TYPE: DNA
<213> ORGANISM: Unknown Organism
<220> FEATURE:
<223> OTHER INFORMATION: Description of Unknown Organism: Nucleotide
      sequence within plasmid pUR4620, which encodes an
      anti-hCG-anti-RR6 bispecific biheaded antigen
      binding protein
<221> NAME/KEY: CDS
<222> LOCATION: (1)..(717)

<400> SEQUENCE: 39

```
ctc gag tct ggg gga gaa ttg gtg cag cct ggg ggc tct ctg aaa ctc      48
Leu Glu Ser Gly Gly Glu Leu Val Gln Pro Gly Gly Ser Leu Lys Leu
  1               5                  10                  15 tcc tgc gca gcc tct gga ctt acc ttc act aat tat agc atg ggc tgg      96
Ser Cys Ala Ala Ser Gly Leu Thr Phe Thr Asn Tyr Ser Met Gly Trp
             20                  25                  30 ttc cgc cca ggt cca gga gtg gac cgt gag gcc gta gcc gct att agc     144
Phe Arg Pro Gly Pro Gly Val Asp Arg Glu Ala Val Ala Ala Ile Ser
         35                  40                  45 tgg agt ggt gat aac aca tac tat gta agc tcc gtg aag gga cga ttc     192
Trp Ser Gly Asp Asn Thr Tyr Tyr Val Ser Ser Val Lys Gly Arg Phe
     50                  55                  60 acc atc tcc aga gac aac gcc aag aac acg gtg tat ctg caa atg aac     240
Thr Ile Ser Arg Asp Asn Ala Lys Asn Thr Val Tyr Leu Gln Met Asn
 65                  70                  75                  80 agc ctg aaa cct caa gac acg gcc gtt tat tac tgt gca gta aaa ccc     288
Ser Leu Lys Pro Gln Asp Thr Ala Val Tyr Tyr Cys Ala Val Lys Pro
                 85                  90                  95 gac gat ggt tgg tgg gac tac tgg ggc cag ggg acc cag gtc acc gtc     336
Asp Asp Gly Trp Trp Asp Tyr Trp Gly Gln Gly Thr Gln Val Thr Val
            100                 105                 110 tcc tca cag gtg cag ctg cag gag tca ggg gga gga ttg gtg cag gct     384
Ser Ser Gln Val Gln Leu Gln Glu Ser Gly Gly Gly Leu Val Gln Ala
        115                 120                 125 ggg gac tct ctg aga ctc tcc tgc gcg gcc tcg gga cgc act tct cat     432
Gly Asp Ser Leu Arg Leu Ser Cys Ala Ala Ser Gly Arg Thr Ser His
    130                 135                 140 ggg tat ggt ggc tat ggc atg ggc tgg ttc cgc caa att cca ggg aag     480
Gly Tyr Gly Gly Tyr Gly Met Gly Trp Phe Arg Gln Ile Pro Gly Lys
145                 150                 155                 160 gag cgt gag ctt gtc gca gca att agg tgg agc ggt cgt aat aca tac     528
Glu Arg Glu Leu Val Ala Ala Ile Arg Trp Ser Gly Arg Asn Thr Tyr

```
tat gca gac tcc gtg aag ggc cga ttc acc atc tcc aga gac aac gtc      576
Tyr Ala Asp Ser Val Lys Gly Arg Phe Thr Ile Ser Arg Asp Asn Val
        180                 185                 190 aag gac atg ctg tat ctg caa atg aac agt ttg aaa cct gag gac acg      624
Lys Asp Met Leu Tyr Leu Gln Met Asn Ser Leu Lys Pro Glu Asp Thr
            195                 200                 205 gcc gtt tac act tgt gca gtt cgg acg gtc cgc gtg gtt gac att tcc      672
Ala Val Tyr Thr Cys Ala Val Arg Thr Val Arg Val Val Asp Ile Ser
        210                 215                 220 agt ccg gtt ggg ttt gcc tac tgg ggc cag ggg acc cag gtc acc          717
Ser Pro Val Gly Phe Ala Tyr Trp Gly Gln Gly Thr Gln Val Thr
225                 230                 235
```

<210> SEQ ID NO 40
<211> LENGTH: 239
<212> TYPE: PRT
<213> ORGANISM: Unknown Organism
<220> FEATURE:
<223> OTHER INFORMATION: Description of Unknown Organism: Bispecific
      biheaded antigen binding protein

<400> SEQUENCE: 40

```
Leu Glu Ser Gly Gly Glu Leu Val Gln Pro Gly Gly Ser Leu Lys Leu
 1               5                   10                  15

Ser Cys Ala Ala Ser Gly Leu Thr Phe Thr Asn Tyr Ser Met Gly Trp
            20                  25                  30

Phe Arg Pro Gly Pro Gly Val Asp Arg Glu Ala Val Ala Ala Ile Ser
        35                  40                  45

Trp Ser Gly Asp Asn Thr Tyr Tyr Val Ser Ser Val Lys Gly Arg Phe
    50                  55                  60

Thr Ile Ser Arg Asp Asn Ala Lys Asn Thr Val Tyr Leu Gln Met Asn
65                  70                  75                  80

Ser Leu Lys Pro Gln Asp Thr Ala Val Tyr Tyr Cys Ala Val Lys Pro
                85                  90                  95

Asp Asp Gly Trp Trp Asp Tyr Trp Gly Gln Gly Thr Gln Val Thr Val
            100                 105                 110

Ser Ser Gln Val Gln Leu Gln Glu Ser Gly Gly Gly Leu Val Gln Ala
        115                 120                 125

Gly Asp Ser Leu Arg Leu Ser Cys Ala Ala Ser Gly Arg Thr Ser His
    130                 135                 140

Gly Tyr Gly Gly Tyr Gly Met Gly Trp Phe Arg Gln Ile Pro Gly Lys
145                 150                 155                 160

Glu Arg Glu Leu Val Ala Ala Ile Arg Trp Ser Gly Arg Asn Thr Tyr
                165                 170                 175

Tyr Ala Asp Ser Val Lys Gly Arg Phe Thr Ile Ser Arg Asp Asn Val
            180                 185                 190

Lys Asp Met Leu Tyr Leu Gln Met Asn Ser Leu Lys Pro Glu Asp Thr
        195                 200                 205

Ala Val Tyr Thr Cys Ala Val Arg Thr Val Arg Val Val Asp Ile Ser
    210                 215                 220

Ser Pro Val Gly Phe Ala Tyr Trp Gly Gln Gly Thr Gln Val Thr
225                 230                 235
```

<210> SEQ ID NO 41
<211> LENGTH: 675
<212> TYPE: DNA
<213> ORGANISM: Unknown Organism
<220> FEATURE:
<223> OTHER INFORMATION: Description of Unknown Organism: Nucleotide sequence within plasmid pUR4621, which encodes an
anti-hCG-anti-RR6 bispecific biheaded antigen
binding protein
<221> NAME/KEY: CDS
<222> LOCATION: (1)..(675)

<400> SEQUENCE: 41

| | | | | | | | | | | | | | | | | |
|---|---|---|---|---|---|---|---|---|---|---|---|---|---|---|---|---|
| ctc | gag | tct | ggg | gga | gaa | ttg | gtg | cag | cct | ggg | ggc | tct | ctg | aaa | ctc | 48 |
| Leu | Glu | Ser | Gly | Gly | Glu | Leu | Val | Gln | Pro | Gly | Gly | Ser | Leu | Lys | Leu | |
| 1 | | | | 5 | | | | | 10 | | | | | 15 | | |
| tcc | tgc | gca | gcc | tct | gga | ctt | acc | ttc | act | aat | tat | agc | atg | ggc | tgg | 96 |
| Ser | Cys | Ala | Ala | Ser | Gly | Leu | Thr | Phe | Thr | Asn | Tyr | Ser | Met | Gly | Trp | |
| | | | 20 | | | | | 25 | | | | | 30 | | | |
| ttc | cgc | cca | ggt | cca | gga | gtg | gac | cgt | gag | gcc | gta | gcc | gct | att | agc | 144 |
| Phe | Arg | Pro | Gly | Pro | Gly | Val | Asp | Arg | Glu | Ala | Val | Ala | Ala | Ile | Ser | |
| | | 35 | | | | | 40 | | | | | 45 | | | | |
| tgg | agt | ggt | gat | aac | aca | tac | tat | gta | agc | tcc | gtg | aag | gga | cga | ttc | 192 |
| Trp | Ser | Gly | Asp | Asn | Thr | Tyr | Tyr | Val | Ser | Ser | Val | Lys | Gly | Arg | Phe | |
| | 50 | | | | | 55 | | | | | 60 | | | | | |
| acc | atc | tcc | aga | gac | aac | gcc | aag | aac | acg | gtg | tat | ctg | caa | atg | aac | 240 |
| Thr | Ile | Ser | Arg | Asp | Asn | Ala | Lys | Asn | Thr | Val | Tyr | Leu | Gln | Met | Asn | |
| 65 | | | | | 70 | | | | | 75 | | | | | 80 | |
| agc | ctg | aaa | cct | caa | gac | acg | gcc | gtt | tat | tac | tgt | gca | gta | aaa | ccc | 288 |
| Ser | Leu | Lys | Pro | Gln | Asp | Thr | Ala | Val | Tyr | Tyr | Cys | Ala | Val | Lys | Pro | |
| | | | 85 | | | | | 90 | | | | | 95 | | | |
| gac | gat | ggt | tgg | tgg | gac | tac | tgg | ggc | cag | ggg | acc | cag | gtc | acc | gtc | 336 |
| Asp | Asp | Gly | Trp | Trp | Asp | Tyr | Trp | Gly | Gln | Gly | Thr | Gln | Val | Thr | Val | |
| | | 100 | | | | | 105 | | | | | 110 | | | | |
| tcc | tca | cag | gtg | cag | ctg | cag | gag | tca | ggg | gga | ggc | ttg | gtg | cag | gct | 384 |
| Ser | Ser | Gln | Val | Gln | Leu | Gln | Glu | Ser | Gly | Gly | Gly | Leu | Val | Gln | Ala | |
| | 115 | | | | | 120 | | | | | 125 | | | | | |
| ggg | gag | tct | ctg | aaa | ctc | tcc | tgt | gca | gcc | tct | gga | aac | acc | ttc | agt | 432 |
| Gly | Glu | Ser | Leu | Lys | Leu | Ser | Cys | Ala | Ala | Ser | Gly | Asn | Thr | Phe | Ser | |
| 130 | | | | | 135 | | | | | 140 | | | | | | |
| ggc | ggc | ttc | atg | ggc | tgg | tac | cgc | cag | gct | cca | ggg | aag | cag | cgc | gag | 480 |
| Gly | Gly | Phe | Met | Gly | Trp | Tyr | Arg | Gln | Ala | Pro | Gly | Lys | Gln | Arg | Glu | |
| 145 | | | | | 150 | | | | | 155 | | | | | 160 | |
| ttg | gtc | gca | acc | att | aat | agt | aga | ggt | atc | aca | aac | tat | gca | gac | ttc | 528 |
| Leu | Val | Ala | Thr | Ile | Asn | Ser | Arg | Gly | Ile | Thr | Asn | Tyr | Ala | Asp | Phe | |
| | | | 165 | | | | | 170 | | | | | 175 | | | |
| gtg | aag | ggc | cga | ttc | acc | atc | tcc | aga | gac | aat | gcc | aag | aag | aca | gtg | 576 |
| Val | Lys | Gly | Arg | Phe | Thr | Ile | Ser | Arg | Asp | Asn | Ala | Lys | Lys | Thr | Val | |
| | | 180 | | | | | 185 | | | | | 190 | | | | |
| tat | ttg | gaa | atg | aac | agc | ctg | gaa | cct | gaa | gac | acg | gcc | gtt | tat | tac | 624 |
| Tyr | Leu | Glu | Met | Asn | Ser | Leu | Glu | Pro | Glu | Asp | Thr | Ala | Val | Tyr | Tyr | |
| | 195 | | | | | 200 | | | | | 205 | | | | | |
| tgt | tac | act | cac | tac | ttc | aga | tcc | tac | tgg | ggt | cag | ggg | acc | cag | gtc | 672 |
| Cys | Tyr | Thr | His | Tyr | Phe | Arg | Ser | Tyr | Trp | Gly | Gln | Gly | Thr | Gln | Val | |
| 210 | | | | | 215 | | | | | 220 | | | | | | |
| acc | | | | | | | | | | | | | | | | 675 |
| Thr | | | | | | | | | | | | | | | | |
| 225 | | | | | | | | | | | | | | | | |

<210> SEQ ID NO 42
<211> LENGTH: 225
<212> TYPE: PRT
<213> ORGANISM: Unknown Organism
<220> FEATURE:
<223> OTHER INFORMATION: Description of Unknown Organism: Bispecific
      biheaded antigen binding protein

<400> SEQUENCE: 42

-continued

```
Leu Glu Ser Gly Gly Glu Leu Val Gln Pro Gly Gly Ser Leu Lys Leu
  1               5                  10                  15

Ser Cys Ala Ala Ser Gly Leu Thr Phe Thr Asn Tyr Ser Met Gly Trp
             20                  25                  30

Phe Arg Pro Gly Pro Gly Val Asp Arg Glu Ala Val Ala Ala Ile Ser
         35                  40                  45

Trp Ser Gly Asp Asn Thr Tyr Tyr Val Ser Ser Val Lys Gly Arg Phe
     50                  55                  60

Thr Ile Ser Arg Asp Asn Ala Lys Asn Thr Val Tyr Leu Gln Met Asn
 65                  70                  75                  80

Ser Leu Lys Pro Gln Asp Thr Ala Val Tyr Tyr Cys Ala Val Lys Pro
                 85                  90                  95

Asp Asp Gly Trp Trp Asp Tyr Trp Gly Gln Gly Thr Gln Val Thr Val
            100                 105                 110

Ser Ser Gln Val Gln Leu Gln Glu Ser Gly Gly Gly Leu Val Gln Ala
        115                 120                 125

Gly Glu Ser Leu Lys Leu Ser Cys Ala Ala Ser Gly Asn Thr Phe Ser
    130                 135                 140

Gly Gly Phe Met Gly Trp Tyr Arg Gln Ala Pro Gly Lys Gln Arg Glu
145                 150                 155                 160

Leu Val Ala Thr Ile Asn Ser Arg Gly Ile Thr Asn Tyr Ala Asp Phe
                165                 170                 175

Val Lys Gly Arg Phe Thr Ile Ser Arg Asp Asn Ala Lys Lys Thr Val
            180                 185                 190

Tyr Leu Glu Met Asn Ser Leu Glu Pro Glu Asp Thr Ala Val Tyr Tyr
        195                 200                 205

Cys Tyr Thr His Tyr Phe Arg Ser Tyr Trp Gly Gln Gly Thr Gln Val
    210                 215                 220

Thr
225

<210> SEQ ID NO 43
<211> LENGTH: 750
<212> TYPE: DNA
<213> ORGANISM: Unknown Organism
<220> FEATURE:
<223> OTHER INFORMATION: Description of Unknown Organism: Nucleotide
      sequence within plasmid pUR4622, which encodes a
      homodimeric bivalent anti-RR6 antigen binding
      protein
<221> NAME/KEY: CDS
<222> LOCATION: (1)..(750)

<400> SEQUENCE: 43 ctg cag gag tca ggg gga gga ttg gtg cag gct ggg gac tct ctg aga       48
Leu Gln Glu Ser Gly Gly Gly Leu Val Gln Ala Gly Asp Ser Leu Arg
  1               5                  10                  15 ctc tcc tgc gcg gcc tcg gga cgc act tct cat ggg tat ggt ggc tat       96
Leu Ser Cys Ala Ala Ser Gly Arg Thr Ser His Gly Tyr Gly Gly Tyr
             20                  25                  30 ggc atg ggc tgg ttc cgc caa att cca ggg aag gag cgt gag ctt gtc      144
Gly Met Gly Trp Phe Arg Gln Ile Pro Gly Lys Glu Arg Glu Leu Val
         35                  40                  45 gca gca att agg tgg agc ggt cgt aat aca tac tat gca gac tcc gtg      192
Ala Ala Ile Arg Trp Ser Gly Arg Asn Thr Tyr Tyr Ala Asp Ser Val
     50                  55                  60 aag ggc cga ttc acc atc tcc aga gac aac gtc aag gac atg ctg tat      240
Lys Gly Arg Phe Thr Ile Ser Arg Asp Asn Val Lys Asp Met Leu Tyr
 65                  70                  75                  80
```

-continued

```
ctg caa atg aac agt ttg aaa cct gag gac acg gcc gtt tac act tgt      288
Leu Gln Met Asn Ser Leu Lys Pro Glu Asp Thr Ala Val Tyr Thr Cys
                 85                  90                  95 gca gtt cgg acg gtc cgc gtg gtt gac att tcc agt ccg gtt ggg ttt      336
Ala Val Arg Thr Val Arg Val Val Asp Ile Ser Ser Pro Val Gly Phe
            100                 105                 110 gcc tac tgg ggc cag ggg acc cag gtc acc gtc tcc tca cag gtg cag      384
Ala Tyr Trp Gly Gln Gly Thr Gln Val Thr Val Ser Ser Gln Val Gln
        115                 120                 125 ctg cag gag tca ggg gga gga ttg gtg cag gct ggg gac tct ctg aga      432
Leu Gln Glu Ser Gly Gly Gly Leu Val Gln Ala Gly Asp Ser Leu Arg
    130                 135                 140 ctc tcc tgc gcg gcc tcg gga cgc act tct cat ggg tat ggt ggc tat      480
Leu Ser Cys Ala Ala Ser Gly Arg Thr Ser His Gly Tyr Gly Gly Tyr
145                 150                 155                 160 ggc atg ggc tgg ttc cgc caa att cca ggg aag gag cgt gag ctt gtc      528
Gly Met Gly Trp Phe Arg Gln Ile Pro Gly Lys Glu Arg Glu Leu Val
                165                 170                 175 gca gca att agg tgg agc ggt cgt aat aca tac tat gca gac tcc gtg      576
Ala Ala Ile Arg Trp Ser Gly Arg Asn Thr Tyr Tyr Ala Asp Ser Val
            180                 185                 190 aag ggc cga ttc acc atc tcc aga gac aac gtc aag gac atg ctg tat      624
Lys Gly Arg Phe Thr Ile Ser Arg Asp Asn Val Lys Asp Met Leu Tyr
        195                 200                 205 ctg caa atg aac agt ttg aaa cct gag gac acg gcc gtt tac act tgt      672
Leu Gln Met Asn Ser Leu Lys Pro Glu Asp Thr Ala Val Tyr Thr Cys
    210                 215                 220 gca gtt cgg acg gtc cgc gtg gtt gac att tcc agt ccg gtt ggg ttt      720
Ala Val Arg Thr Val Arg Val Val Asp Ile Ser Ser Pro Val Gly Phe
225                 230                 235                 240 gcc tac tgg ggc cag ggg acc cag gtc acc                              750
Ala Tyr Trp Gly Gln Gly Thr Gln Val Thr
                245                 250

<210> SEQ ID NO 44
<211> LENGTH: 250
<212> TYPE: PRT
<213> ORGANISM: Unknown Organism
<220> FEATURE:
<223> OTHER INFORMATION: Description of Unknown Organism: A homodimeric
      bivalent anti-RR6 antigen binding protein

<400> SEQUENCE: 44

Leu Gln Glu Ser Gly Gly Gly Leu Val Gln Ala Gly Asp Ser Leu Arg
  1               5                  10                  15

Leu Ser Cys Ala Ala Ser Gly Arg Thr Ser His Gly Tyr Gly Gly Tyr
             20                  25                  30

Gly Met Gly Trp Phe Arg Gln Ile Pro Gly Lys Glu Arg Glu Leu Val
         35                  40                  45

Ala Ala Ile Arg Trp Ser Gly Arg Asn Thr Tyr Tyr Ala Asp Ser Val
     50                  55                  60

Lys Gly Arg Phe Thr Ile Ser Arg Asp Asn Val Lys Asp Met Leu Tyr
 65                  70                  75                  80

Leu Gln Met Asn Ser Leu Lys Pro Glu Asp Thr Ala Val Tyr Thr Cys
                 85                  90                  95

Ala Val Arg Thr Val Arg Val Val Asp Ile Ser Ser Pro Val Gly Phe
            100                 105                 110

Ala Tyr Trp Gly Gln Gly Thr Gln Val Thr Val Ser Ser Gln Val Gln
        115                 120                 125
```

-continued

```
Leu Gln Glu Ser Gly Gly Gly Leu Val Gln Ala Gly Asp Ser Leu Arg
    130                 135                 140

Leu Ser Cys Ala Ala Ser Gly Arg Thr Ser His Gly Tyr Gly Gly Tyr
145                 150                 155                 160

Gly Met Gly Trp Phe Arg Gln Ile Pro Gly Lys Glu Arg Glu Leu Val
                165                 170                 175

Ala Ala Ile Arg Trp Ser Gly Arg Asn Thr Tyr Tyr Ala Asp Ser Val
            180                 185                 190

Lys Gly Arg Phe Thr Ile Ser Arg Asp Asn Val Lys Asp Met Leu Tyr
        195                 200                 205

Leu Gln Met Asn Ser Leu Lys Pro Glu Asp Thr Ala Val Tyr Thr Cys
    210                 215                 220

Ala Val Arg Thr Val Arg Val Val Asp Ile Ser Ser Pro Val Gly Phe
225                 230                 235                 240

Ala Tyr Trp Gly Gln Gly Thr Gln Val Thr
                245                 250

<210> SEQ ID NO 45
<211> LENGTH: 708
<212> TYPE: DNA
<213> ORGANISM: Unknown Organism
<220> FEATURE:
<223> OTHER INFORMATION: Description of Unknown Organism: Nucleotide
      sequence within plasmid pUR4623, which encodes a
      heterodimeric bivalent anti-RR6 antigen binding
      protein
<221> NAME/KEY: CDS
<222> LOCATION: (1)..(708)

<400> SEQUENCE: 45 ctg cag gag tca ggg gga gga ttg gtg cag gct ggg gac tct ctg aga       48
Leu Gln Glu Ser Gly Gly Gly Leu Val Gln Ala Gly Asp Ser Leu Arg
  1               5                  10                  15 ctc tcc tgc gcg gcc tcg gga cgc act tct cat ggg tat ggt ggc tat       96
Leu Ser Cys Ala Ala Ser Gly Arg Thr Ser His Gly Tyr Gly Gly Tyr
             20                  25                  30 ggc atg ggc tgg ttc cgc caa att cca ggg aag gag cgt gag ctt gtc      144
Gly Met Gly Trp Phe Arg Gln Ile Pro Gly Lys Glu Arg Glu Leu Val
         35                  40                  45 gca gca att agg tgg agc ggt cgt aat aca tac tat gca gac tcc gtg      192
Ala Ala Ile Arg Trp Ser Gly Arg Asn Thr Tyr Tyr Ala Asp Ser Val
     50                  55                  60 aag ggc cga ttc acc atc tcc aga gac aac gtc aag gac atg ctg tat      240
Lys Gly Arg Phe Thr Ile Ser Arg Asp Asn Val Lys Asp Met Leu Tyr
 65                  70                  75                  80 ctg caa atg aac agt ttg aaa cct gag gac acg gcc gtt tac act tgt      288
Leu Gln Met Asn Ser Leu Lys Pro Glu Asp Thr Ala Val Tyr Thr Cys
                 85                  90                  95 gca gtt cgg acg gtc cgc gtg gtt gac att tcc agt ccg gtt ggg ttt      336
Ala Val Arg Thr Val Arg Val Val Asp Ile Ser Ser Pro Val Gly Phe
            100                 105                 110 gcc tac tgg ggc cag ggg acc cag gtc acc gtc tcc tca cag gtg cag      384
Ala Tyr Trp Gly Gln Gly Thr Gln Val Thr Val Ser Ser Gln Val Gln
        115                 120                 125 ctg cag gag tca ggg gga ggc ttg gtg cag gct ggg gag tct ctg aaa      432
Leu Gln Glu Ser Gly Gly Gly Leu Val Gln Ala Gly Glu Ser Leu Lys
    130                 135                 140 ctc tcc tgt gca gcc tct gga aac acc ttc agt ggc ggc ttc atg ggc      480
Leu Ser Cys Ala Ala Ser Gly Asn Thr Phe Ser Gly Gly Phe Met Gly
145                 150                 155                 160
```

```
tgg tac cgc cag gct cca ggg aag cag cgc gag ttg gtc gca acc att        528
Trp Tyr Arg Gln Ala Pro Gly Lys Gln Arg Glu Leu Val Ala Thr Ile
            165                 170                 175 aat agt aga ggt atc aca aac tat gca gac ttc gtg aag ggc cga ttc        576
Asn Ser Arg Gly Ile Thr Asn Tyr Ala Asp Phe Val Lys Gly Arg Phe
        180                 185                 190 acc atc tcc aga gac aat gcc aag aag aca gtg tat ttg gaa atg aac        624
Thr Ile Ser Arg Asp Asn Ala Lys Lys Thr Val Tyr Leu Glu Met Asn
    195                 200                 205 agc ctg gaa cct gaa gac acg gcc gtt tat tac tgt tac act cac tac        672
Ser Leu Glu Pro Glu Asp Thr Ala Val Tyr Tyr Cys Tyr Thr His Tyr
210                 215                 220 ttc aga tcc tac tgg ggt cag ggg acc cag gtc acc                        708
Phe Arg Ser Tyr Trp Gly Gln Gly Thr Gln Val Thr
225                 230                 235
```

<210> SEQ ID NO 46
<211> LENGTH: 236
<212> TYPE: PRT
<213> ORGANISM: Unknown Organism
<220> FEATURE:
<223> OTHER INFORMATION: Description of Unknown Organism: A
      heterodimeric bivalent anti-RR6 antigen binding protein

<400> SEQUENCE: 46

```
Leu Gln Glu Ser Gly Gly Gly Leu Val Gln Ala Gly Asp Ser Leu Arg
  1               5                  10                  15

Leu Ser Cys Ala Ala Ser Gly Arg Thr Ser His Gly Tyr Gly Gly Tyr
             20                  25                  30

Gly Met Gly Trp Phe Arg Gln Ile Pro Gly Lys Glu Arg Glu Leu Val
         35                  40                  45

Ala Ala Ile Arg Trp Ser Gly Arg Asn Thr Tyr Tyr Ala Asp Ser Val
     50                  55                  60

Lys Gly Arg Phe Thr Ile Ser Arg Asp Asn Val Lys Asp Met Leu Tyr
 65                  70                  75                  80

Leu Gln Met Asn Ser Leu Lys Pro Glu Asp Thr Ala Val Tyr Thr Cys
                 85                  90                  95

Ala Val Arg Thr Val Arg Val Val Asp Ile Ser Ser Pro Val Gly Phe
            100                 105                 110

Ala Tyr Trp Gly Gln Gly Thr Gln Val Thr Val Ser Ser Gln Val Gln
        115                 120                 125

Leu Gln Glu Ser Gly Gly Gly Leu Val Gln Ala Gly Glu Ser Leu Lys
    130                 135                 140

Leu Ser Cys Ala Ala Ser Gly Asn Thr Phe Ser Gly Gly Phe Met Gly
145                 150                 155                 160

Trp Tyr Arg Gln Ala Pro Gly Lys Gln Arg Glu Leu Val Ala Thr Ile
                165                 170                 175

Asn Ser Arg Gly Ile Thr Asn Tyr Ala Asp Phe Val Lys Gly Arg Phe
            180                 185                 190

Thr Ile Ser Arg Asp Asn Ala Lys Lys Thr Val Tyr Leu Glu Met Asn
        195                 200                 205

Ser Leu Glu Pro Glu Asp Thr Ala Val Tyr Tyr Cys Tyr Thr His Tyr
    210                 215                 220

Phe Arg Ser Tyr Trp Gly Gln Gly Thr Gln Val Thr
225                 230                 235
```

<210> SEQ ID NO 47

```
<211> LENGTH: 47
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: CDS
<222> LOCATION: (6)..(29)

<400> SEQUENCE: 47 aagct gct agc cag gtg aaa ctg ctc gag cccgggaagc ttgaattc           47
      Ala Ser Gln Val Lys Leu Leu Glu
        1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      amino acid

<400> SEQUENCE: 48

Ala Ser Gln Val Lys Leu Leu Glu
  1               5

<210> SEQ ID NO 49
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
agctgctagc caggtgaaac tgctcgagcc cgggaagctt g                       41

<210> SEQ ID NO 50
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
aattcaagct tcccgggctc gagcagtttc acctggctag c                       41

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: CDS
<222> LOCATION: (1)..(18)

<400> SEQUENCE: 51 ctc gag aaa aga gct agc cccggggaat tc                               30
Leu Glu Lys Arg Ala Ser
  1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
      amino acid

<400> SEQUENCE: 52

Leu Glu Lys Arg Ala Ser
  1               5

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tcgagaaaag agctagcccc gggg                                           24

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
aattccccgg ggctagctct tttc                                           24

<210> SEQ ID NO 55
<211> LENGTH: 39
<212> TYPE: DNA
<213> ORGANISM: Artificial Sequence
<220> FEATURE:
<223> OTHER INFORMATION: Description of Artificial Sequence: Synthetic
      insert

<400> SEQUENCE: 55
aagcttagat ctggatcccg ggcaattgag atctaattc                           39

<210> SEQ ID NO 56
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
agcttagatc tggatcccgg gcaattgaga tct                                 33

<210> SEQ ID NO 57
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
aattagatct caattgcccg ggatccagat cta                                 33

<210> SEQ ID NO 58
<211> LENGTH: 124
<212> TYPE: PRT
<213> ORGANISM: Unknown Organism
<220> FEATURE:
<223> OTHER INFORMATION: Description of Unknown Organism: Anti-LAB-phage
``` fragment

<400> SEQUENCE: 58

```
Gln Val Gln Leu Gln Glu Ser Gly Gly Gly Leu Val Gln Thr Gly Gly
  1               5                  10                  15

Ser Leu Arg Leu Ser Cys Ala Ala Ser Gly Arg Thr Ser Ser Asp Tyr
             20                  25                  30

Ser Val Gly Trp Phe Arg Gln Ala Pro Gly Lys Glu Arg Glu Phe Leu
         35                  40                  45

Ala Val Met Met Leu Ser Gly Thr Gly Thr Tyr Tyr Ala Asp Ser Val
 50                  55                  60

Lys Gly Arg Ala Ala Ile Ser Arg Asp Leu Ala Lys Asn Thr Val Tyr
 65                  70                  75                  80

Leu Glu Met Asn Ser Leu Lys Pro Glu Asp Thr Ala Val Tyr Tyr Cys
             85                  90                  95

Ala Leu Asp Arg Ala Gly Trp Leu Arg Thr Glu Glu Asn Val Tyr Asp
            100                 105                 110

Tyr Trp Gly Gln Gly Thr Gln Val Thr Val Ser Ser
            115                 120
```

<210> SEQ ID NO 59
<211> LENGTH: 113
<212> TYPE: PRT
<213> ORGANISM: Unknown Organism
<220> FEATURE:
<223> OTHER INFORMATION: Description of Unknown Organism: Anti-LAB-phage
    fragment

<400> SEQUENCE: 59

```
Gln Val Gln Leu Gln Glu Ser Gly Gly Gly Leu Val Gln Pro Gly Gly
  1               5                  10                  15

Ser Leu Arg Leu Ser Cys Ala Val Ser Gly Ala Pro Phe Arg Glu Ser
             20                  25                  30

Thr Met Ala Trp Tyr Arg Gln Thr Pro Gly Lys Glu Arg Glu Thr Val
         35                  40                  45

Ala Phe Ile Thr Ser Gly Gly Ser Lys Thr Tyr Gly Val Ser Val Gln
 50                  55                  60

Gly Arg Phe Thr Ile Ser Arg Asp Ser Asp Arg Arg Thr Val Leu Leu
 65                  70                  75                  80

Gln Met Asn Asn Leu Gln Pro Glu Asp Thr Ala Val Tyr Tyr Cys His
             85                  90                  95

Arg Ala Leu Ser Asn Thr Trp Gly Gln Gly Ile Gln Val Thr Val Ser
            100                 105                 110

Ser
```

<210> SEQ ID NO 60
<211> LENGTH: 121
<212> TYPE: PRT
<213> ORGANISM: Unknown Organism
<220> FEATURE:
<223> OTHER INFORMATION: Description of Unknown Organism: Anti-LAB-
    phage fragment

<400> SEQUENCE: 60

```
Gln Val Gln Leu Gln Glu Ser Gly Gly Gly Leu Val Gln Pro Gly Gly
  1               5                  10                  15

Ser Leu Arg Leu Ser Cys Val Val Ser Gly Glu Gly Phe Ser Asn Tyr
             20                  25                  30
```

```
Pro Met Gly Trp Tyr Arg Gln Ala Pro Gly Lys Gln Arg Glu Leu Val
             35                  40                  45

Ala Ala Met Ser Glu Gly Gly Asp Arg Thr Asn Tyr Ala Asp Ala Val
         50                  55                  60

Lys Gly Arg Phe Thr Ile Ser Arg Asp Asn Ala Lys Lys Thr Val Tyr
 65                  70                  75                  80

Leu Gln Met Ser Ser Leu Lys Pro Glu Asp Thr Ala Val Tyr Tyr Cys
                 85                  90                  95

Asn Ala Ala Arg Trp Asp Leu Gly Pro Ala Pro Phe Gly Ser Trp Gly
             100                 105                 110

Gln Gly Thr Gln Val Thr Val Ser Ser
        115                 120
```

<210> SEQ ID NO 61
<211> LENGTH: 48
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 61
gtcaccgtct ctagatggcc accaggtgca gctgcaggag tcaactta           48

<210> SEQ ID NO 62
<211> LENGTH: 47
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 62
agcttaagtt gactcctcga gctgcacctg gtggccatct agagacg             47

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 63
ctagtggtac ttccggttcc cag                                       23

<210> SEQ ID NO 64
<211> LENGTH: 16
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 64
ggaaccggaa gtacca                                               16

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      amino acid

```
<400> SEQUENCE: 65

Ser Gly Thr Ser Gly Ser Gln
 1               5

<210> SEQ ID NO 66
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 66
ctagttcttc atctgcttct gcctcttcag cccag                               35

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 67
ggctgaagag gcagaagcag atgaagaa                                       28

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      amino acid

<400> SEQUENCE: 68

Ser Ser Ser Ser Ala Ser Ala Ser Ser Ala
 1               5                  10

<210> SEQ ID NO 69
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 69
ctagtggttc tccaggttca ccaggtcag                                      29

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 70
acctggtgaa cctggagaac ca                                             22

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      amino acid
```

<400> SEQUENCE: 71

Ser Gly Ser Pro Gly Ser Pro Gly Gln
  1               5

<210> SEQ ID NO 72
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 72
ctagtgctac tacaactggt tcttcaccag gtccaactca g                     41

<210> SEQ ID NO 73
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 73
agttggacct ggtgaagaac cagttgtagt agca                             34

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      amino acid

<400> SEQUENCE: 74

Ser Ala Thr Thr Thr Gly Ser Ser Pro Gly Pro Thr Gln
  1               5                  10

<210> SEQ ID NO 75
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 75
ctagtgctaa tcattctggt aatgcttctc ag                               32

<210> SEQ ID NO 76
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 76
agaagcatta ccagaatgat tagca                                       25

<210> SEQ ID NO 77
<211> LENGTH: 10

```
<212> TYPE: PRT
<213> ORGANISM: Artificial Sequence
<220> FEATURE:
<223> OTHER INFORMATION: Description of Artificial Sequence: Synthetic
      amino acid

<400> SEQUENCE: 77

Ser Ala Asn His Ser Gly Asn Ala Ser Gln
 1               5                  10
```